(12) United States Patent
Hillis et al.

(10) Patent No.: US 8,521,440 B2
(45) Date of Patent: Aug. 27, 2013

(54) SYSTEMS FOR GENOME SELECTION

(75) Inventors: W. Daniel Hillis, Encino, CA (US);
Roderick A. Hyde, Redmond, WA (US);
Edward K. Y. Jung, Bellevue, WA (US);
Robert Langer, Newton, MA (US);
Nathan P. Myhrvold, Medina, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 0 days.

(21) Appl. No.: 12/931,491

(22) Filed: Feb. 1, 2011

(65) Prior Publication Data
US 2011/0143355 A1     Jun. 16, 2011

Related U.S. Application Data

(60) Continuation of application No. 12/661,349, filed on Mar. 15, 2010, now Pat. No. 7,888,036, which is a division of application No. 11/799,424, filed on Apr. 30, 2007, now Pat. No. 7,713,728, which is a continuation-in-part of application No. 11/651,447, filed on Jan. 8, 2007, now abandoned.

(51) Int. Cl.
*G06F 19/00*     (2011.01)
*C12N 5/00*      (2006.01)

(52) U.S. Cl.
USPC .......................................... 702/19; 435/325

(58) Field of Classification Search
None
See application file for complete search history.

(56) References Cited

U.S. PATENT DOCUMENTS

| | | |
|---|---|---|
| 4,774,339 A | 9/1988 | Haugland et al. |
| 5,135,759 A | 8/1992 | Johnson |
| 5,338,854 A | 8/1994 | Kang et al. |
| 5,985,216 A | 11/1999 | Rens et al. |
| 6,555,329 B2 | 4/2003 | Jenuwein et al. |
| 6,634,759 B1 | 10/2003 | Li |
| 6,829,412 B2 | 12/2004 | Li |
| 7,648,823 B2 | 1/2010 | Hillis et al. |
| 7,709,244 B2 | 5/2010 | Callahan et al. |
| 7,709,245 B2 | 5/2010 | Hillis et al. |
| 7,713,728 B2 | 5/2010 | Hillis et al. |
| 7,718,418 B2 | 5/2010 | Hillis et al. |
| 2002/0174449 A1 | 11/2002 | West et al. |
| 2003/0027329 A1 | 2/2003 | Lee et al. |
| 2003/0046114 A1 | 3/2003 | Davies et al. |
| 2003/0157532 A1 | 8/2003 | Jenuwein et al. |
| 2004/0146865 A1 | 7/2004 | Robl et al. |
| 2004/0180430 A1 | 9/2004 | West et al. |
| 2005/0032066 A1 | 2/2005 | Heng et al. |

FOREIGN PATENT DOCUMENTS

| | | | |
|---|---|---|---|
| WO | WO 01/18236 A1 | 3/2001 | |
| WO | WO 03/020877 A2 | 3/2003 | |
| WO | WO 03/057849 A2 | 7/2003 | |

OTHER PUBLICATIONS

Verlinsky et al. Preinplantation Diagnosis of Single Gene Disorders by Two-Step Oocyte Genetic Analysis Using First and Second Polar Body Biochemical and Molecular Medicine vol. 62, pp. 182-187 (1997).*
Fiorentino et al. The minisequencing method: an alternative strategy for preimplantation genetic diagnosis of single gene disorders Molecular Human Reproduction vol. 9, pp. 399-410 (2003).*
Xu et al. First Unaffected Pregnancy Using Preimplantation Genetic Diagnosis for Sickle Cell Anemia Journal of the American Medical Association vol. 281, pp. 1701-1706 (1999).*
Durban, M. et al.; "PGD in female carriers of balanced Robertsonian and reciprocal translocations by first polar body analysis"; Human Reproduction Update; 2001; pp. 591-602; vol. 7, No. 6; European Society of Human Reproduction and Embryology.
Fiorentino, F. et al.; "Rapid Protocol for pre-conception genetic diagnosis of single gene mutations by first polar body analysis: a possible solution for the Italian patients"; Prenatal Diagnosis; published online Dec. 4, 2007 in Wiley InterScience; pp. 62-64; vol. 28; John Wiley & Sons, Ltd.
Munné, S. et al.; "The use of first polar bodies for preimplantation diagnosis of aneuploidy"; Molecular Human Reproduction vol. 1/Human Reproduction; 1995; pp. 1014-1020; vol. 10, No. 4; Oxford University Press.
Ablin, Jacob N.; Cohen, Hagit; Buskila, Dan; "Review: Mechanisms of Disease: Genetics of Fibromyalgia"; Nature Clinical Practice: Rheumatology; bearing a date of Dec. 2006; pp. 671-678; vol. 2, No. 12; Nature Publishing Group; located at: www.nature.com/clinicalpractice/rheumatology.
Alverson, Andrew J.; Theriot, Edward C.; "Research Article: Comments on Recent Progress Toward Reconstructing the Diatom Phylogeny"; Journal of Nanoscience and Nanotechnology; bearing a date of Jan. 2005; pp. 57-62; vol. 5, No. 1; American Scientific Publishers.
Aponte, Pedro M.; Van Bragt, Maaike P.A.; De Rooij, Dirk G.; Van Pelt, Ans M.M.; "Spermatogonial Stem Cells: Characteristics and Experimental Possibilities"; Acta Pathologica, Microbiologica, et Immunologica Scandinavica; bearing a date of 2005; pp. 727-742; vol. 113, Nos. 11-12; Journal Compilation.
Armanios, Mary Y., M.D.; Chen, Julian J.L., PhD; Cogan, Joy D., PhD; Alder, Jonathan K., BA; Ingersoll, Roxann G., BS; Markin, Cheryl, BS; Lawson, William E.; Xie, Mingyi, BS; Vulto, Irma, BS; Phillips, John A., III, MD; Lansdorp, Peter M., MD, PhD; Greider, Carol W., PhD; Loyd, James E., MD; "Original Article: Telomerase Mutations in Families with Idiopathic Pulmonary Fibrosis"; The New England Journal of Medicine; bearing a date of Mar. 29, 2007; pp. 1317-1326; vol. 356, No. 13; Massachusetts Medical Society; located at: http://content.nejm.org/cgi/content/abstract/356/13/1317.
Asseline, U.; "Development and Applications of Fluorescent Oligonucleotides"; Current Organic Chemistry; bearing a date of 2006; pp. 491-518; vol. 10; Bentham Science Publishers Ltd.
Bachner-Melman, Rachel; Dina, Christian; Zohar, Ada H.; Constantini, Naama; Lerer, Elad; Hoch, Sarah; Sella, Sarah; Nemanov, Lubov; Gritsenko, Inga; Lichtenberg, Pesach; Granot, Roni; Ebstein, Richard P.; "AVPR1a and SLC6A4 Gene Polymorphisms are Associated With Creative Dance Performance"; PLoS Genetics; bearing a date of Sep. 2005; pp. 0394-0403; vol. 1, No. 3, e42; located at: http://genetics.plosjournals.org/perlserv/?request=get-document&doi=10.1371/journal.pgen.0010042.

(Continued)

*Primary Examiner* — John S Brusca

(57) ABSTRACT

Systems, methods, compositions and apparatus relating to genome selection are disclosed.

50 Claims, 20 Drawing Sheets

(56) References Cited

OTHER PUBLICATIONS

Baird, Duncan M.; Britt-Compton, Bethan; Rowson, Jan; Amso, Nazar N.; Gregory, Linda; Kipling, David; "Telomere instability in the Male Germline"; Human Molecular Genetics; bearing dates of Nov. 25, 2005 and 2006; pp. 45-51; vol. 15, No. 1; Oxford University Press.

Barritt, Jason A.; Willadsen, Steen; Brenner, Carol; Cohen, Jacques; "Epigenetic and Experimental Modifications in Early Mammalian Development: Part II: Cytoplasmic Transfer in Assisted Reproduction"; Human Reproduction Update: bearing a date of 2001; pp. 428-435; vol. 7, No. 4; European Society of Human Reproduction and Embryology.

Beebe, David J.; Mensing, Glennys A.; Walker, Glenn M.; "Physics and Applications of Microfluidics in Biology"; Annual Review of Biomedical Engineering; bearing a date of 2002; pp. 261-286; vol. 4; Annual Reviews.

Bermúdez, Mercedes G.; Wells, Dagan; Malter, Henry; Munné, Santiago; Cohen, Jacques; Steuerwald, Nury M.; "Article: Expression Profiles of Individual Human Oocytes Using Microarray Technology"; Reproductive BioMedicine Online; bearing a date of Jan. 21, 2004; pp. 325-337; vol. 8, No. 3; located at: www.rbmonline.com/Article/1194.

Best, Timothy Patrick; "Localization of DNA-Binding Polyamides in Living Cells"; Thesis in Partial Fulfillment of the Requirements for the Degree of Doctor of Philosophy at California Institute of Technology, Pasadena, California; bearing dates of Jul. 22, 2004 and 2005; pp. 1-176, cover page, and ii-xiv.

Bezanehtak, Homira; Swan, M.Anne; "Study of Demembranted, Reactivated Human Spermatozoa With Decondensed Nuclei"; Journal of Experimental Zoology; bearing a date of 1999; pp. 789-797; vol. 284; Wiley-Liss, Inc.

Blasco, Maria A.; "Reviews: Telomeres and Human Disease: Ageing, Cancer and Beyond"; Nature Reviews | Genetics; bearing a date of Aug. 2005; pp. 611-622; vol. 6; Nature Publishing Group.

Bodmer, Walter F.; "The Human Genome Sequence and the Analysis of Multifactorial Traits"; Ciba Foundation Symposium: Imperial ACancer Research Fund, London, UK; bearing a date of 1987; pp. 215-228; vol. 130; located at https://www4.infotrieve.com.

Brinster, Ralph L.; "Reproductive Biology Review: Germline Stem Cell Transplantation and Transgenesis"; Science Magazine; bearing a date of Jun. 21, 2002; pp. 2174-2176; vol. 296; located at: www.sciencemag.org.

Brutsaert, Tom D.; Parra, Esteban J.; "What Makes a Champion? Explaining Variation in Human Athletic Performance"; Respiratory Physiology & Neurobiology; bearing a date of 2006; pp. 109-123; vol. 151; Elsevier B.V.; located at: www.sciencedirect.com.

Burrello, N.; Vicar!, E.; Calogero, A.E.; "Infertility and Chromosome Abnormalities in Human Gametes: Chromosome Abnormalities in Spermatozoa of Patients With Azoospermia and Normal Somatic Karyotype"; Cytogenetic and Genome Research; bearing a date of 2005; pp. 363-365; vol. I I I; S. Karger AG, Basel; located at: www.karger.com/cgr.

Byassee, Tyler A.; Chan, Warren C.W.; Nie, Shuming;"Probing Single Molecules in Single Living Cells; Probing Single Molecules in Single Living Cells"; Analytical Chemistry; bearing a date of Nov. 15, 2000; pp. 5606-5611; vol. 72, No. 22; American Chemical Society.

Chen, Caifu; Hong, Young-Kwon; Ontiveros, Sara D.; Egholm, Michael; Strauss, William M.; "Single Base Discrimination of CENP-B Repeats on Mouse and Human Chromosomes With PNA-FISH"; Mammalian Genome; bearing a date of 1999; pp. 13-18; vol. 10; Springer-Verlag New York Inc.

Chen, Caifu; Wu, Bai-Lin; Wei, Tao; Egholm, Michael; Strauss, William.M.; "Unique Chromosome Identification and Sequence-Specific Structural Analysis With Short PNA Oligomers"; Mammalian Genome; bearing a date of 2000; pp. 384-391; vol. 11; Springer-Verlag New York Inc.

Chudoba, I.; Hickmann, G.; Friedrich, T.; Jauch, A.; Kozlowski, P.; Senger, G.; "mBand: A High Resolution Multicolor Banding Technique for the Detection of Complex Intrachromosomal Aberrations"; Cytogenetic and Genome Research; bearing a date of 2004; pp. 390-393; vol. 104; S. Karger AG, Basel; located at: www.karger.com/cgr.

Clark, Adrian JL; Metherell, Louise A.; "Review: Mechanisms of Disease: The Adrenocorticotropin Receptor and Disease"; Nature Clinical Practice: Endocrinology & Metabolism; bearing a date of May 2006; pp. 282-290; vol. 2, No. 5; Nature Publishing Group; located at: www.nature.com/clinicalpractice/endmet.

Clyde, Julie M., PhD; Gosden, Roger G., DSc; Rutherford, Anthony J., MBBS; Picton, Helen M., PhD; "Demonstration of a Mechanism of Aneuploidy in Human Oocytes Using Multifluor Fluorescence in situ Hybridization"; Fertility and Sterility; bearing a date of Oct. 2001; pp. 837-840; vol. 76, No. 4; American Society for Reproductive Medicine.

Crowley, Kathleen S.; Phillion, Dennis P.; Woodard, Scott S.; Schweitzer, Barbara A.; Singh, Megh; Shabany, Hossein; Burnette, Barry; Hippenmeyer, Paul; Heitmeier, Monique; Bashkin, James K.; "Controlling the Intracellular Localization of Fluorescent Polyamide Analogues in Cultured Cells"; Bioorganic & Medicinal Chemistry Letters; bearing a date of 2003; pp. 1565-1570; vol. 13; Elsevier Science Ltd.

Dahan, Maxime; "Robert Feulgen Lecture: From Analog to Digital: Exploring Cell Dynamics With Single Quantum Dots"; Histochem Cell Biology; bearing dates of 2005 and 2006; pp. 451-456; vol. 125; Springer-Verlag.

Dejong, Jeff; "Basic Mechanisms for the Control of Germ Cell Gene Expression"; Gene/Functional Genomics; bearing a date of 2006; pp. 39-50; vol. 366; Elsevier B.V.; located at: www.sciencedirect.com and www.elsevier.com/locate/gene.

Dennis, Carina; "News Feature: Synthetic Sex Cells"; Nature; bearing a date of Jul. 24, 2003; pp. 364-366; vol. 424; Nature Publishing Group; located at: www.nature.com/nature.

De Vos, Anick; Van Steirteghem, Andre; "Aspects of Biopsy Procedures Prior to Preimplantation Genetic Diagnosis"; Prenatal Diagnosis; bearing a date of 2001; p. 767-780; vol. 21; John Wiley & Sons, Ltd.

Dieudé, Philippe; Cornélis, François; "Review: Genetic Basis of Rheumatoid Arthritis"; Joint Bone Spine; bearing a date of 2005; pp. 520-526; vol. 72; Elsevier SAS; located at: www.sciencedirect.com.

Dirks, Roeland W.; Molenaar, Chris; Tanke, Hans J.; "Visualizing RNA Molecules Inside the Nucleus of Living Cells"; Methods; Science Direct-Academic Press; bearing a date of 2003; pp. 51-57; vol. 29; Elsevier Science USA; located at www.sciencedirect.com and www.elsevier.com/locate/ymeth.

Dirks, Roeland W.; Tanke, Hans J.;"Review: Advances in Fluorescent Tracking of Nucleic Acids in Living Cells"; BioTechniques; bearing a date of Apr. 2006; pp. 489-496; vol. 40, No. 4; Eaton Publishing Company.

Dohle, G.R. et al.; "Genetic risk factors in infertile men with severe oligozoospermia and azoospermia"; Human Reproduction; bearing a date of 2002; pp. 13-16; vol. 17, No. 1; European Society of Human Reproduction and Embryology.

Edelson, Benjamin S.; Best, Timothy P.; Olenyuk, Bogdan; Nickols, Nicholas G.; Doss, Raymond M.; Foister, Shane; Heckel, Alexander; Dervan, Peter B.; "Influence of Structural Variation on Nuclear Localization of DNA-binding Polyamide-Fluorophore Conjugates"; Nucleic Acids Research; bearing a dates of 2004 and published online May 20, 2004; pp. 2802-2818; vol. 32, No. 9; Oxford University Press.

Erenpreiss, J.; Spano, M.; Erenpreisa, J.; Bungum, M.; Giwercman, A.; "Review: Sperm Chromatin Structure and Male Fertility: Biological and Clinical Aspects"; Asian Journal of Andrology; bearing a date of 2006; pp. 11-29; vol. 8, No. 1; Shanghai Institute of Materia Medica, Chinese Academy of Sciences—Blackwell Publishing.

Farrer, Matthew James; "Reviews: Genetics of Parkinson Disease: Paradigm Shifts and Future Prospects"; Nature Reviews I Genetics; bearing a date of Apr. 2006; pp. 306-318; vol. 7; Nature Publishing Group; located at: www.nature.com/reviews/genetics.

Femino, Andrea M.; Fay, Fredric S.; Fogarty, Kevin; Singer, Robert H.; "Visualization of Single RNA Transcripts in Situ"; Science; bearing a date of Apr. 24, 1998; pp. 585-590; vol. 280; located at: www.sciencemag.org.

"Fertility Evaluation and Procedures"; The Fertility Institutes; bearing dates of 2001-2006; pp. 1-4; The Fertility Institutes; located at: http://www.fertility-docs.com/fertility_gender.phtml.

Flint, J. et al.; "Chromosomal stabilisation by a subtelomeric rearrangement involving two closely related *Alu* elements"; Human Molecular Genetics; 1996; pp. 1163-1169; vol. 5, No. 8; Oxford University Press.

Gebeshuber, Ille C.; Stachelberger, Herbert; Drack, Manfred; "Research Article: Diatom Bionanotribology—Biological Surfaces in Relative Motion: Their Design, Friction, Adhesion, Lubrication and Wear"; Journal of Nanoscience and Nanotechnology; bearing a date of Jan. 2005; pp. 79-87; vol. 5, No. 1; American Scientific Publishers.

Ghetti, Bernardino; "Neurodegeneration and Hereditary Dementias: 40 Years of Learning"; Journal of Alzheimer's Disease; bearing a date of 2006; pp. 45-52; vol. 9; IOS Press and the authors.

Giardina, Emiliano; Sinibaldi, Cecilia; Novelli, Giuseppe; "Mapping the Future of Common Diseases: Lessons from Psoriasis"; Frontiers in Bioscience; bearing a date of Jan. I, 2007; pp. 1563-1573; vol. 12; located at: http://www.bioscience.org/current/vol12.htm.

Gitlin, Sue; Gibbons, WE; Gosden, RG; "Review: Oocyte Biology and Genetics Revelations From Polar Bodies"; Reproductive BioMedicine Online; bearing a date of Feb. 20, 2003; pp. 403-409; vol. 6, No. 4; RBM Online; located at www.rbmonline.com/Article/765.

Goodall, Harry; Maro, Bernard; "Major Loss of Junctional Coupling During Mitosis in Early Mouse Embryos"; The Journal of Cell Biology; bearing a date of Feb. 1986; pp. 568-575; vol. 102; The Rockefeller University Press.

Gutiérrez-Mateo, Cristina; Wells, Dagan; Benet, Jordi; Sánchez-García, Jorge F.; Bermúdez, Mercedes G.; Belil, Itziar; Egozcue, Josep; Munné, Santiago; Navarro, Joaquima; "Reliability of Comparative Genomic Hybridization to Detect Chromosome Abnormalities in First Polar Bodies and Metaphase II Oocytes"; Human Reproduction; bearing a date of 2004; pp. 2118-2125; vol. 19, No. 9; European Society of Human Reproduction and Embryology.

Hall et al.; "Primary sex determination: genetics and biochemistry"; Molecular and Cellular Biochemistry; 1980; pp. 49-66; vol. 33; Dr. W. Junk b.v. Publishers, The Hague.

Hallman, Mikko; Haataja, Ritva; "Genetic Basis of Respiratory Distress Syndrome"; Frontiers in Bioscience; bearing a date of Jan. 1, 2007; pp. 2670-2682; vol. 12; located at: http://www:bioscience.org/2007/v12/af,12263/3.htm.

Hiendleder, S.; Wolf, E.; "The Mitochondrial Genome in Embryo Technologies"; Reproduction in Domestic Animals; bearing a date of 2003; pp. 290-304; vol. 38; Blackwell Verlag, Berlin; located at: www.blackwell.de/synergy.

Hildebrand, Mark; "Research Article: Prospects of Manipulating Diatom Silica Nanostructure"; Journal of Nanoscience and Nanotechnology; bearing a date of 2005; pp. 146-157; vol. 5, No. 1; American Scientific Publishers.

Holt, William V.; Van Look, Katrien J.W.; "Review: Concepts in Sperm Heterogeneity, Sperm Selection and Sperm Competition as Biological Foundations for Laboratory Tests of Semen Quality"; Reproduction; bearing a date of 2004; pp. 527-535; vol. 127; Society for Reproduction and Fertility; located at: www.reproduction-online.org..

Hooper-Van Veen, Tineke; Berkhof, Johannes; Polman, Chris H.; Uitdehaag, Bernard M.J.; "Original Paper: Analysing the Effect of Candidate Genes on Complex Traits: An Application in Multiple Sclerosis"; Immunogenetics; bearing a date of 2006; pp. 347-354; vol. 58; Springer-Verlag.

Hughes, Simon; Yoshimoto, Maisa; Beheshti, Ben; Houlston, Richard S.; Squire, Jeremy A.; Evans, Andrew; "Research Article: The Use of Whole Genome Amplification to Study Chromosomal Changes in Prostate Cancer: Insights Into Genome-Wide Signature of Preneoplasia Associated With Cancer Progression"; BMC Genomics; bearing a date of 2006; pp. 1-10; vol. 7, No. 65; BioMed Central Ltd.; located at: http://www.biomedcentral.com/1471-2164/7/65.

Huszar, G.; Celik-Ozenci, C.; Vigue, L.; "Sperm Maturity and Genetic Integrity: ICSI Sperm Selection by Hyaluronic Acid Binding"; pp. 1-11.

Huszar et al.; "Creative kinase immunocytochemistry of human sperm-hemizona complexes: selective binding of sperm with mature creatine kinase-staining pattern"; Fertility and Sterility; Jan. 1994; pp. 136-142; vol. 61, No. 1; The American Fertility Society.

Huszar et al.; "Incomplete Development of Human Spermatozoa Is Associated With Increased Creatine Phosphokinase Concentration and Abnormal Head Morphology"; Molecular Reproduction and Development; 1993; pp. 292-298; vol. 34; Wiley-Liss, Inc.

Huszar et al.; "Putative Creatine Kinase M-Isoform in Human Sperm is Identified as the 70-Kilodalton Heat Shock Protein HspA2"; Biology of Reproduction; 2000; pp. 925-932; vol. 63; Society for the Study of Reproduction, Inc.

Huszar et al.; "Sperm Plasma Membrane Remodeling during Spermiogenetic Maturation in Men: Relationship among Plasma Membrane β1,4-Galactosyltransferase, Cytoplasmic Creatine Phosphokinase, and Creatine Phosphokinase Isoform Ratios"; Biology of Reproduction; 1997; pp. 1020-1024; vol. 56.

Ibrahim, Saleh M.; Yu, Xinhua; "Dissecting the Genetic Basis of Rheumatoid Arthritis in Mouse Models"; Current Pharmaceutical Design; bearing a date of 2006; pp. 3753-3759; vol. 12, No. 29; Bentham Science Publishers Ltd.

Jain, Shushant; Wood, Nicholas W.; Healy, Daniel G.; "Review: Molecular Genetic Pathways in Parkinson's Disease: A Review"; Clinical Science; bearing a date of 2005; pp. 355-364; vol. 109; The Biochemical Society.

Jansen et al.; "Mitochondrial Dysfunction in Reproduction;" Mitochondrion 4; 2004; pp. 577-600; Elsevier B.V. and Mitochondria Research Society.

Johnson, L.A.; Welch, G.R.; "Sex Preselection: High-Speed Flow Cytometric Sorting of X and Y Sperm for Maximum Efficiency"; Theriogenology; bearing a date of 1999; pp. 1323-1341; vol. 52; Elsevier Science Inc.

Katayma, Mika; Sutovsky, Peter; Yang, Boh S.; Cantley, Tom; Rieke, August; Farwell, Randy; Oko, Richard; Day, Billy N.; "Research: Increased Disruption of Sperm Plasma Membrane at Sperm Immobilization Promotes Dissociation of Perinuclear Theca From Sperm Chromatin After Intracytoplasmic Sperm Injection in Pigs"; Reproduction; bearing a date of 2005; pp. 907-916; vol. 130; Society for Reproduction and Fertility; located at: www.reproduction-online.org.

Kearns, W.G., Ph.D.; Pen, R.; Graham, J.; Han, T.; Carter, J.; Moyer, M.; Richter, K.S., Ph.D.; Tucker, M., Ph.D.; Hoegerman, S.F., Ph.D.; Widra, E., Ph.D.; "Preimplantation Genetic Diagnosis and Screening"; Seminars in Reproductive Medicine; bearing a date of 2005; pp. 336-347; vol. 23, No. 4; Thieme Medical Publishers, Inc.

Kendler, Kenneth S., M.D.; Greenspan, Ralph J., Ph. D.; "Reviews and Overviews: The Nature of Genetic Influences on Behavior: Lessons From "Simpler" Organisms"; The American Journal of Psychiatry; bearing a date of Oct. 2006; pp. 1683-1694; vol. 163, No. 10; located at: ajp.psychiatryonline.org.

Khan, Shaharyar M.; Bennet, James P. Jr.; "Development of Mitochondrial Gene Replacement Therapy"; Journal of Bioenergetics and Biomembranes; bearing a date of Aug. 2004; pp. 387-393; vol. 36, No. 4; Springer Science+Business Media, Inc.

Kim, Hyeran, MD; Lim, Shinn-Won, MS; Kim, Seonwoo, PhD; Kim, Jong-Woo, MD, PhD; Chang, Yun Hee, PhD; Carroll, Bernard J., MB, PhD; Kim, Doh Kwan, MD, PhD; "Original Contribution: Monoamine Transporter Gene Polymorphisms and Antidepressant Response in Koreans With Late-Life Depression"; Journal of the American Medical Association; bearing a date of Oct. 4, 2006; pp. 1609-1618; vol. 296, No. 13; American Medical Association; located at; www.jama.com.

Kimmins, Sarah; Sassone-Corsi, Paolo; "Review Article: Chromatin Remodelling and Epigenetic Features of Germ Cells"; Nature; bearing a date of Mar. 31, 2005; pp. 583-589; vol. 434; Nature Publishing Group; located at: www.nature.com/nature.

Kimura, Yasuyuki; Yanagimachi, R.; "Mouse Oocytes Injected with Testicular Spermatozoa or Round Spermatids can Develop Into Normal Offspring"; Development; bearing a date of 1995; pp. 2397-2405; The Company of Biologists Limited.

Kinane, Denis F.; Shiba, Hideki; Hart, Thomas C.; "The Genetic Basis of Periodontitis"; Periodontology 2000; bearing a date of 2005; pp. 91-117; vol. 39; Blackwell Munksgaard.

Kotaja, Noora; Bhattacharyya, Suvendra N.; Jaskiewicz, Lukasz; Kimmins, Sarah; Parvinen, Martti; Filipowicz, Witold; Sassone-Corsi, Paolo; "The Chromatoid Body of Male Germ Cells: Similarity With Processing Bodies and Presence of Dicer and MicroRNA Pathway Compontents"; PNAS/Cell Biology; bearing a date of Feb. 21, 2006; pp. 2647-2652; vol. 103, No. 8; The National Academy of Sciences of the USA; located at: www.pnas.org/cgi/doi/10.1073/pnas.0509333103.

Kubitscheck, Ulrich; Kuckmann, Oliver; Kues, Thorsten; Peters, Reiner; "Imaging and Tracking of Single GFP Molecules in Solution"; Biophysical Journal; bearing a date of Apr. 2000; pp. 2170-2179; vol. 78, No. 4; Biophysical Society.

Kujoth, G.C.; Hiona, A.; Pugh, T.D.; Someya, S.; Panzer, K.; Wohlgemuth, S.E.; Hofer, T.; Seo, A.Y.; Sullivan, R.; Jobling, W.A.; Morrow, J.D.; Van Remmen, H.; Sedivy, J.M.; Yamasoba, T.; Tanokura, M.; Weindruch, R.; Leeuwenburgh, C.; Prolla, T.A.; "Reports: Mitochodrial DNA Mutations, Oxidative Stress, and Apoptosis in Mammalian Aging"; Science; bearing a date of Jul. 15, 2005; pp. 481-484; vol. 309; located at: www.sciencemag.org.

Lee, Dong Ryul; Kaproth, Michael T.; Parks, John E.; "In Vitro Production of Haploid Germ Cells From Fresh or Frozen-Thawed Testicular Cells of Neonatal Bulls"; Biology of Reproduction; bearing a date of 2001; pp. 873-878; vol. 65; The Society for the Study of Reproduction, Inc.; located at: http://www.biolreprod.org.

Lee, Henry J.; Sinha, Animesh A.; "Cutaneous Lupus Erythematosus: Understanding of Clinical Features, Genetic Basis, and Pathobiology of Disease Guides Therapeutic Strategies"; Autoimmunity; bearing a date of Sep. 2006; pp. 433-444; vol. 39, No. 6; Informa UK Ltd.

Lee, Jang-Wong; Yang, Xiangzhong; "Factors Affecting Fertilization of Porcine Oocytes Following Intracytoplasmic Injection of Sperm"; Molecular Reproduction and Development; bearing a date of 2004; pp. 96-102; vol. 68; Wiley-Liss, Inc.; located at: www.interscience.wiley.com.

Lochner, Christine; Hemmings, Sian; Seedat, Soraya; Kinnear, Craig; Schoeman, Renata; Annerbrink, Kristina; Olsson, Marie; Eriksson, Elias; Moolman-Smook, Johanna; Allgulander, Christer, Stein, Dan J.; "Article in Press: Genetics and Personality Traits in Patients With Social Anxiety Disorder: A Case-Control Study in South Africa"; European Neuropsychopharmacology; bearing a date. Of 2006; pp. 1-7; Elsevier B.V.; located at: www.elsevier.com/locate/euroneuro.

Losic, Dusan; Rosengarten, Gary; Mitchell, James G.; Voelcker, Nicolas H.; "Research Article: Pore Architecture of Diatom Frustules: Potential Nanostructured Membranes for Molecular and Particle Separations"; Journal of Nanoscience and Nanotechnology; bearing a date of Apr. 2006; pp. 982-989; vol. 6, No. 4; American Scientific Publishers.

Lundin, Karin E.; Good, Liam; Stromberg, Roger; Graslund, Astrid; Smith, Edvard C.I.; "Biology Activity and Biotechnological Aspects of Peptide Nucleic Acid"; Advances in Genetics; bearing a date of 2006; pp. 1-51; vol. 56; Elsevier Inc.

Luo, Xingguang; Kranzler, Henry R.; Zuo, Lingjun; Wang, Shuang; Gelernter, Joel; "Article in Press: Personality Traits of Agreeableness and Extraversion are Associated With ADH4 Variation"; Biol Psychiatry; bearing a date of 2006; pp. 1-10; Society of Biological Psychiatry; located at: www.sobp.org/journal.

MacArthur, Daniel G.; North, Kathryn N.; "Review Article: Genes and Human Elite Athletic Performance"; Human Genetics; bearing a date of 2005; pp. 331-339; vol. 116; Springer-Verlag.

Macho, Betina; Brancorsini, Stefano; Fimia, Gian Maria; Setou, Mitsutoshi; Hirokawa, Nobutaka; Sassone-Corsi, Paolo; "Reports: CREM-Dependent Transcription in Male Germ Cells Controlled by a Kinesin"; Science; bearing a date of Dec. 20, 2002; pp. 2388-2390; vol. 298, No. 5602; located at: www.sciencemag.org/cgi/content/full/298/5602/2388/DC1.

Maeshima, Kazuhiro; Janssen, Samuel; Laemmli, Ulrich K.; "Specific Targeting of Insect and Vertebrate Telomeres with Pyrrole and Imidazole Polyamides"; The EMBO Journal; bearing a date of 2001; pp. 3218-3228; vol. 20, No. 12; European Molecular Biology Organization.

Mao, Rong; Pevsner, Jonathan; "Research Reviews: The Use of Genomic Microarrays to Study Chromosomal Abnormalities in Mental Retardation"; Mental Retardation and Developmental Disabilities; bearing a date of 2005; pp. 279-285; vol. 11; Wiley-Liss, Inc.

Marras, Salvatore A.E.; Tyagi, Sanjay; Kramer, Fred Russell;"Review: Real-time Assays with Molecular Beacons and Other Fluorescent Nucleic Acid Hybridization Probes"; Clinica Chimica Acta | International Journal of Clinical Chemistry | European Journal of Internal Medicine; bearing a date of 2006; pp. 48-60; vol. 363, Nos. 1-2; Elsevier B.V.; located at: www.sciencedirect.com and www.elsevier.com/locate/clinchim.

Maxwell, W.M.C.; Evans, G.; Hollinshead, F.K.; Bathgate, R.; De Graaf, S.P.; Eriksson, B.M.; Gillan, L.; Morton, K.M.; O'Brien, J.K.; "Integration of Sperm Sexing Technology Into the ART Toolbox"; Animal Reproduction Science; bearing a date of 2004; pp. 79-95; vol. 82-83; Elsevier B.V.; located at: www.elsevier.com/locate/anireprosci.

McLay, David W.; Clarke, Hugh J.;"Review: Remodelling the Paternal Chromatin at Fertilization in Mammals"; Reproduction; bearding a date of 2003; pp. 625-633; vol. 125; Society for Reproduction and Fertility.

"MicroSort® Sperm Separation"; MicroSort® Technology; bearing dates of 1998-2006; pp. 1-4 (cover page included); Genetics & IVF Institute; located at: http://www.microsort.net/technology.html.

Milewicz, Andrzej; Jedrzejuk, Diana; "Menopause: Climacteric Obesity: From Genesis to Clinic"; Gynecological Endocrinology; bearing a date of Jan. 2006; pp. 18-24; vol. 22, No. 1: Taylor & Francis.

Molenaar, Chris; Weismeijer, Karien; Verwoerd, Nico P.; Khazen, Shadi; Eils, Roland; Tanke, Hans J.; Dirks, Roeland W.; "Visualizing Telomere Dynamics in Living Mammalian Cells Using PNA Probes"; The EMBO Journal; bearing a date of 2003; pp. 6631-6641; vol. 22, No. 24; European Molecular Biology Organization.

Montsant, Anton; Maheswari, Uma; Bowler, Chris; Lopez, Pascal J.; "Review: Diatomics: Toward Diatom Functional Genomics"; Journal of Nanoscience and Nanotechnology; bearing a date of Jan. 2005; pp. 5-14; vol. 5, No. 1; American Scientific Publishers.

Moore, K.; Thatcher, W.W.; "Major Advances Associated With Reproduction in Dairy Cattle"; Journal of Dairy Science; bearing a date of 2006; pp. 1254-1266; vol. 89, No. 4; American Dairy Science Association.

Munne, Santiago; "Reviews: Preimplantation Genetic Diagnosis of Numerical and Structural Chromosome Abnormalities"; Reproductive BioMedince Online; bearing a date of Feb. 4, 2002; pp. 183-196; vol. 4, No. 2; RBM Online; located at: www.rbmonline.com/Article/382.

Nagy, Zsolt P. et al.; "Timing of oocyte activation, pronucleus formation and cleavage in humans after intracytoplasmic sperm injection (ICSI) with testicular spermatozoa and after ICSI or in-vitro fertilization on sibling oocytes with ejaculated spermatozoa"; Human Reproduction; 1998; pp. 1606-1612; vol. 13, No. 6; European Society for Human Reproduction and Embryology.

"New Sperm Selection Technology for Assisted Reproductive Technology (ART) Cleared by FDA"; OBGYN.net: PMS/PMDD; bearing a date of Jul. 8, 2006; pp. 1-2; located at: http://www.obgyn.net/pmspmdd/nmsnmdd.asp?page=/news/FDA_clears_sperm_selection_technology.

Nicholas, Frank W.; "Animal Breeding and Disease"; Philosophical Transactions of the Royal Society B; bearing a date of 2005; pp. 1529-1536; vol. 360; The Royal Society.

Oatley, Jon M.; Avarbock, Mary R.; Telaranta, Aino I.; Fearon, Douglas T.; Brinster, Ralph L.; "Identifying Genes Important for Spermatogonial Stem Cell Self-Renewal and Survival"; PNAS; bearing a date of Jun. 20, 2006; pp. 9524-9529; vol. 103, No. 25; The National Academy of Sciences of the USA; located at: www.pnas.org/cgi/doi/10.1073/pnas.0603332103.

Pappas, Janice L.; "Research Article: Geometry and Topology of Diatom Shape and Surface Morphogenesis for Use in Applications of Nanotechnology"; Journal of Nanoscience and Nanotechnology; bearing a date of Jan. 2005; pp. 120-130; vol. 5, No. 1; American Scientific Publishers.

Parks, J.E.; Lee, D.R.; Huang,S.; Kaproth, M.T.; "Prospects for Spermatogenesis in Vitro"; Theriogenology; bearing a date of 2003; pp. 73-86; vol. 59; Elsevier Science Inc.; located at: www.sciencedirect.com.

Parvinen, Martti; "Review: The Chromatoid Body in Spermatogenesis"; International Journal of Andrology; bearing a date of 2005; pp. 189-201; vol. 28; Blackwell Publishing Ltd.

Parvinen, Martti; Salo, Juha; Toivonen, Marko; Nevalainen, Olli; Soini, Erkki; Pelliniemi, Lauri J.; "Original Paper: Computer Analysis of Living Cells: Movements of the Chromatoid Body in Early Spermatids Compared with its Ultrastructure in Snap-Frozen Preparations"; Histochemistry and Cell Biology; bearing a date of 1997; pp. 77-81; vol. 108; Springer-Verlag.

Paulasova, P.; Andréo, B.; Diblik, J.; Macek, M.; Pellestor, F.; "The Peptide Nucleic Acids as Probes for Chromosomal Analysis: Application to Human Oocytes, Polar Bodies and Preimplantation Embryos"; Molecular Human Reproduction; bearing a date of 2004; pp. 467-472; vol. 10, No. 6; European Society of Human Reproduction and Embryology.

Payton, A.; "Review: Investigating Cognitive Genetics and its Implications for the Treatment of Cognitive Deficit"; Gene, Brains and Behavior; bearing a date of 2006; pp. 44-53; vol. 5, Suppl. 1; Blackwell Munksgaard.

Pellestor, F.; Anahory, T.; Hamamah, S.; "The Chromosomal Analysis of Human Oocytes. An Overview of Established Procedures"; Human Reproduction Update; bearing a date of 2005; pp. 15-32; vol. 11, No. 1; European Society of Human Reproduction and Embryology.

Pellestor, Franck; Andréo, Brigitte; Taneja, Krihan; Williams, Brett; "PNA on Human Sperm: A New Approach for in Situ Aneuploidy Estimation"; European Journal of Human Genetics; bearing a date of 2003; pp. 337-341; vol. 11; Nature Publishing Group; located at: www.nature.com/ejhg.

Pellestor, Franck, Ph.D.; Anahory, Tal, M.D.; Andreo, Brigitte, M.Sc.; Régnier-Vigouroux, Gilles, M.D.; Soulie, Jean Pierre, M.D.; Baudouin, Magalie, M.Sc.; Demaille, Jacques, M.D.; "Fast Multicolor Primed in Situ Protocol for Chromosome Identification in Isolated Cells May be Used for Human Oocytes and Polar Bodies"; Fertility and Sterility; bearing a date of Feb. 2004; pp. 408-415; vol. 81, No. 2; Elsevier Inc.

Petit, Christophe; Martel-Petit, Veronique; Fleurentin, Audrey; Monnier-Barbarino, Patricia; Jonveaux, Philippe; Gerard, Hubert; "Use of PRINS for Preconception Screening of Polar Bodies for Common Aneuploidies"; Prenatal Diagnosis; bearing a date of 1067-1071; vol. 20; John Wiley & Sons, Ltd.

Raizen, David M., M.D., Ph. D.; Mason, Thornton, B.A., M.D., M.S.C.E.; Pack, Allan I., M.B., Ch. B., Ph. D.; "Genetic Basis for Sleep Regulation and Sleep Disorders"; bearing a date of 2006; pp. 467-483; Thieme Medical Publishers, Inc.

Rankinen, Tuomo; Bray, Molly S.; Hagberg, James M.; Pérusse, Louis; Roth, Stephen M.; Wolfarth, Bernd; Bouchard, Claude; "Special Report: The Human Gene Map for Performance and Health-Related Fitness Phenotypes: The 2005 Update"; Medicine & Science in Sports & Exercise; bearing a date of 2006; pp. 1863-1888; American College of Sports Medicine.

Rechitsky, S.; Strom, C.; Verlinsky, O.; Amet, T.; Ivakhnenko, V.; Kukharenko, V.; Kuliev, A.; Verlinsky, Y.; "Allele Dropout in Polar Bodies and Blastomeres"; Journal of Assisted Reproduction and Genetics; bearing a date of 1998; pp. 253-257; vol. 15, No. 5; Plenum Publishing Corporation.

Rechitsky, S.; Verlinsky, O.; Amet, T.; Rechitsky, M.; Kouliev, T.; Strom, C.; Verlinsky, Y.; "Reliability of Preimplantation Diagnosis for Single Gene Disorders"; Molecular and Cellular Endocrinology; bearing a date of 2001; pp. S65-S68; vol. 183; Elsevier Science Ireland Ltd.; located at: www.elsevier.com/locate/mce.

Rizzuto, Rosario; Carrington, Walter; Tuft, Richard A.; "Digital Imaging Microscopy of Living Cells"; Trends in Cell Biology; Seminars in Neurology; bearing a date of Jul. 1998; pp. 288-292; vol. 26, No. 5; Elsevier Science Ltd.

Romanato, Marina; Regueira, Eleonora; Cameo, Monica S.; Baldini, Consuelo; Calvo, Lucrecia; Calvo, Juan Carlos; "Further Evidence on the Role of Heparan Sulfate as Protamine Acceptor During the Decondensation of Human Spermatozoa"; Human Reproduction; bearing a date of Jun. 24, 2005; pp. 2784-2789; vol. 20, No. 10; Oxford University Press on behalf of European Society of Human Reproduction and Embryology.

Rybouchkin, A. et al.; "Disintegration of chromosomes in dead sperm cells as revealed by injection into mouse oocytes"; Human Reproduction; 1997; pp. 1693-1698; vol. 12, No. 8; European Society for Human Reproduction and Embryology.

Saetre, P.; Strandberg, E.; Sundgren, P.-E.; Pettersson, U.; Jazin, E.; Bergstrom, T.F.; "The Genetic Contribution to Canine Personality"; Genes, Brain and Behavior; bearing a date of 2006; pp. 240-248; vol. 5; Blackwell Munksgaard.

Sandalinas, Mireia; Marquez, Carmen; Munne, Santiago; "Spectral Karyotyping of Fresh, Non-Inseminated Oocytes"; Molecular Human Reproduction; bearing a date of 2002; pp. 580-585; vol. 8, No. 6; European Society of Human Reproduction and Embryology.

Santangelo, Susan L.; Tsatsanis, Katherine; "What is Known About Autism: Genes, Brain, and Behavior"; Genomics in Health and Disease; bearing a date of 2005; pp. 71-92; vol. 5, No. 2; Adis Data Information BV.

Shaffer, Lisa G.; Bejjani, Bassem A.; "A Cytogeneticist's Perspective on Genomic Microarrays"; Human Reproduction Update; bearing a date of 2004; pp. 221-226; vol. 10, No. 3; European Society of Human Reproduction and Embryology.

Shamblott et al.; "Derivation of pluripotent stem cells from cultured human primordial germ cells"; Proc Natl. Acad. Sci. USA; Nov. 1998; pp. 13726-13731; vol. 95; The National Academy of Sciences.

Shav-Tal, Yaron; Singer, Robert H.; Darzacq; "Innovation: Imaging Gene Expression in Single Living Cells"; Nature Reviews: Molecular Cell Biology; bearing a date of Oct. 2004; pp. 856-862; vol. 5; Nature Publishing Group; located at: www.nature.com/reviews/molcellbio.

Silverman, Adam P.; Kool, Eric T.; "Quenched Probes for Highly Specific Detection of Cellular RNAs"; Trends in Biotechnology; bearing a date of May 2005; pp. 225-230; vol. 23, No. 5; Elsevier Ltd.; located at: www.sciencedirect.com.

Singer, Robert H.; David S. Lawrence; Ovryn, Ben; Condeelis, John; "Imaging of Gene Expression in Living Cells and Tissues"; Journal of Biomedical Optics; bearing a date of Sep./Oct. 2005; pp. 051406-1 to 051406-9; vol. 10, No. 5; SPIE.

Skuse, David; "Genetic Influences on the Neural Basis of Social Cognition"; Philosophical Transactions of the Royal Society B; bearing a date of 2006; pp. 2129-2141; vol. 361; The Royal Society.

Sofikitis, N.; Pappas, E.; Kawatani, A.; Baltogiannis, D.; Loutradis, D.; Kanakas, N.; Giannakis, D.; Dimitriadis, F.; Tsoukanelis, K.; Georgiou, I.; Makrydimas, G.; Mio, Y.; Tarlatzis, V.; Melekos; M.; Miyagawa, I.; "Efforts to Create an Artificial Testis: Culture Systems of Male Germ Cells Under Biochemical Conditions Resembling the Seminiferous Tubular Biochemical Environment"; Human Reproduction Update, bearing a date of 2005; pp. 229-259; vol. 11, No. 3; Oxford University Press.

Spikings, E.C.; Alderson, J.; St. John, J.C.; "Transmission of Mitochondrial DNA Following Assisted Reproduction and Nuclear Transfer"; Human Reproduction Update; bearing a date of Mar. 31, 2006; pp. 401-415; vol. 12, No. 4; Oxford University Press and European Society of Human Reproduction and Embryology.

Sterrenburg, F.A.S.; Tiffany, Mary Ann; Del Castillo, María Esther Meave; "Research Article: Valve Morphogenesis in the Diatom Genus Pleurosigma W. Smith (Bacillariophyceae): Nature's Alternative Sandwich"; Journal of Nanoscience and Nanotechnology; bearing a date of Jan. 2005; pp. 140-145; vol. 5, No. 1; American Scientific Publishers.

Stone, H.A.; Stroock, A.D.; Ajdari, A.; "Engineering Flows in Small Devices: Microfluidics Toward a Lab-on-a-Chip"; Annual Review of Fluid Mechanics; bearing a date of 2004; pp. 381-411 and Ci-C4; vol. 36; Annual Reviews.

Stouffs, Katrien et al.; "The choice and outcome of the fertility treatment of 38 couples in whom the male partner has a Yq microdeletion"; Human Reproduction; 2005; pp. 1887-1896; vol. 20, No. 7; Oxford University Press.

Stubbs, Lisa; "Mouse and Human Genetic Similarities"; Oak Ridge National Laboratory; 1 page; located at http://www.thetech.org/genetics/images/ask/mouseFlumanGeneticSim.gif; accessed on May 19, 2010.

Sudarshan, Sunil; Linehan, W. Marston; "Genetic Basis of Cancer of the Kidney"; Seminars in Oncology; bearing a date of Oct. 2006; pp. 544-551; vol. 33, No. 5; Elsevier, Inc.

Surani, Azim M.; "Reprogramming of genome function through epigenetic inheritance"; Nature; Nov. 2001; pp. 122-128; vol. 414; Macmillan Magazines Ltd.

Tadakuma, Hisashi; Ishihama, Yo; Shibuya, Toshiharu; Tani, Tokio; Funatsu, Takashi; "Imaging of Single mRNA Molecules Moving Within a Living Cell Nucleus"; Biochemical and Biophysical Research Communications; bearing a date of 2006; pp. 772-779; vol. 344; Elsevier Inc.; located at: www.sciencedirect.com and www.elsevier.com/locate/ybbrc.

Tang, Bor Luen; "Molecular Genetic Determinants of Human Brain Size"; Biochemical and Biophysical Research Communications; bearing a date of Jul. 7, 2006; pp. 911-916; vol. 345, No. 3; Elsevier, Inc.; located at www.sciencedirect.com and www.elseviercom/locatelybbrc.

Tanke, Hans J.; Dirks, Roeland W.; Raap, Ton; FISH and Immunocytochemistry: towards visualizing single target molecules in Living Cells; Current Opinion in Biotechnology; bearing a date of 2005; pp. 49-54; vol. 16; Elsevier Ltd.; located at www.sciencedirect.com.

Tesarik, Jan; "Oocyte Activation After Intracytoplasmic Injection of Mature and Immature Sperm Cells"; Human Reproduction; bearing a date of 1998; pp. 117-127; vol. 13, Supp. 1; European Society for Human Reproduction & Embryology.

Thamatrakoln, Kimberlee; Hildebrand, Mark; "Research Article: Approaches for Functional Characterization of Diatom Silicic Acid Transporters"; Journal of Nanoscience and Nanotechnology; bearing a date of Jan. 2005; pp. 1580-166; vol. 5, No. 1; American Scientific Publishers.

Tiffany, Mary Ann; "Research Article: Diatom Auxospore Scales and Early Stages in Diatom Frustule Morphogenesis: Their Potential for Use in Nanotechnology"; Journal of Nanoscience and Nanotechnology; bearing a date of Jan. 2005; pp. 131-139; vol. 5, No. 1; American Scientific Publishers.

Topol, Eric J.; Smith, Jonathan; Plow, Edward F.; Wang, Qing K.; "Genetic Susceptibility to Myocardial Infarction and Coronary Artery Disease"; Human Molecular Genetics; bearing a date of 2006; pp. R117-R123; vol. 15, No. 2; The Author(s); located at http://creativecommons.org/licenses/by-nc/2.0/uk/.

Treszl, Andras; Tulassay, Tivadar; Vasarhelyi, Barna; "Genetic Basis for Necrotizing Enterocolitis—Risk Factors and Their Relations to Genetic Polymorphisms"; Frontiers in Bioscience; bearing a date of Jan. I, 2006; pp. 570-580; vol. 11; located at http://www.bioscience.org/current/vol11.htm.

Tsai, Ming C.; Takeuchi, Takumi; Bedford, J. Michael; Reis, Marcos M.; Rosenwaks, Zev; Palermo, Gianpiero D.; "Opinion: Alternative Sources of Gametes: Reality or Science Fiction?"; Human Reproduction; bearing a date of 2000; pp. 988-998; vol. 15, No. 5; European Society of Human Reproduction and Embryology.

Tuerlings et al.; "Genetics of Male Factor Subfertility;" European Journal of Obstetrics and Gynecology and Reproductive Biology 89; 2000; pp. 117-121; Elsevier Science Ireland Ltd.; Ireland.

Twisk, M.; Mastenbroek, S.; Van Wely, M.; Heineman, MJ; Van Der Veen, F.; Repping, S.; Preimplantation Genetic Screening for Abnormal Number of Chromosomes (Aneuploidies) in in Vitro Fertilisation or Intracytoplasmic Sperm Injection (Review); Cochrane Database of Systematic Reviews; bearing a date of 2006; pp. 1-16 (plus 2 cover pages); Issue 1; John Wiley & Sons, Ltd.; located at: http://www.thecochranelibrarv.com.

Ventela, Sami; Toppari, Jorma; Parvinen, Martti; "Intercellular Organelle Traffic Through Cytoplasmic Bridges in Early Spermatids of the Rat: Mechanisms of Haploid Gene Product Sharing"; Molecular Biology of the Cell; bearing a date of Jul. 2003; pp. 2768-2780; vol. 14; The American Society for Cell Biology.

Verlinsky, Y.; Cieslak, J.; Ivakhnenko, V.; Evsikov, S.; Wolf, G.; White, M.; Lifchez, A.; Kaplan, B.; Moise, J.; Valle, J.; Ginsberg, N.; Strom, C.; Kuliev, A.; "Chromosomal Abnormalities in the First and Second Polar Body"; bearing a date of 2001; pp. S47-S49; vol. 183; Elsevier Science Ireland Ltd.; located at: www.elsevier.com/locate/mce.

Verlinsky, Y.; Cieslak, J.; Ivakhnenko, V.; Evsikov, S.; Wolf, G.; White, M.; Lifchez, A.; Kaplan, B.; Moise, J.; Valle, J.; Ginsberg, N.; Strom, C.; Kuliev, A.; "Preimplantation Diagnosis of Common Aneuploidies by the First-and Second-Polar Body FISH Analysis"; Journal of Assisted Reproduction and Genetics; bearing a date of 1998; pp. 285-289; vol. 15, No. 5; Plenum Publishing Corporation.

Verlinsky, Yury; Evsikov, Sergei; "Karyotyping of Human Oocytes by Chromosomal Analysis of the Second Polar Bodies"; Molecular Human Reproduction; bearing a date of 1999; pp. 89-95; vol. 5, No. 2; European Societyof Human Reproduction and Embryology.

Vilfan, Igor D.; Conwell, Christine C.; Hud, Nicholas V.; "Formation of Native-like Mammalian Sperm Cell Chromatin with Folded Bull Protamine"; The Journal of Biological Chemistry; bearing a date of May 7, 2004; pp. 20088-20095; vol. 279, No. 19; The American Society for Biochemistry and Molecular Biology, Inc.; located at: www.jbc.org.

Wakayama, T.; Hayashi, Y.; Ogura, A.; "Participation of the Female Pronucleus Derived From the Second Polar Body in Full Embryonic Development of Mice"; Journal of Reproduction and Fertility; bearing a date of 1997; pp. 263-266; vol. 110; Journals of Reproduction and Fertility Ltd.

Wakayama, Teruhiko; Yanagimachi, R.; "The First Polar Body Can be Used for the Production of Normal Offspring in Mice"; Biology of Reproduction; bearing a date of 1998; pp. 100-104; vol. 59.

Wells, Dagan, PhD; Escudero, Tomas, B.Sc; Levy, Brynn, PhD; Hirschhorn, Kurt, MD; Delhanty, Joy D.A., PhD; Munne, Santiago, PhD; "First Clinical Application of Comparative Genomic Hybridization and Polar Body Testing for Preimplantation Genetic Diagnosis of Aneuploidy"; Fertility and Sterility; bearing a date of Sep. 2002; pp. 543-549; vol. 78, No. 3; American Society for Reproductive Medicine.

Wheeler, Matthew B.; Rutledge, Jack J.; Fischer-Brown, Amy; Vanetten, Tara; Malusky, Samantha; Beebe, David J.; "Application of Sexed Semen Technology to in Vitro Embryo Production in Cattle"; Theriogenology; bearing a date of 2006; pp. 219-227; vol. 65; Elsevier Inc.; located at: www.journals.elsevierhealth.com/periodicals/the.

White, Stephanie A.; Fisher, Simon E.; Geschwind, Daniel H.; Scharff, Constance; Holy, Timothy E.; "Mini-Symposium: Singing Mice, Songbirds, and More: Models for FOXP2 Function and Dysfunction in Human Speech and Language"; The Journal of Neuroscience; bearing a date of Oct. 11, 2006; pp. 10376-10379; vol. 26, No. 41; Society for Neuroscience.

Yanagimachi, Ryuzo; "Fertilization and Development Initiation in Orthodox and Unorthodox Ways: From Normal Fertilization to Cloning"; Advances in Biophysics; bearing a date of 2003; pp. 49-89; vol. 37; Elsevier Science Ireland Ltd.

Yanagimachi, Ryuzo; "Male Gamete Contributions to the Embryo"; Annals New York Academy of Sciences; bearing a date of 2005; pp. 203-207; vol. 1061; New York Academy of Sciences.

Yong, Hwan Yul; Hong, Ji Young; Kang, Sung Keun; Lee, Byeong Chun; Lee, Eun Song; Hwang, Woo Suk; "Sperm Movement in the Ooplasm, Dithiothreitol Pretreatment and Sperm Freezing Are Not Required for the Development of Porcine Embryos Derived From Injection of Head Membrane-Damaged Sperm"; Theriogenology; bearing a date of 2005; pp. 783-794; vol. 63; Elsevier, Inc.; located at www.sciencedirect.com and www.journals.elsevierhealth.com/periodicals/the.

Ho et al.; "Hematopoietic stem cells: can old cells learn new tricks?"; Journal of Leukocyte Biology; May 2003; pp. 547-555; vol. 73.

Jordan et al.; "The Biology of Stem Cells"; The Biomedical Engineering Handbook: Second Edition, Chapter 116; bearing a date of 2000; pp. 1-8; CRC Press LLC.

Levine et al.; "Inheriting Maternal mtDNA"; Science; Nov. 25, 2011; pp. 1069-1070, and one cover page; vol. 334; American Association for the Advancement of Science.

Mroz et al.; "Meiotic aneuploidy in the XXY mouse: evidence that a compromised testicular environment increases the incidence of meiotic errors"; Human Reproduction; Oct. 1998 and Jan. 1999; pp. 1151-1156; vol. 14, No. 5; European Society of Human Reproduction and Embryology.

Tournaye et al.; "Testicular sperm recovery in nine 47,XXY Klinefelter patients"; Human Reproduction; Feb. 1996 and May 1996; pp. 1644-1649; vol. 11, No. 8; European Society for Human Reproduction and Embryology.

Van Saen et al.; "Can pubertal boys with Klinefelter syndrome benefit from spermatogonial stem cell banking?"; Human Reproduction; Dec. 12, 2011; pp. 1-8; vol. 0, No. 0; Oxford University Press.

Pritchard et al.; "Genetic analysis of the human Y chromosome by chromosome-mediated gene transfer"; Development 101; bearing a date of 1987; pp. 59-65; Supplement; The Company of Biologists Limited; Great Britain.

* cited by examiner

SYSTEMS FOR GENOME SELECTION

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the United States Patent Office (USPTO) extra-statutory requirements, the present application is a CONTINUATION application of U.S. patent application Ser. No. 12/661,349, now U.S. Pat. No. 7,888,036, titled SYSTEMS FOR GENOME SELECTION, naming W. Daniel Hillis, Roderick A. Hyde, Edward K. Y. Jung, Robert Langer, Nathan P. Myhrvold and Lowell L. Wood, Jr, as inventors, filed 15 Mar. 2010, which is a DIVISIONAL of U.S. patent application Ser. No. 11/799,424, now U.S. Pat. No. 7,713,728, titled SYSTEMS FOR GENOME SELECTION, naming W. Daniel Hillis, Roderick A. Hyde, Edward K. Y. Jung, Robert Langer, Nathan P. Myhrvold and Lowell L. Wood, Jr, as inventors, filed 30 Apr. 2007, which is a CONTINUATION-IN-PART of Ser. No. 11/651,447 titled SYSTEMS FOR GENOME SELECTION, naming W. Daniel Hillis, Roderick A. Hyde, Edward K. Y. Jung, Robert Langer, Nathan P. Myhrvold and Lowell L. Wood, Jr, as inventors, filed 8 Jan. 2007 now abandoned.

U.S. patent application Ser. No. 12/661,393, entitled SYSTEMS FOR GENOME SELECTION, naming W. Daniel Hillis, Roderick A. Hyde, Edward K. Y. Jung, Robert Langer, Nathan P. Myhrvold and Lowell L. Wood, Jr, as inventors, filed 15 Mar. 2010, is related to the present application.

U.S. patent application Ser. No. 12/592,967, entitled SYSTEMS FOR GENOME SELECTION, naming W. Daniel Hillis, Roderick A. Hyde, Edward K. Y. Jung, Robert Langer, Nathan P. Myhrvold and Lowell L. Wood, Jr, as inventors, filed 4 Dec. 2009, is related to the present application.

U.S. patent application Ser. No. 12/653,305, entitled SYSTEMS FOR GENOME SELECTION, naming W. Daniel Hillis, Roderick A. Hyde, Edward K. Y. Jung, Robert Langer, Nathan P. Myhrvold and Lowell L. Wood, Jr, as inventors, filed 11 Dec. 2009, is related to the present application.

U.S. patent application Ser. No. 11/799,422, entitled SYSTEMS FOR GENOME SELECTION, naming Heather L. Callahan, W. Daniel Hillis, Roderick A. Hyde, Edward K. Y. Jung, Robert Langer, Nathan P. Myhrvold and Lowell L. Wood, Jr, as inventors, filed 30 Apr. 2007, is related to the present application.

U.S. patent application Ser. No. 11/799,423, entitled SYSTEMS FOR GENOME SELECTION, naming W. Daniel Hillis, Roderick A. Hyde, Edward K. Y. Jung, Robert Langer, Nathan P. Myhrvold and Lowell L. Wood, Jr, as inventors, filed 30 Apr. 2007, is related to the present application.

U.S. patent application Ser. No. 11/799,425, entitled SYSTEMS FOR GENOME SELECTION, naming W. Daniel Hillis, Roderick A. Hyde, Edward K. Y. Jung, Robert Langer, Nathan P. Myhrvold and Lowell L. Wood, Jr, as inventors, filed 30 Apr. 2007, is related to the present application.

U.S. patent application Ser. No. 11/799,426, entitled SYSTEMS FOR GENOME SELECTION, naming W. Daniel Hillis, Roderick A. Hyde, Edward K. Y. Jung, Robert Langer, Nathan P. Myhrvold and Lowell L. Wood, Jr, as inventors, filed 30 Apr. 2007, is related to the present application.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

The present application relates, in general, to methods of selecting germ line genomes at least partially based on one or more genetic characteristics of the germ line genomes and related systems implementations, apparatus and/or compositions. Such methods, systems, apparatus, and/or compositions are useful for selecting and/or identifying germ line genomes optionally for use in fertilization. Germ line genomes may be selected to include certain target genetic characteristics and/or to exclude certain target characteristics as optionally determined by a systems operator. Illustrative examples include selection of germ lines that exclude certain genetic characteristics linked with disease risk, and/or that include certain genetic characteristics linked with milk production or egg laying.

Various methods for selecting one or more germ line genomes are disclosed, including but not limited to, various methods for selecting male germ line genomes and/or female germ line genomes. Methods for selecting male germ line genomes include, but are not limited to, hybridization-based selection methods, female genetic characteristics-based selection methods, chromatin decondensation-based selection methods, and/or spermatid subtractive determination-based selection methods. Methods for selecting female germ line genomes include, but are not limited to, male genetic characteristics-based selection methods and/or polar body subtractive determination-based selection methods.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
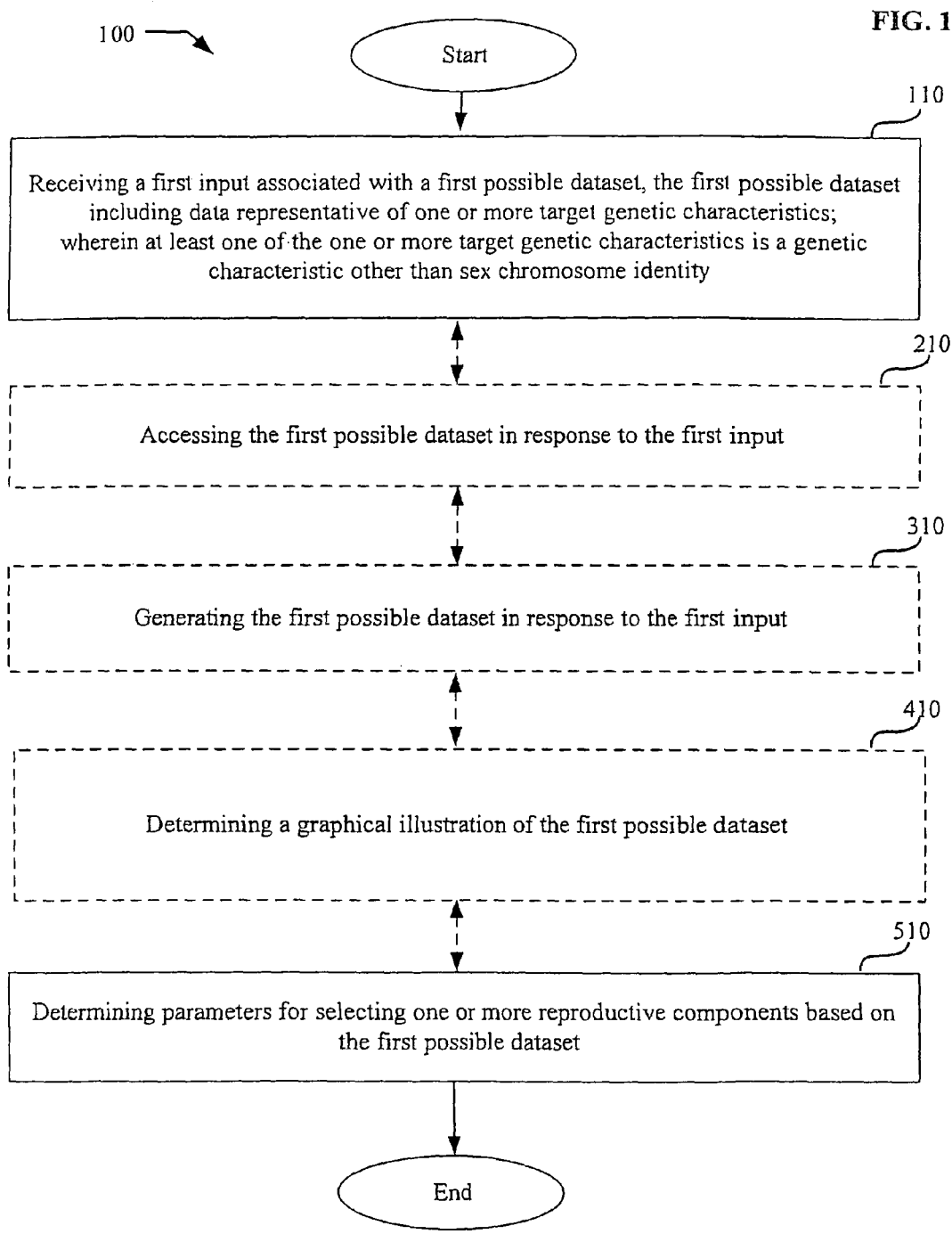
FIG. 1, FIG. 2, and FIG. 3 show operational flows representing illustrative embodiments of operations related to determining parameters for selecting one or more reproductive components based on a first possible dataset.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application relates, in general, to systems, apparatus, compositions, and methods of selecting germ line genomes. Those having skill in the art will appreciate that the specific systems, apparatus, compositions, and methods described herein are intended as merely illustrative of their more general counterparts.

As used herein, the term "germ line" means germ cells having genetic material that may be passed to offspring. Germ cells include, but are not limited to, gametogonia (e.g. spermatogonia and oogonia), gametocytes (e.g. spermatocytes and oocytes) and gametes (e.g. spermatozoa and ova).

As used herein, the term "haploid germ line" means germ cells having one set of the genetic material that may be passed to offspring. Haploid germ cells include, but are not limited to, second polar bodies, ova, secondary spermatocytes, spermatids, and spermatozoa.

As used herein, the term "genome(s)" means the hereditary information of an organism typically encoded in nucleic acids, either DNA, or RNA, and including both genes and non-coding sequences. The genome may refer to the nucleic acids making up one set of chromosomes of an organism (haploid genome) or both sets of chromosomes of an organism (diploid genome) depending on the context in which it is used. The genome may also include, or be limited to, a mitochondrial genome or a chloroplast genome, for example, depending on the context. The genome may be at least partially isolated, part of a nucleus, and/or in a cell, such as but not limited to, a germ cell or a somatic cell. In some embodiments, one or more genomes may include, but not be limited to, nuclear, organellar, chloroplast and/or mitochondrial genomes.

As used herein, the term "genetic characteristic(s)" means any measurable, detectable, and/or identifiable element encoded by, associated with, correlated with, and/or linked to one or more nucleic acid sequences, chromosomal structures, or genomic determinants. The characteristic or element may include, but not be limited to, one or more of a repeat sequence, an inversion, an insertion, a deletion, a substitution, a duplication, a cross-over, a recombination, a SNP, a haplotype, a centromere sequence, a methylation pattern, an epigenetic element, an intron, an exon, a regulatory sequence, an intergenic sequence, and/or a coding or non-coding sequence of nucleotides. The characteristic or element may also include, but not be limited to, allelic markers, alleles, disease markers, genetic abnormalities, genetic diseases, chromosomal abnormalities, genetic mutations and/or protein coding sequences. The characteristic or element may also include, but not be limited to, aspects of mitochondrial nucleic acid sequences and mitochondria. The characteristic or element may also include, but not be limited to, aspects of telomeres including, but not limited to, telomere sequence, telomere repeats and telomere lengths. The characteristic or element may include, but not be limited to, one or more of one or more physical attributes, mental attributes, intellectual attributes, or psychological attributes, or a combination thereof.

As used herein, the term "physical attributes" means any measurable, detectable, and/or identifiable characteristic that may be seen, touched, heard, smelled, or felt or that is involved in one of these processes and is encoded by, associated with, correlated with, and/or linked to one or more nucleic acid sequences, chromosomal structures, or genomic determinants. Examples include, but are not limited to, characteristics associated with height, disease state, body type, hip dysplasia, vision, strength, flexibility, speed, coordination, gait, foot color, lactation, fertility, weight, pelt, skin, skeleto-muscular, longevity, hair, eyes, fur, fleece, wool, hair pattern, hair color, eye color, eye sight, bone length, bone density, skin color, fur thickness, fur color, fur texture (e.g. rough, smooth, thin, thick), fleece color, fleece thickness, wool thickness, and wool color.

As used herein the term "mental attributes" means any measurable, detectable, and/or identifiable characteristics related to the functioning of the mind encoded by, associated with, correlated with, and/or linked to one or more nucleic acid sequences, chromosomal structures, or genomic determinants. Mental attributes may include, but are not limited to intellectual attributes and psychological attributes. Examples include, but are not limited to, intelligence, disposition, mental disorders, depression, insanity, persistence and self-confidence.

The genetic basis for physiology, biochemistry, disease, physical traits, mental traits, intellectual traits, and/or psychological traits of biological entities is known in the art. The genetic basis is determined optionally through associations, correlations and/or linkages among one or more genetic characteristics (Ciba Found. Symp. (1987) 130:215-228). Genetic determinants may be dominant, recessive, partial, and/or multi-factorial. In some embodiments, homozygous alleles may be selected and/or heterozygous alleles may be selected. Additional genetic associations are identifiable using the techniques described in the referenced art.

Illustrative examples of genetic associations, correlations, and/or linkages include, but are not limited to, genetic mechanisms of disease (Nat. Clin. Prat. Rheumatol. (2006) 2:671-678; Curr. Pharm. Des. (2006) 12:3753-3759; Semin. Oncol. (2006) 33:544-551; J. Alzheimers Dis. (2006) 9:45-52; Hum. Mol. Genet. (2006) 15:R117-23; Front. Biosci. (2007) 12:1563-1573; Am. J. Pharmacogenomics (2005) 5:71-92; Front. Biosci. (2007) 12:2670-2682; Autoimmunity (2006) 39:433-444; Nat. Clin. Pract. Endocrinol. Metab. (2006) 2:282-290; Immunogenetics (2006) 58:347-354; BMC Genomics (2006) 7:65; Nat. Rev. Genet. (2006) 7:306-318; Gynecol. Endocrinol. (2006) 22:18-24; Joint Bone Spine (2005) 72:520-526; J. Hypertension (2005) 23:2127-2143; Clin. Sci. (London) (2005) 109:355-364; Front. Biosci. (2006) 11:570-580; Periodontol. 2000 (2005) 39:91-117; Philos. Trans. R. Soc. Lond. B. Biol. Sci. (2005) 360:1529-36), molecular determinants of brain size (Biochem. Biophys. Res. Commun. (2006) 345:911-916), genetic influences on cognition (Philos. Trans. R. Soc. Lond. B. Biol. Sci. (2006) 361:2129-2141; Genes Brain Behavior (2006) 5:44-53; Ment. Retard Dev. Disabil. Res. Rev. (2005) 11:279-285), genetic basis for sleep regulation (Semin. Neurol. (2006) 26:467-483), genetic influences on behavior (Am. J. Psychiatry (2006) 163:1683-1694), genetics of speech (J. Neuroscience (2006) 26:10376-10379); genetic associations for personality (Biol. Psychiatry (2006) Oct. 24; Eur. Neuropsychopharmacol. (2006) Aug. 7; Genes Brain Behay. (2006) 5:240-248); and genetic relationship to athletic performance (Respir. Physiol. Neurobiol. (2006) 151:109-123; Hum. Genet. (2005) 116:331-339; Med. Sci. Sports Exerc. (2006) 38:1863-1888; PLoS Genet. (2005) 1:e42). Illustrative examples of genetic basis for susceptibility and/or resistance for disease include but are not limited to genetic determinants or predispositions for Tay-Sachs disease and sickle cell disease (optionally heterozygous alleles are preferred), as well as modified T cell receptors associated with protection from HIV infection.

As used herein, the term "reference genetic characteristic" means a genetic characteristic that is used as a comparator. Optionally, the comparator can be neutral, desirable, or not desirable. A reference genetic characteristic may be selected for or selected against.

As used herein, the term "target genetic characteristic" means a genetic characteristic that is used as a goal. A target genetic characteristic may be determined by comparison with reference genetic characteristics, for example. A target genetic characteristic may be selected for or selected against, unless context dictates otherwise.

As used herein, the term "weighted analysis" means according one or more target traits and/or genetic characteristics greater, equal or lesser weight based on identifiable criteria. Weighting may be objective, subjective, programmable, and/or user defined.

As used herein, the term "single nucleotide polymorphism (s) or SNP(s)" means a nucleic acid sequence variation occurring when a single nucleotide—A, T, C, or G—in the genome (or other shared sequence) differs between members of a species (or between paired chromosomes in an individual). Within a population, SNPs can be assigned a minor allele frequency, the ratio of chromosomes in the population carrying the less common variant to those with the more common variant. SNPs with a minor allele frequency of $\geq 1\%$ occur every 100 to 300 bases along the human genome, on average, where two of every three SNPs substitute cytosine with thymine. SNPs may fall within coding sequences of genes, non-coding regions of genes, or in the intergenic regions between genes. A SNP within a coding region, in which both forms lead to the same protein sequence, is termed synonymous; if different proteins are produced they are non-synonymous. SNPs that are not in protein coding regions may have consequences for gene splicing, transcription factor binding, or the sequence of non-coding RNA, for example, and/or may indicate the haplotype of the organism.

As used herein, the term "haplotype" means the genetic make up of nucleic acid such as, but not limited to, an individual chromosome, a chromatid, a locus, or an entire genome. In the case of diploid organisms, a genome-wide haplotype comprises one member of the pair of alleles for each locus (that is, half of a diploid genome). A haplotype refers to a set of SNPs on a chromatid that are statistically associated. These associations, and the identification of a few alleles of a haplotype block, can identify other polymorphic sites in its region. Methods for determining haplotypes are known in the art and include, but are not limited to, fluorescent in situ hybridization (FISH) referenced herein.

As used herein, the term "chromosomal characteristic(s)" means normal and abnormal features of chromosomes. Chromosomal characteristics include, but are not limited to, ploidy, translocations, insertions, deletions, rearrangements, and/or mutations. Chromosomal aberrations are frequently associated with lethality and genetic disorders. The numbers of known associations have increased dramatically with the advent of the Human Genomes Project, and have lead to extensive web-based information on genetic disorders. Methods for detecting chromosomal characteristics are known in the art and described herein.

As used herein, the term "nucleic acid(s)" means one or more complex, high-molecular-weight biochemical macromolecules composed of nucleotide chains. Nucleic acids include, but are not limited to, one or more forms of deoxyribonucleic acid (DNA) and ribonucleic acid (RNA). Nucleic acid sequence(s) refers the order of the nucleotides along one or more nucleic acid strands. Methods of determining nucleic acid sequences including target nucleic acid sequences are known in the art. In some embodiments, one or more nucleic acid sequences include, but are not limited to, those that encode one or more proteins, are transcribed into one or more RNA (including, but not limited to, rRNA, tRNA and/or siRNA), are regulatory sequences or repeating sequences, and/or have an at least partially undefined/unknown role. In some embodiments, one or more nucleic acid sequences include, but are not limited to, introns, exons, junk DNA, telomeres and centromeres, pseudogenes and/or hot-spots for duplication of DNA regions.

As used herein, the term "chromatin" means a complex of DNA and protein typically found, for example, inside the nuclei of eukaryotic cells. The nucleic acids are generally in the form of double-stranded DNA except for some germ line cells, or undergoing meiosis or mitosis. In somatic cells and some, but not all, germ line cells, the major proteins involved in chromatin are histones. In some germ line cells, including but not limited to, spermatozoa and some spermatids, the major proteins involved in chromatin are protamines.

As used herein, the term "condensed chromatin" means the more tightly packaged DNA/protein complex that occurs to varying extents during various stages of mitosis & meiosis, for example. During spermiogenesis, spermatid chromatin is remodeled into a more tightly packaged structure where histones are partially or mostly displaced, and partially or completely replaced by protamines (small, arginine-rich proteins). As a result, some but not all spermatids, as well as spermatozoa, have partially or completely condensed chromatin.

As used herein, the term "condensed, decondensation, and/or recondensation" refers to protamine-based condensation of chromatin unless context dictates otherwise.

As used herein, the term "polyamide" means a molecule, optionally a polymer, containing one or more units, each one optionally a monomer, joined by peptide bonds. The units are optionally natural and/or non-natural amino acids. Although not intended to be limiting, polyamides are understood to bind to nucleic acids, such as DNA, such that the double helix is not disrupted, apparently by binding to the minor or major groove of the double helix.

As used herein, the term "protein nucleic acid" means a nucleic acid with a backbone composed of repeating N-(2-aminoethyl)-glycine units linked by peptide bonds. The various purine and pyrimidine bases are linked to the backbone by methylene carbonyl bonds. PNA binds to DNA by displacing one of the strands and forming Watson-Crick base pairs with the other strand. PNA also binds to RNA by Watson-Crick base pairs.

As used herein, the term "related spermatids" means one or more of the four spermatids that arise during meiosis of a spermatogonium through first and second spermatocytes. The four spermatids that are generated from a single spermatogonium are "related" as used herein. The haplotype of one or more of the related spermatids may be partially and/or completely determined by knowing the haplotype of a related spermatogonium (or any related diploid cell) and the haplotypes of one or more of the other related spermatids. The haplotype of one of the related spermatids may be completely determined by knowing the haplotype of a related spermatogonium (or any related diploid cell) and the haplotypes of the other three related spermatids.

As used herein, the term "related polar bodies" means one or more of the first and second polar bodies that arise during meiosis of a primary oocyte. The three polar bodies that arise from single primary oocyte are "related" as used herein. The haplotypes of one or more of the related polar bodies and/or related ovum can be determined by knowing the haplotype of the primary oocyte (or any related diploid cell) and one or more of the polar body ovum haplotypes. The "related ovum" is the ovum arising from the primary oocyte term which the related polar bodies arose.

As used herein, the term "related female germ line genomes" means a female germ line genome that arises during meiosis of a primary oocyte. Related female germ line genomes include secondary oocytes, ova, and polar bodies, including first polar bodies and second polar bodies.

As used herein, the term "related diploid cell" means a diploid germ line or somatic cell from the same biological entity as a related spermatid or a related polar body.

As used herein, the term "at least partially" means partially or completely. "Completely" means as completely as reasonably possible scientifically and/or economically. "Partially" means anything less than completely, but more than not at all. Partially includes, but is not limited to 99%, 98%, 97%, 96%, 95%, 90%, 85%, 80%, 75%, 70%, 65%, 60%, 55%, 40%, 30%, 25%, 15%, 10%, 5%, 4%, 3%, 2%, and/or 1%. Partially includes, but is not limited to, 1-99, 5-99, 10-99, 25-99, 40-99, 60-99, 80-99, 5-90, 5-75, 5-55, 5-30, 5-15, 5-10, 25-95, 25-85, 25-65, 25-45, 60-90, 60-75, 40-65, and/or 15-35 percent.

As used herein, the term "biological entity" means one or more living entities including, but not limited to, plants, animals, microorganisms, prokaryotes, eukaryotes, protozoa, bacteria, mammals, yeast, *E. coli*, humans, reptile, insect, bird, amphibian, and/or fish. The animals may include, but are not limited to, domesticated, wild, research, zoo, sports, pet, primate, marine, and/or farm animals. Animals include, but are not limited to, bovine, porcine, swine, ovine, murine, canine, avian, feline, equine, and/or rodent animals. Domesticated and/or farm animals include, but are not limited to, chickens, horses, cattle, pigs, sheep, donkeys, mules, rabbits, goats, ducks, geese, chickens, and/or turkeys. Wild animals include, but are not limited to, non-human primates, bear, deer, elk, raccoons, squirrels, wolves, coyotes, opossums, foxes, skunks, and/or cougars. Research animals include, but are not limited to, rats, mice, hamsters, guinea pigs, rabbits, pigs, dogs, cats and/or non-human primates. Pets include, but are not limited to, dogs, cats, gerbils, hamsters, guinea pigs and/or rabbits. Reptiles include, but are not limited to, snakes, lizards, alligators, crocodiles, iguanas, and/or turtles. Avian animals include, but are not limited to, chickens, ducks, geese, owls, sea gulls, eagles, hawks, and/or falcons. Fish include, but are not limited to, farm-raised, wild, pelagic, coastal, sport, commercial, fresh water, salt water, and/or tropical. Marine animals include, but are not limited to, whales, sharks, seals, sea lions, walruses, penguins, dolphins, and/or fish. One or more of the genomes described herein may be part of or included in one or more biological entities.

As used herein, the term "identifying" means one or more process used to determine one or more components, wherein the one or more components optionally include, but are not limited to, one or more genomes, one or more germ line genomes, one or more chromosomal characteristics, one or more genetic characteristics, one or more single nucleotide polymorphisms, one or more haplotypes, one or more nucleic acid sequences, one or more genomes, one or more germ line cells, one or more nuclei, etc. and/or other "items" that are appropriate when read in the context in which they occur in the description. Processes include, but are not limited to, user selected, user identified, user determined, software method analysis, algorithm-based, computer mediated, operations research, optimization, simulation, queuing theory, and/or game theory. Illustrative embodiments of such processes include but are not limited to information processing, information technology, datamining, and/or database analysis.

As used herein, the term "separating" means one or more process used to partially or completely isolate from one another one or more components, and/or one or more process that result in one or more components being no longer located in the same place. The one or more components optionally include, but are not limited to, one or more genomes, one or more germ line cells, one or more nuclei, etc. and/or other components that are appropriate when read in the context in which they occur in the description. Processes include, but are not limited to, manual, automatic, semi-automatic, remote-controlled, and/or robotic. Illustrative embodiments of such processes include but are not limited to fluorescence activated cell sorting (FACS).

As used herein, the term "selecting" means one or more process used to "identify" and/or "separate" one or more components, optionally one or more reproductive components, optionally one or more germ line genomes, optionally one or more genetic characteristics. The one or more components optionally include, but are not limited to, one or more chromosomal characteristics, one or more genetic characteristics, one or more single nucleotide polymorphisms, one or more haplotypes, one or more nucleic acid sequences, one or more genomes, one or more germ line cells, one or more nuclei, etc. and/or other "items" that are appropriate when read in the context in which they occur in the description. Processes include, but are not limited to, those described above for "identifying" and/or "separating".

As used herein, the term "selecting for . . . based on" and "selecting against . . . based on" means one or more process used to "identify" and "separate" one or more components, optionally one or more reproductive components, and/or optionally one or more germ line genomes, using (or based on) defined parameters. Using (based on) defined parameters may include detecting the presence and/or absence of one or more genetic characteristics, and/or the presence or absence of a weighted combination of one or more genetic characteristics, for example. Using (based on) defined parameters may include detecting the increase and/or decrease of one or more genetic characteristics, and/or the increase or decrease of a weighted combination of one or more genetic characteristics, for example.

As used herein, "presence and/or absence" means detectable and/or not detectable based on scientific and/or economic reasonableness. Something may be detectable and/or undetectable scientifically if a signal is above background and/or below background using a scientifically appropriate assay, and/or if a signal is altered, for example increased and/or decreased, in a statistically significant manner.

As used herein, the term "increase and/or decrease" means a change or alteration (up or down as scientifically appropriate) in the level of detectability as compared with a control and/or reference level, optionally a statistically significant change in the level of detectability as compared with a control and/or reference level.

As used herein, the term "providing and/or co-localizing" means any process resulting in one or more components being in the same place at the same time. By "in the same place at the same time" is meant physical proximity such that the one or more components are capable of interaction on a molecular level. Providing may include, co-localizing, commingling, combining, mixing, assembling, aggregating, injecting, or other similar processes. Methods for providing molecules to the nucleus of living cells are known in the art and include, but are not limited to, microinjection, scrape-loading, bead-loading, osmotic lysis of pinosomes, liposome transfection, and cell permeablization (Journal of Cell Science (1987) 88:669-678; Methods (2003) 29:51-57).

Generic processes useful for co-localizing, providing and/or separating, and including sequential processes, are known in the art and include, but are not limited to, one or more of manual methods, automated or semi-automated methods, robot-controlled methods, remote-controlled methods, mechanical methods, electrical methods, computer and/or software-controlled methods, and fluid flow. Fluid flow includes, but is not limited to, nanofluidics and microfluidics. Nanofluidics and microfluidics include, but are not limited to, continuous flow microfluidics and digital microfluidics, and have been developed for use in biological systems (Annu. Rev. Fluid Mech. (2004) 36:381-411; Annu. Rev. Biomed. Eng. (2002) 4:261-86; Science (1988) 242:1162-1164, Rev. Mod. Phys. (2005) 77:977-1026).

As used herein, the term "hybridization" means one or more processes for co-localizing complementary, single-stranded nucleic acids, and/or co-localizing complementary non-traditional molecules with single- or double-stranded nucleic acids through strand separation and re-annealing, for example. In illustrative embodiments, complementary PNA and/or nucleic acid molecules, optionally oligonucleotides, may hybridize to single- or double-stranded DNA.

Methods for hybridization are known in the art, and include, but are not limited to, conditions for low and high stringency hybridization (Sambrook and Russell. (2001) *Molecular Cloning: A Laboratory Manual* 3rd edition. Cold Spring Harbor Laboratory Press; Sambrook, Fritsch, Maniatis. *Molecular Cloning: A Laboratory Manual* $3^{rd}$ edition, includes a spiral bound, 3 volume set, associated with a web site as an on-line laboratory manual. Stringency of the hybridization may be controlled (e.g. by the washing conditions) to require up to 100% complementarity between the probe and the target sequence (high stringency), or to allow some mismatches between the probe and the target sequence (low stringency). Factors to determine the appropriate hybridization and wash conditions based on the target and the probe are known in the art. In illustrative embodiments, following the first wash using 0.2×SSC/0.1% SDS for 10 minutes at 68° C., two additional washes with 0.2×SSC/0.1% SDS for 15 minutes each at 68° C. are performed for high stringency washes, two additional washes at 0.2×SSC/0.1% SDS for 15 minutes each at 42° C. for moderate stringency washes, and two additional washes 0.2×SSC/0.1% SDS for 15 minutes each at room temperature for low stringency washes.

As used herein, the term "genotyping" means one or more processes for determining the genotype of one or more biological entities. Methods of genotyping include, but are not limited to, PCR, DNA sequencing, and hybridization to DNA chips or beads. In illustrative embodiments, not intended to be in any way limiting, short tandem repeats, microsatellite DNA, mitochondrial DNA, and/or single nucleotide polymorphisms may be used for genotyping (Forensic Sci. Int. (2004) 146 suppl:S171-3; Forensic Sci. Int. (2005) 50:519-525; Forensic Sci. Int. (2005) 153:237-246; Forensic Sci. Int. (2005) 153:247-259; Forensic Sci. Int. (2005) 154:111-121; Forensic Sci. Int. (2005) 154:181-194; Forensic Sci. Int. (2005) 154:128-136; Forensic Sci. Int. (2006) 157:23-35; Int. J. Legal Med. (2005) 119:10-15; Methods Mol. Biol. (2005) 297:229-242; Electrophoresis (2005) 26:4411-4420; Leg. Med. (Tokyo) (2005) 7:259-262).

As used herein, the term "detecting" means one or more processes for measuring and/or identifying and/or documenting and/or recording the presence or absence and/or amount and/or type and/or intensity of a characteristic, for example, or as appropriate in the context used herein. Methods for detecting molecular genetic alterations are known in the art. Methods include those appropriate for viable or living cells and/or non-viable or non-living cells.

Sequences that include only one base pair change or single nucleotide polymorphism (SNP) can be detected using one or more methods described herein, and/or methods known in the art. Methods for detecting single nucleic acid transcripts, SNPs, and chromosomal abnormalities are known in the art and include, but are not limited to a variety of FISH and other fluorescent techniques (Science (1998) 280:585-590; Bio-Techniques (2006) 40:489-495). Methods for detecting large scale genetic alterations such as, but not limited to, allelic imbalance, microsatellite instability, insertions, deletions, translocations, and aberrant methylation are known in the art and include, but are not limited to, digital SNP analysis (Clinical Cancer Research (2002) 8:2580-2585).

Methods for detecting specific nucleic acid sequences in viable and/or non-viable cells and/or nuclei are known in the art and include, but are not limited to, using labeled oligonucleotides, labeled protein nucleic acid (PNA) oligonucleotides, and labeled polyamides (Current Organic Chemistry (2006) 10:491-518; Mol. Hum Reprod. (2004) 10:467-472; Mammalian Genome (2000) 11:384-391; Adv. in Genetics (2006) 56:1-51; The EMBO Journal (2003) 22: 6631-6641; Eur. J. Hum. Genetics (2003) 11:337-341; Mammalian Genome (1999) 10: 13-18; The EMBO Journal (2001) 20:3218-3228; Bioorganic & Medicinal Chem. Lett. (2003) 13:1565-1570; Nuc. Acids Res. (2004) 32:2802-2818; Thesis by T. P. Best (2005) California Institute of Technology; Methods (2003) 29:51-57). Quenched probes, such as molecular beacons and quenched auto-ligation probes, provide highly specific detection of nucleic acids, for example (Trends in Biotech. (2005) 23:225-230). Although in some instances, one or more methods are described for RNA, they can be used analogously for DNA.

Methods for imaging nucleic acid molecules, including single nucleic acid molecules, within living cells and/or living cell nuclei are known in the art, and include, but are not limited to, ultra-sensitive optical techniques for imaging fluorescent probes and/or quantum dots (Biochem. Biophys. Res. Commun. (2006) 344:772-779; Histochem. Cell Biol. (2006) 125:451-456; Trends in Cell Biol. (1998) 8:288292; Biophys. J. (2000) 78:2170-2179; Anal. Chem. (2000) 72:5606-5611; Nature (2004) 5:856-862; Science (2004) 304:1797-1800; Biomedical Optics (2005) 10:051406-1 to 051406-9). Although in some instances one or more methods are described for one type of nucleic acid, they can be used analogously for other types of nucleic acid.

As used herein, the term "decondensing" means one or more processes for decreasing and/or reversing the condensation of one or more nucleic acids with proteins, and including for example, but not limited to, decreasing the condensation of chromatin including one or more chromosomes, one or more portions of chromosomes, one or more genomes, or one or more portions of genomes. As used herein, the term "condensing and/or re-condensing" means one or more processes for increasing condensation and/or reversing the decondensation of one or more nucleic acids with proteins including, but not limited to, protamines and optionally histones, and including for example, but not limited to, increasing the condensation of chromatin including one or more chromosomes, one or more portions of chromosomes, one or more genomes, or one or more portions of genomes. In some embodiments, the terms decondensing/recondensing apply specifically to chromatin of spermatids, spermatocytes, and/or spermatozoa that has been partially or completely condensed and/or decondensed in association with protamines and optionally histones.

Methods for decondensing chromatin of spermatids, spermatocytes, and/or spermatozoa that have been partially or completely condensed in association with protamines are known in the art. Methods may be destructive and/or non-destructive of the cells, genomes, and/or nuclei, and, may result in viable or non-viable genomes. Methods for partial and/or complete decondensation include, but are not limited to, exposure to dithiothreitol, glutathione, heparin, and/or heparin sulfate, and similar reagents, and one or more of these treatments render sperm still functional for fertilization (J. Cell Science (2005) 118:1811-1820; Hum. Repro. (2005) 20:2784-2789; Theriogenology (2005) 63:783-794; J. Exp. Zool. (1999) 284:789-797; J. Biol. Chem. (2004) 279:20088-20095). Methods for partial and/or complete decondensation of one or more partially and/or completely condensed genomes include exposure to extracts from stimulated ova, exposure to stimulated ova, and/or exposure to recombinant and/or reconstituted extracts of stimulated ova. By stimulated is meant the changes that occur during fertilization.

Methods for identifying genetic characteristics in condensed, partially condensed, partially decondensed, and/or partially recondensed male germ line haploid genomes are known in the art, and non-random chromosome positioning in sperm has been established (J. Cell Science (2005) 118:1811-1820; Biol. Repro. (1993) 48:1193-1201; J. Cell Science (2005) 118:4541-4550).

As used herein, the term "fertilizing" means co-localizing two genomes in a first location such that the genomes form at least one diploid genome including genetic information from both genomes with the potential to become a viable biological entity and/or with the potential to initiate development and/or is totitpotent. In some embodiments, at least one genome is a haploid genome. In some embodiments, both genomes are haploid genomes. In some embodiments, at least one genome is a diploid genome. In some embodiments, one or more of the genomes are germ line genomes. In some embodiments, at least one genome is a male germ line genome. In some embodiments, at least one genome is a female germ line genome.

Methods for fertilization are known in the art and include, but are not limited to, intracytoplasmic injection of mature and/or immature, damaged and/or undamaged, sperm cells, nuclei, and/or genomes, including, for example, ICSI (Hum. Repro. (2002) 4:990-998; Hum. Repro. (1998) 13:117-127; Reproduction (2005) 130:907-916; Mol. Repro. & Devel. (2004) 68:96-102; Theriogenology (2005) 63:783-794).

As used herein, the term "in vitro" means performing a given action in cells or parts of cells in a controlled environment outside a living biological entity. In vitro actions may be destructive, non-destructive, at least partially destructive, or at least partially non-destructive.

As used herein, the term "destructive" means damaging to the cell or part of a cell such that it no longer is able to be used in the methods described herein, such as selecting, separating, or sorting genomes, and optionally fertilization. Unless contrary to a given context, the term destructive may refer to damage to a cell or part of a cell that that results in a partial or complete loss of viability.

As used herein, the term "non-destructive" means limiting damage to the cell or part of a cell such that it is able to be used in the methods described herein, such as selecting, separating, or sorting genomes, and optionally fertilization. Unless contrary to a given context, the term non-destructive may refer to damage to a cell or part of a cell that that results in partial or no loss of viability.

In one aspect, the disclosure is drawn to one or more methods for selecting one or more germ line genomes at least partially based on one or more genetic characteristics of one or more germ line genomes. Although one or more methods may be presented separately herein, it is intended and envisioned that one or more methods and/or embodiments of one or more methods may be combined and/or substituted to encompass the full disclosure. In some embodiments, one or more methods described herein are used to generate one or more compositions described herein, and/or are performed on one or more apparatus described herein. In some embodiments, one or more methods may include one or more operations, and using all or more computing devices and/or systems.

In some embodiments, one or more methods include hybridizing one or more probes in vitro to one or more nucleic acid sequences of one or more male germ line haploid genomes; determining one or more genetic characteristics of the one or more male germ line haploid genomes; and selecting one or more of the one or more male germ line haploid genomes based at least partially on one or more of the one or more genetic characteristics of the one or more male germ line haploid genomes.

In some embodiments, one or more methods include detecting one or more genetic characteristics of one or more male germ line haploid genomes at least partially based on methods other than binding of one or more nucleic acids of the one or more male germ line haploid genomes with a polyamide or Hoechst; and selecting one or more of the one or more male germ line haploid genomes based at least partially on the one or more genetic characteristics of the one or more male germ line haploid genomes. In some embodiments, the one or more probes do not include a polyamide.

In some embodiments, one or more methods include detecting one or more genetic characteristics of one or more male germ line haploid genomes at least partially based on sequence-specific binding to one or more nucleic acids of the one or more male germ line haploid genomes, and selecting one or more of the one or more male germ line haploid genomes based at least partially on the one or more genetic characteristics of the one or more male germ line haploid genomes.

In some embodiments, one or more methods include detecting one or more genetic characteristics of one or more male germ line haploid genomes at least partially based on using one or more probes containing one or more nucleic acid elements, and selecting one or more of the one or more male germ line haploid genomes based at least partially on the one or more genetic characteristics of the one or more male germ line haploid genomes.

In some embodiments, one or more methods include detecting one or more genetic characteristics of one or more male germ line haploid genomes at least partially based on using one or more probes that do not bind to the minor groove of DNA, and selecting one or more of the one or more male germ line haploid genomes based at least partially on the one or more genetic characteristics of the one or more male germ line haploid genomes.

In some embodiments, one or more methods include detecting one or more genetic characteristics of one or more male germ line haploid genomes at least partially based on using one or more probes that bind to the major groove of DNA, and selecting one or more of the one or more male germ line haploid genomes based at least partially on the one or more genetic characteristics of the one or more male germ line haploid genomes.

In some embodiments, one or more methods include hybridizing one or more nucleic acid sequence specific probes in vitro to the one or more nucleic acid sequences of the one or more male germ line haploid genomes. In some embodiments, one or more of the one or more probes are selected from the group consisting of a protein nucleic acid and an oligonucleotide.

In some embodiments, one or more methods include determining one or more genetic characteristics of the one or more male germ line haploid genomes at least partially based on detecting the hybridization of the one or more probes in vitro to the one or more nucleic acid sequences of the one or more male germ line haploid genomes.

In some embodiments, one or more methods further include detecting the hybridization of the one or more probes in vitro to the one or more nucleic acid sequences of the one or more male germ line haploid genomes. In some embodiments, detecting the hybridization of the one or more probes in vitro is at least partially based on the presence of a detectable marker of hybridization, the detectable marker of hybridization is optionally selected from the group consisting of quantum dots, molecular beacons, and fluorescence, including but not limited to, fluorescence resonance energy transfer (FRET), and fluorescence in situ hybridization (FISH).

In some embodiments, one or more methods further include analyzing one or more genetic characteristics of the one or more male germ line haploid genomes. In some embodiments, analyzing one or more genetic characteristics includes, but is not limited to, comparing one or more genetic characteristics of one or more male germ line haploid genomes with one or more reference and/or one or more target genetic characteristics. In some embodiments, analyzing one or more genetic characteristics includes, but is not limited to, performing a weighted analysis of one or more of the one or more male germ line haploid genomes at least partially based on a comparison with one or more reference genetic characteristics and/or one or more target genetic characteristics.

In some embodiments, one or more methods include selecting for or against one or more reference and/or one or more target genetic characteristics, and/or a weighted combination of one or more reference and/or one or more target genetic characteristics.

In some embodiments, analyzing one or more genetic characteristics of one or more male germ line haploid genomes includes analyzing optionally a weighted combination of one or more of one or more single nucleotide polymorphisms, one or more chromosomes, or one or more nucleic acid sequences of the one or more male germ line haploid genomes. In some embodiments, one or more methods include determining and/or selecting one or more reference genetic characteristics and/or the one or more target genetic characteristics at least partially based on one or more genetic characteristics of one or more female germ line genomes.

In some embodiments, one or more methods include removing, separating, and/or eliminating one or more of the one or more probes from the one or more male germ line haploid genomes and/or from one or more of the one or more nucleic acid sequences of the one or more male germ line haploid genomes.

In some embodiments, one or more male germ line haploid genomes are at least partially condensed, are part of one or more spermatozoa, and/or are at least partially isolated from one or more spermatozoa. In some embodiments, one or more male germ line haploid genomes are part of one or more spermatids, and/or are at least partially isolated from one or more spermatids.

In some embodiments, one or more genetic characteristics of one or more male germ line haploid genomes include a weighted combination of one or more of the one or more genetic characteristics. In some embodiments, one or more genetic characteristics of the one or more male germ line haploid genomes include one or more single nucleotide polymorphisms, one or more chromosomal characteristics, one or more methylation patterns, one or more DNA sequences, one or more mitochondrial nucleic acid sequences, one or more telomeric sequences, and/or one or more telomeric lengths, optionally selected from the group consisting of total genomic telomeric length, telomeric length of one or more ends of one or more chromosomes, and weighted combinations of one or more telomeric lengths of one or more chromosomes.

In some embodiments, one or more SNPs may identify one or more haplotypes to be selected for or selected against. In some embodiments, the one or more SNPs may alter one or more of one or more coding regions, one or more gene products, one or more non-coding regions, one or more intergenic regions, one or more centromeric regions, one or more telomeric regions, or one or more RNA In some embodiments, the one or more SNPs may be in linkage disequilibrium with one or more traits, one or more alleles, or one or more markers of chromosomal characteristics.

In some embodiments, one or more chromosomal characteristics may include, but are not limited to, one or more duplications, insertions, deletions, substitutions, replications or breaks. In some embodiments, the one or more duplications are of one or more chromosomes (for example, trisomy 21) and/or of portions of one or more chromosomes. In some embodiments, one or more chromosomal characteristics may include, but are not limited to, haplotype and/or nucleic acid sequence.

In some embodiments, one or more nucleic acid sequences may include, but are not limited to, repetitive sequences, telomeric sequences, centromeric sequences, mutated sequences, alternate sequences, intergenic sequences, protein coding sequences, and/or non-coding sequences. In some embodiments, the nucleic acid sequence may be linked with one or more disease or disorder, and optionally may encode a gene linked with one or more disease or disorder.

In some embodiments, one or more methods include selecting, sorting, and/or separating one or more of the one or more male germ line haploid genomes based at least partially on one or more target genetic characteristics.

In some embodiments, one or more methods include selecting, sorting, and/or separating one or more of the one or more male germ line haploid genomes based at least partially on one or more genetic characteristics of one or more female germ line genomes.

In some embodiments, one or more methods include selecting, sorting, and/or separating one or more male germ line haploid genomes based at least partially on one or more genetic characteristics of the one or more male germ line haploid genomes; and wherein at least one of the one or more genetic characteristics of the one or more male germ line haploid genomes is selected, sorted and/or separated at least partially based on one or more genetic characteristics of one or more female genomes, optionally one or more female germ line genomes, optionally one or more female germ line haploid genomes. In some embodiments, one or more methods include determining one or more genetic characteristics of one or more female genomes, optionally one or more female germ line genomes, optionally one or more female germ line haploid genomes; and selecting, separating, and/or sorting one or more male germ line haploid genomes at least partially based on the one or more genetic characteristics of the one or more female germ line genomes, optionally one or more female germ line haploid genomes.

In illustrative embodiments, determining one or more genetic characteristics of one or more female germ line genomes includes, but is not limited to, receiving an input including data representative of the one or more genetic characteristics of the one or more female germ line genomes, where the input may be sent from an external or an internal source. In some illustrative embodiments, the data representative of the one or more genetic characteristics of the one or more female germ line genomes is generated internally. In illustrative embodiments, determining one or more genetic characteristics of one or more female germ line genomes includes, but is not limited to, co-localizing, binding, and/or hybridizing one or more probes and/or one or more molecular markers with one or more nucleic acids of the one or more female germ line genomes.

In some embodiments, the one or more genetic characteristics of the one or more male germ line haploid genomes and/or the one or more female germ line genomes include one or more single nucleotide polymorphisms, one or more chromosomal characteristics, one or more methylation patterns, and/or one or more nucleic acid sequences; or a weighted combination thereof. In some embodiments, one or more genetic characteristics of one or more male germ line haploid genomes and/or female germ line genomes include one or more mitochondrial nucleic acid sequences, one or more telomeric sequences, and/or one or more telomeric lengths, or a weighted combination thereof. The one or more telomeric lengths are optionally selected from the group consisting of a total genomic telomeric length, a telomeric length of one or more ends of one or more chromosomes, and a weighted combination of one or more telomeric lengths of one or more chromosomes.

In some embodiments, one or more SNPs may identify one or more haplotypes to be selected for or selected against. In some embodiments, the one or more SNPs may alter one or more of one or more coding regions, one or more gene products, one or more non-coding regions, one or more intergenic regions, one or more centromeric regions, one or more telomeric regions, or one or more RNA In some embodiments, the one or more SNPs may be in linkage disequilibrium with one or more traits, one or more alleles, or one or more markers of chromosomal characteristics.

In some embodiments, one or more chromosomal characteristics may include, but are not limited to, one or more duplications, insertions, deletions, substitutions, replications or breaks. In some embodiments, the one or more duplications are of one or more chromosomes (for example, trisomy 21) and/or of portions of one or more chromosomes. In some embodiments, one or more chromosomal characteristics may include, but are not limited to, haplotype and/or nucleic acid sequence.

In some embodiments, one or more nucleic acid sequences may include, but are not limited to, repetitive sequences, telomeric sequences, centromeric sequences, mutated sequences, alternate sequences, intergenic sequences, protein coding sequences, and/or non-coding sequences. In some embodiments, the nucleic acid sequence may be linked with one or more disease or disorder, and optionally may encode a gene linked with one or more disease or disorder.

In some embodiments, the one or more genetic characteristics of one or more male germ line haploid genomes and/or one or more female germ line genomes include a weighted combination of the one or more genetic characteristics, optionally including a weighted combination of one or more of one or more single nucleotide polymorphisms, one or more chromosomal characteristics, one or more methylation patterns and/or one or more nucleic acid sequences.

In some embodiments, one or more methods include using the selected one or more male germ line haploid genomes to fertilize one or more eggs containing one or more female germ line genomes. In some embodiments, one or more methods include providing and/or co-localizing the selected one or more male germ line haploid genomes to and/or with the one or more female germ line genomes. In some embodiments, the one or more female germ line genomes are one or more haploid genomes.

In some embodiments, one or more methods further include determining the one or more genetic characteristics of the one or more male germ line haploid genomes and/or the one or more female germ line genomes. In some embodiments, determining the one or more genetic characteristics of the one or more genomes includes detecting one or more nucleic acid sequences of the one or more genomes optionally using one or more polyamides and/or one or more protein nucleic acids.

In some embodiments, determining the one or more genetic characteristics of the one or more male germ line haploid genomes and/or the one or more female germ line genomes includes co-localizing, optionally binding, optionally hybridizing, optionally in vitro, one or more probes and/or one or more molecular markers to one or more nucleic acid sequences of one or more of the one or more genomes. In some embodiments, the one or more probes are one or more nucleic acid specific probes, optionally selected from the group consisting of oligonucleotide, protein nucleic acid, and polyamide.

In some embodiments, determining one or more of the one or more genetic characteristics of the one or more male germ line haploid genomes and/or one or more female germ line genomes is at least partially based on detecting the association, optionally the binding, optionally the hybridization, of the one or more probes and/or one or more molecular markers with the one or more nucleic acid sequences of the one or more genomes.

In some embodiments, one or more methods includes detecting the association, binding, and/or hybridization of the one or more probes and/or one or more molecular markers to the one or more nucleic acid sequences of the one or more male germ line haploid genomes and/or one or more female germ line genomes, optionally by detecting the association, binding, and/or hybridization of the one or more probes based on the presence of a detectable marker of hybridization, the detectable marker of hybridization selected from the group consisting of quantum dots, molecular beacons, and fluorescence, including FRET and/or FISH.

In some embodiments, one or more methods include separating the selected one or more male germ line haploid genomes. In some embodiments, one or more methods include using the selected one or more male germ line haploid genomes to fertilize at least one of the one or more female germ line genomes. In some embodiments, one or more methods include providing and/or co-localizing the selected one or more male germ line haploid genomes to and/or with at least one of the one or more female germ line genomes.

In some embodiments, one or more methods further include analyzing the one or more genetic characteristics of one or more male germ line haploid genomes and/or one or more female germ line genomes. In some embodiments, analyzing one or more genetic characteristics of one or more genomes comprises comparing one or more genetic characteristics of the one or more genomes with one or more reference genetic characteristics and/or target genetic characteristics. In some embodiments, one or more methods include determining, and/or selecting, one or more of the one or more reference genetic characteristics or the one or more target genetic characteristics at least partially based on one or more genetic characteristics of one or more female germ line genomes and/or male germ line genomes. In some embodiments, the one or more reference genetic characteristics and/or target genetic characteristics, and/or a weighted combination thereof, may be selected for or selected against. In some embodiments, analyzing the one or more genetic characteristics of the one or more genomes comprises analyzing one or more single nucleotide polymorphisms, one or more chromosomes, one or more methylation patterns and/or one or more nucleic acid sequences of the one or more genomes.

In some embodiments, the one or more male germ line haploid genomes are part of one or more spermatids, spermatocytes, or spermatozoa. In some embodiments, the one or more male germ line haploid genomes are isolated from one or more spermatids, spermatocytes, or spermatozoa. In some embodiments, the one or more male germ line haploid genomes are at least partially condensed. In some embodiments, the one or more male germ line haploid genomes are from one or more biological entities.

In some embodiments, the one or more female germ line genomes are part of and/or at least partially isolated from one or more of polar bodies, oogonia, or ova. In some embodiments, the one or more female germ line genomes are from one or more biological entities.

In some embodiments, one or more methods include decondensing one or more male germ line haploid genomes; determining one or more genetic characteristics of the one or more male germ line haploid genomes; and selecting, separating, and/or sorting one or more of the one or more male germ line haploid genomes based at least partially on the one or more genetic characteristics of the one or more male germ line haploid genomes.

In some embodiments, one or more male germ line haploid genomes are part of one or more condensed spermatocytes or one or more spermatozoa, and/or are at least partially isolated from one or more condensed spermatocytes or one or more spermatozoa. In some embodiments, one or more male germ line haploid genomes are from one or more biological entities.

In some embodiments, one or more methods include at least partially decondensing one or more male germ line haploid genomes. In some embodiments, one or more methods include decondensing in vitro one or more of the one or more male germ line haploid genomes, optionally by providing one or more reducing agents. In some embodiments, one or more methods include providing one or more reducing agents to one or more of the one or more male germ line haploid genomes. In some embodiments, one or more methods include providing one or more molecular markers to one or more of the one or more male germ line haploid genomes, optionally to one or more decondensed male germ line haploid genomes.

In some embodiments, determining one or more genetic characteristics of the one or more male germ line haploid genomes includes co-localizing, binding, and/or hybridizing, optionally in vitro, one or more, optionally nucleic acid specific, probes and/or with one or more nucleic acid sequences of one or more male germ line haploid genomes.

In some embodiments, determining one or more genetic characteristics of the one or more male germ line haploid genomes includes detecting one or more nucleic acid sequences of the one or more male germ line haploid genomes. In some embodiments, detecting one or more nucleic acid sequences of the one or more male germ line haploid genomes includes detecting one or more molecular markers and/or probes of the one or more nucleic acid sequences of the one or more male germ line haploid genomes. In some embodiments, the one or more molecular markers and/or probes are associated with, bound, and/or hybridized to the one or more nucleic acid sequences of the one or more male germ line haploid genomes.

In some embodiments, determining one or more genetic characteristics of the one or more male germ line haploid genomes includes receiving data representative of the one or more genetic characteristics and/or one or more nucleic acid sequences of the one or more male germ line haploid genomes. Insane embodiments, receiving data may be from an internal and/or an external source and/or input. In some embodiments, determining one or more genetic characteristics of the one or more male germ line haploid genomes includes analyzing the one or more genetic characteristics of the one or more male germ line haploid genomes.

In some embodiments, one or more methods include co-localizing, binding, and/or hybridizing one or more molecular markers and/or probes with one or more nucleic acid sequences of the one or more male germ line haploid genomes.

In some embodiments, one or more methods include detecting one or more nucleic acid sequences of the one or more male germ line haploid genomes.

In some embodiments, one or more methods include analyzing the one or more genetic characteristics of the one or more male germ line haploid genomes. In some embodiments, analyzing the one or more genetic characteristics of the one or more male germ line haploid genomes includes analyzing one or more single nucleotide polymorphisms, one or more chromosomes, one or more methylation patterns, and/or one or more nucleic acid sequences of the one or more male germ line haploid genomes.

In some embodiments, analyzing the one or more genetic characteristics of the one or more male germ line haploid genomes includes comparing the one or more genetic characteristics of one or more male germ line haploid genomes with, optionally a weighted combination of, one or more reference genetic characteristics and/or one or more target genetic characteristics. In some embodiments, the method includes selecting for one or more male germ line haploid genomes with one or more reference genetic characteristics and/or the one or more target genetic characteristics and/or with a weighted combination of one or more reference genetic characteristics and/or one or more target genetic characteristics. In some embodiments, the method includes selecting against one or more male germ line haploid genomes with one or more reference genetic characteristics and/or the one or more target genetic characteristics and/or with a weighted combination of one or more reference genetic characteristics and/or one or more target genetic characteristics.

In some embodiments, one or more methods further include determining and/or selecting one or more reference genetic characteristics and/or the one or more target genetic characteristics at least partially based on one or more genetic characteristics of one or more female germ line genomes. In some embodiments, selecting one or more male germ line haploid genomes includes selecting one or more male germ line haploid genomes at least partially based on one or more genetic characteristics of one or more female germ line genomes.

In some embodiments, one or more methods include separating and/or sorting the selected one or more male germ line haploid genomes. In some embodiments, one or more methods include providing and/or co-localizing the one or more male haploid genomes with one or more female germ line genomes.

In some embodiments, one or more methods include determining one or more genetic characteristics of one or more related spermatid genomes; and selecting, separating, and/or sorting one or more related spermatid genomes based at least partially on one or more genetic characteristics of one or more related spermatid genomes.

In some embodiments, one or more related spermatid genomes are from one or more biological entities in some embodiments, one or more related spermatid genomes are at least partially isolated from one or more spermatids, and/or are part of one or more spermatids.

In some embodiments, determining one or more genetic characteristics of one or more related spermatid genomes includes subtractively determining one or more genetic characteristics of one or more related spermatid genomes. In some embodiments, subtractively determining one or more genetic characteristics of one or more related spermatid genomes includes determining one or more genetic characteristics of one, two, or three of the one or more related spermatid genomes; and comparing one or more genetic characteristics of one, two, or three of the one or more related spermatid genomes with one or more genetic characteristics of a related diploid genome.

In illustrative embodiments, one or more methods include determining one or more genetic characteristics of one or more related spermatids by determining one or more genetic characteristics of three of the related spermatids, and through a comparative process, determining the one or more genetic characteristics of the fourth related spermatid. In some illustrative embodiments, the comparative process is a subtractive process, where the one or more genetic characteristics of the three related spermatids are compared with the one or more genetic characteristics of the related diploid genomes. The genetic characteristics of the related diploid genomes may be known, or may be determined by sequencing and/or haplotyping, for example.

In some embodiments, determining one or more genetic characteristics of one or more related spermatid genomes includes determining, optionally destructively, one or more genetic characteristics of one or more related diploid genomes, optionally of three related spermatid genomes, optionally of two related spermatid genomes, and/or optionally of one related spermatid genome.

In some embodiments, determining one or more genetic characteristics of one or more related spermatid genomes includes amplifying, optionally destructively, one or more nucleic acid sequences of the one or more related spermatid genomes and/or one or more related diploid genomes. In some embodiments, amplifying one or more nucleic acid sequences of the one or more related spermatid genomes includes amplifying in vitro or in situ the one or more nucleic acid sequences of the one or more related spermatid genomes.

In some embodiments, determining one or more genetic characteristics of one or more related spermatid genomes includes sequencing, optionally destructively, one or more nucleic acids of one or more related diploid genomes and/or one or more related spermatid genomes. In some embodiments, sequencing one or more nucleic acids of the one or more related spermatid genomes includes sequencing in vitro or in situ the one or more nucleic acids of the one or more related spermatid genomes.

In some embodiments, determining one or more genetic characteristics of one or more related spermatid genomes includes co-localizing, binding, and/or hybridizing, optionally destructively, one or more probes and/or one or more molecular markers, optionally nucleic acid sequence specific probes, to one or more nucleic acid sequences of the one or more related spermatid genomes. In some embodiments, co-localizing, binding, and/or hybridizing one or more probes and/or one or more molecular markers to one or more nucleic acid sequences of the one or more related spermatid genomes includes co-localizing, binding, and/or hybridizing one or more probes and/or one or more molecular markers in vitro or in situ to the one or more nucleic acid sequences of the one or more related spermatid genomes.

In some embodiments, determining the one or more genetic characteristics of the one or more related spermatid genomes includes detecting and/or identifying one or more nucleic acid sequences of the one or more related spermatid genomes. In some embodiments, detecting and/or identifying one or more nucleic acid sequences of the one or more related spermatid genomes includes detecting and/or identifying one or more markers of the one or more nucleic acid sequences of the one or more related spermatid genomes, detecting and/or identifying one or more probes associated, bound, and/or hybridized to the one or more nucleic acid sequences of the one or more related spermatid genomes.

In some embodiments, determining one or more genetic characteristics of one or more related spermatid genomes includes receiving data representative of the one or more genetic characteristics of the one or more related spermatid genomes and/or one or more related diploid genomes. In some embodiments, receiving data representative of the one or more genetic characteristics of the one or more related spermatid genomes and/or one or more related diploid genomes includes receiving data representative of one or more nucleic acid sequences of the one or more related spermatid genomes and/or one or more related diploid genomes. In some embodiments, receiving data may include receiving data from one or more internal and/or external sources and/or inputs.

In some embodiments, determining one or more genetic characteristics of one or more related spermatid genomes includes analyzing the one or more genetic characteristics of the one or more related spermatid genomes and/or one or more related diploid genomes.

In some embodiments, one or more methods include sequencing one or more nucleic acids of the one or more related spermatid genomes and/or one or more related diploid genomes. In some embodiments, one or more methods include co-localizing, binding, and/or hybridizing one or more molecular markers and/or one or more probes with one or more nucleic acid sequences of the one or more related spermatid genomes and/or one or more related diploid genomes. In some embodiments, one or more methods include detecting and/or identifying one or more nucleic acid sequences of the one or more related spermatid genomes and/or one or more related diploid genomes.

In some embodiments, one or more methods include analyzing the one or more genetic characteristics of the one or more related spermatid genomes and/or one or more related diploid genomes. In some embodiments, analyzing the one or more genetic characteristics of the one or more related spermatid genomes includes analyzing one or more single nucleotide polymorphisms, one or more chromosomes, one or more methylation patterns, and/or one or more nucleic acid sequences of the one or more related spermatid genomes and/or one or more related diploid genomes.

In some embodiments, determining one or more genetic characteristics of one or more related spermatid genomes at least partially based on the one or more genetic characteristics of one or more related spermatid genomes includes deducing and/or identifying the one or more genetic characteristics of the one or more related spermatid genomes at least partially based on the one or more genetic characteristics of one or more of the one or more related spermatid genomes and/or one or more related diploid genomes.

In some embodiments, analyzing the one or more genetic characteristics of the one or more related spermatid genomes includes comparing the one or more genetic characteristics of the one or more related spermatid genomes with one or more reference genetic characteristics and/or one or more target genetic characteristics, and/or with a weighted combination of one or more reference genetic characteristics and/or one or more target genetic characteristics. In some embodiments, one or more methods include determining and/or selecting one or more reference genetic characteristics and/or the one or more target genetic characteristics at least partially based on one or more genetic characteristics of one or more female genomes optionally one or more female germ line genomes, and/or one or more male genomes, optionally are or more male germ line genomes.

In some embodiments, comparing the one or more genetic characteristics of the one or more related spermatid genomes with one or more reference genetic characteristics and/or one or more target genetic characteristics includes selecting for and/or against one or more related spermatid genomes at least partially based on the presence of one or more reference genetic characteristics and/or one or more target genetic characteristics, and/or the presence of a weighted combination of one or more reference genetic characteristics and/or one or more target genetic characteristics.

In some embodiments, selecting one or more related spermatid genomes includes selecting, sorting, and/or separating one or more related spermatid genomes at least partially based on one or more genetic characteristics of one or more female germ line genomes. In some embodiments, selecting one or more related spermatid genomes at least partially based on one or more genetic characteristics of one or more female germ line genomes includes selecting for and/or against one or more of the one or more related spermatid genomes at least partially based on one or more genetic characteristics of one or more female germ line genomes.

In some embodiments, one or more methods further include separating and/or sorting the selected one or more related spermatid genomes. In some embodiments, one or more methods further include co-localizing and/or providing one or more of the one or more related spermatid genomes with one or more female germ line genomes.

In some embodiments, one or more methods include determining one or more genetic characteristics of one or more related polar body genomes; and selecting, sorting, and/or separating one or more related female germ line genomes based at least partially on the one or more genetic characteristics of the one or more related polar body genomes.

In some embodiments, one or more related polar body genomes and/or one or more related female germ line genomes are from one or more biological entities. In some embodiments, one or more related polar body genomes are at least partially isolated from one or more polar bodies and/or are part of one or more polar bodies. In some embodiments, one or more related polar body genomes are one or more first polar body genomes and/or one or more second polar body genomes.

In some embodiments, one or more related female germ line genomes are at least partially isolated from one or more cells and/or are part of one or more cells. In some embodiments, one or more of the one or more related female germ line genomes are at least partially isolated from one or more ova, and/or are part of one or more ova. In some embodiments, one or more related female germ line genomes are at least partially isolated from one or more related polar bodies and/or are part of one or more related polar bodies.

In some embodiments, one or more methods further include determining one or more genetic characteristics of one or more related female germ line genomes. In some embodiments, determining one or more genetic characteristics of one or more related female germ line genomes includes, but is not limited to, determining one or more genetic characteristics of one or more related polar body genomes. In some embodiments, determining one or more genetic characteristics of one or more related female germ line genomes includes, but is not limited to, subtractively determining one or more genetic characteristics of one or more related female germ line genomes. In some embodiments, subtractively determining one or more genetic characteristics of one or more related female germ line genomes includes, but is not limited to, determining one or more genetic characteristics of one, two or three related polar body genomes; and comparing the one or more genetic characteristics of one, two or three related polar body genomes with one or more one or more genetic characteristics of a related diploid genome. In some embodiments, the one or more one or more genetic characteristics of a related diploid genome are already determined and/or known, or are determined by sequencing and/or haplotyping, for example.

In illustrative embodiments, one or more methods include determining one or more genetic characteristics of one or more related female germ line genomes by determining one or more genetic characteristics of three of the related polar body genomes, and through a comparative process, determining the one or more genetic characteristics of the fourth related female germ line haploid genome. In illustrative embodiments, one or more methods include determining one or more genetic characteristics of one or more related female germ line genomes by determining one or more genetic characteristics of two of the related polar body genomes, and through a comparative process, at least partially determining one or more of the one or more genetic characteristics of the related female germ line diploid genome. In some illustrative embodiments, the comparative process is a subtractive process, where the one or more genetic characteristics of the two or three related polar body genomes are compared with the one or more genetic characteristics of the related diploid genomes.

In some embodiments, determining, optionally destructively, one or more genetic characteristics of one or more related polar body genomes includes determining one or more genetic characteristics of one or more related diploid genomes, of optionally three related polar body genomes, of optionally two related polar body genomes, and/or of optionally one related polar body genome.

In some embodiments, determining one or more genetic characteristics of one or more related polar body genomes includes amplifying, optionally destructively, one or more nucleic acid sequences of the one or more related polar body genomes and/or one or more related diploid genomes. In some embodiments, amplifying one or more nucleic acid sequences of the one or more related polar body genomes includes, amplifying in vitro and/or in situ the one or more nucleic acid sequences of the one or more related polar body genomes.

In some embodiments, determining one or more genetic characteristics of one or more related polar body genomes includes sequencing, optionally destructively, one or more nucleic acids of the one or more related polar body genomes and/or one or more related diploid genomes. In some embodiments, sequencing one or more nucleic acids of the one or more related polar body genomes includes sequencing in vitro and/or in situ the one or more nucleic acids of the one or more related polar body genomes.

In some embodiments, determining one or more genetic characteristics of one or more related polar body genomes includes co-localizing, binding, and/or hybridizing, optionally destructively, one or more probes and/or one or more molecular markers to one or more nucleic acid sequences of the one or more related polar body genomes and/or one or more related diploid genomes. In some embodiments, co-localizing, binding, and/or hybridizing one or more probes and/or one or more molecular markers to one or more nucleic acid sequences of the one or more related polar body genomes includes hybridizing the one or more probes and/or molecular markers, optionally nucleic acid sequence specific probes, in vitro and/or in situ to the one or more nucleic acid sequences of the one or more related polar body genomes.

In some embodiments, determining the one or more genetic characteristics of the one or more related polar body genomes includes detecting, and/or identifying optionally destructively, one or more nucleic acid sequences of the one or more related polar body genomes and/or one or more related diploid genomes. In some embodiments, detecting and/or identifying one or more nucleic acid sequences of the one or more related polar body genomes includes detecting and/or identifying one or more markers of the one or more nucleic acid sequences, and/or one or more probes and/or one or more molecular markers co-localized, bound, and/or hybridized to the one or more nucleic acid sequences of the one or more related polar body genomes.

In some embodiments, determining one or more genetic characteristics of one or more related polar body genomes includes receiving data representative of the one or more genetic characteristics and/or one or more nucleic acid sequences of the one or more related polar body genomes and/or one or more related diploid genomes. In some embodiments, receiving data includes receiving data from one or more internal and/or external sources and/or inputs.

In some embodiments, determining one or more genetic characteristics of one or more related polar body genomes includes analyzing the one or more genetic characteristics of the one or more related polar body genomes and/or one or more related diploid genomes. In some embodiments, determining one or more genetic characteristics of one or more related female germ line genomes at least partially based on the genetic characteristics of one or more of the one or more related polar body genomes includes deducing and/or identifying the one or more genetic characteristics of the one or more related female germ line genomes at least partially based on the genetic characteristics of one or more of the one or more related polar body genomes and/or one or more related diploid genomes.

In some embodiments, one or more methods include sequencing one or more nucleic acids of the one or more related polar body genomes and/or one or more related diploid genomes. In some embodiments, one or more methods include co-localizing, binding, and/or hybridizing one or more molecular markers and/or one or more probes with one or more nucleic acid sequences of the one or more related polar body genomes and/or one or more related diploid genomes. In some embodiments, one or more methods include detecting and/or identifying one or more nucleic acid sequences of the one or more related polar body genomes and/or one or more related diploid genomes.

In some embodiments, one or more methods include analyzing the one or more genetic characteristics of the one or more related polar body genomes and/or one or more related diploid genomes. In some embodiments, analyzing the one or more genetic characteristics of the one or more related polar body genomes includes analyzing one or more single nucleotide polymorphisms, one or more chromosomes, one or more methylation patterns, and/or one or more nucleic acid sequences of the one or more related polar body genomes and/or one or more related diploid genomes.

In some embodiments, analyzing the one or more genetic characteristics of the one or more related polar body genomes includes comparing the one or more genetic characteristics of the one or more related polar body genomes with one or more reference genetic characteristics and/or one or more target genetic characteristics, and/or with a weighted combination of one or more reference genetic characteristics and/or one or more target genetic characteristics. In some embodiments, one or more methods include determining and/or selecting one or more reference genetic characteristics and/or one or more target genetic characteristics at least partially based on one or more genetic characteristics of one or more male genomes optionally one or more male germ line genomes and/or one or more female genomes optionally female germ line genomes.

In some embodiments, comparing the one or more genetic characteristics of the one or more related female germ line genomes with one or more reference genetic characteristics and/or one or more target genetic characteristics includes selecting for and/or against one or more related female germ line genomes at least partially based on the presence of one or more reference genetic characteristics and/or the one or more target genetic characteristics, and/or the presence of a weighted combination of one or more reference genetic characteristics and/or the one or more target genetic characteristics.

In some embodiments, selecting one or more related female germ line genomes includes selecting, sorting, and/or separating one or more related female germ line genomes at least partially based on one or more genetic characteristics of one or more male germ line haploid genomes. In some embodiments, one or more methods include separating the selected one or more related female germ line genomes. In some embodiments, one or more methods include co-localizing one or more of the one or more related female germ line genomes with one or more male germ line haploid genomes. In some embodiments, one or more methods include providing one or more of the one or more related female germ line genomes to one or more male germ line haploid genomes.

In one aspect, the disclosure is drawn to one or more compositions comprising one or more germ line genomes. In some embodiments, one or more compositions are generated using one or more of the methods described herein and/or one or more of the apparatus described herein, and/or one of the systems described herein.

In some embodiments, one or more compositions include one or more containers including one or more male germ line haploid genomes, the one or more male germ line haploid genomes selected at least partially based on one or more genetic characteristics of the one or more male germ line haploid genomes, the one or more genetic characteristics of the one or more male germ line haploid genomes selected at least partially based on one or more genetic characteristics of one or more female germ line genomes.

In some embodiments, one or more compositions include one or more containers including one or more at least partially decondensed male germ line haploid genomes, the one or more male germ line haploid genomes selected at least partially based on one or more genetic characteristics of the one or more male germ line haploid genomes. In some embodiments, one or more male germ line haploid genomes are selected at least partially based on one or more genetic characteristics of the one or more male germ line haploid genomes, the one or more genetic characteristics of the one or more male germ line haploid genomes selected at least partially based on one or more genetic characteristics of one or more female germ line genomes. In some embodiments, one or more of the at least partially decondensed male germ line haploid genomes is at least partially recondensed.

In some embodiments, one or more compositions include one or more containers including one or more related spermatid genomes, the one or more male germ line haploid genomes selected at least partially based on one or more genetic characteristics of one or more related spermatid genomes. In some embodiments, the one or more related spermatid genomes are selected at least partially based on one or more of the one or more genetic characteristics of the one or more related spermatid genomes, the one or more genetic characteristics of the one or more related spermatid genomes selected at least partially based on one or more genetic characteristics of one or more female germ line genomes.

In some embodiments, one or more compositions include one or more containers including one or more female germ line haploid genomes, the one or more female germ line haploid genomes selected at least partially based on one or more genetic characteristics of one or more related polar body genomes. In some embodiments, the one or more female germ line haploid genomes are selected at least partially based on the one or more genetic characteristics of the one or more related polar body genomes, the one or more genetic characteristics of the one or more related polar body genomes selected at least partially based on one or more genetic characteristics of one or more male germ line genomes. In some embodiments, the one or more male germ line genomes are one or more male haploid germ line genomes.

In some embodiments, one or more compositions include one or more containers including one or more female germ line haploid genomes, the one or more female germ line haploid genomes selected at least partially based on one or more genetic characteristics of one or more male germ line genomes. In some embodiments, the one or more male germ line genomes are one or more male haploid germline genomes.

In one aspect, the disclosure is drawn to one or more apparatus for selecting one or more germ line genomes at least partially based on one or more genetic characteristics of one or more germ line genomes. In some embodiments, one or more of the methods described herein may be performed on one or more apparatus. In some embodiments, one or more of the compositions described herein may be created using one or more apparatus. In some embodiments, one or more system methods may be performed on one or more apparatus, and/or one or more apparatus may include one or more system or computing devices described herein.

Figure 15:
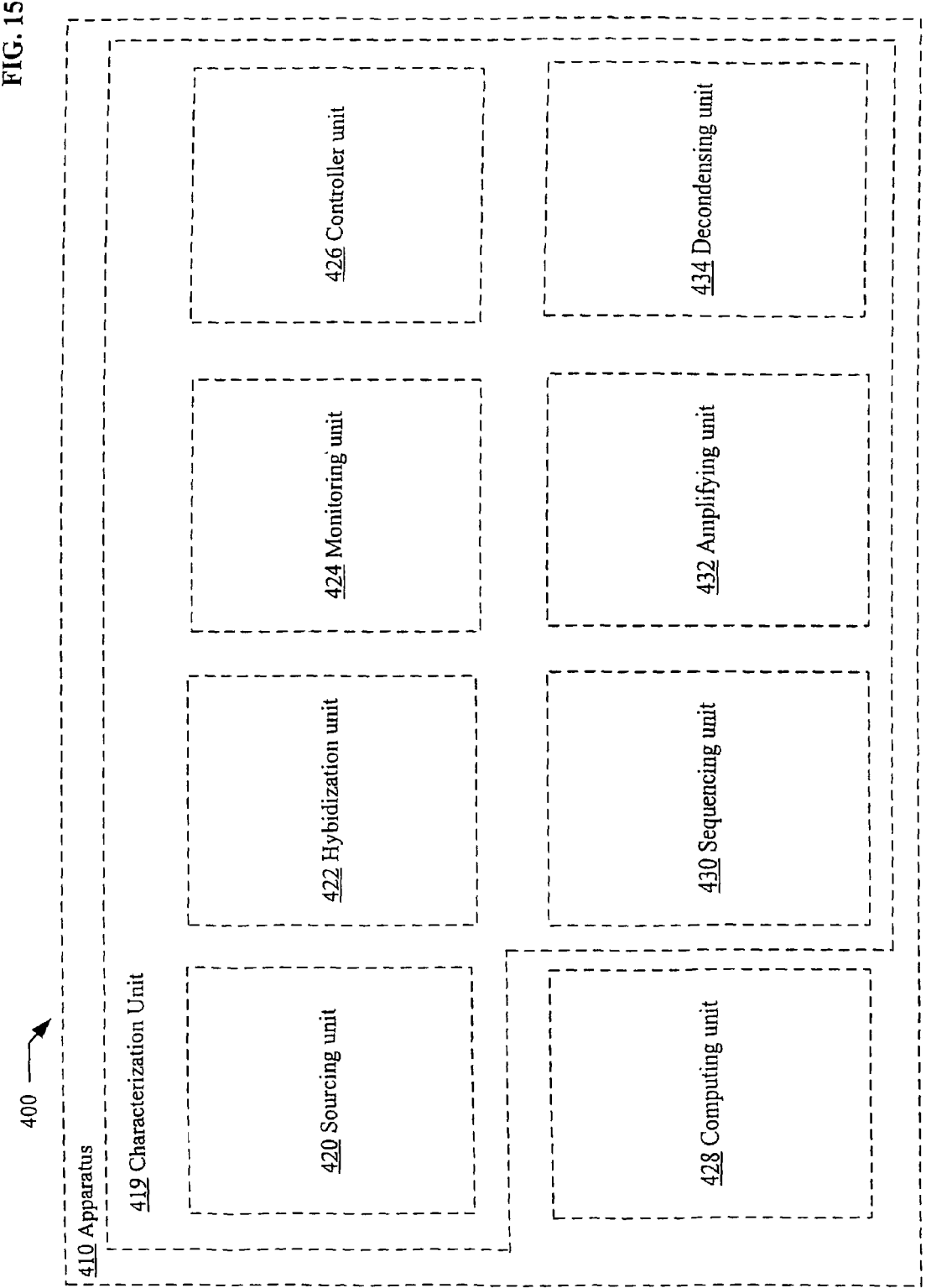
FIG. 15 shows a schematic of an illustrative apparatus in which embodiments may be implemented.

FIG. 15 shows a schematic 400 of an illustrative apparatus 410 in which embodiments may be implemented. The apparatus 410 is optionally operable for characterizing, monitoring, detecting, hybridizing, amplifying, sequencing, identifying, analyzing, and/or determining one or more genetic characteristics of one or more germ line genomes, as well as optionally selecting, separating, sorting, providing, and/or co-localizing one or more germ line genomes. The apparatus may optionally be, or include, one or more units including, but not limited to, one or more characterization units 419, one or more sourcing units 420, one or more hybridization units 422, one or more monitoring units 424, one or more controller units 426, one or more computing units 428, one or more sequencing units 430, one or more amplifying units 432, and/or one or more decondensing units 434. In some embodiments, one or more of the units may be internal or external to the apparatus. In some embodiments, one or more of the units may be part of or separate from the apparatus.

In some embodiments, one or more characterization units 419 are operable to characterize one or more genetic characteristics of one or more genomes. In some embodiments, one or more characterization units 419 include and/or are the same as, one or more of one or more sourcing units 420, one or more hybridization units 422, one or more monitoring units 424, one or more controller units 426, one or more computing units 428, one or more sequencing units 430, one or more amplifying units 432, and/or one or more decondensing units 434.

In some embodiments, one or more apparatus 410 further includes one or more fluid flows. In some embodiments, the one or more fluid flows connect and/or allow the transfer of one or more germ line genomes as well as other components, including but not limited to probes and molecular markers, among one or more of the optional one or more units of the apparatus 410. In some embodiments, the one or more fluid flows are operable to provide; co-localize, remove and/or separate, optionally sequentially, one or more germ line genomes as well as other components. In some embodiments, the one or more fluid flows are operable to provide, co-localize, remove and/or separate, optionally sequentially, one or more germ line genomes as well as other components at one or more identifiable time intervals.

In some embodiments, one or more apparatus 410 includes one or more sourcing units 420 including one or more first sources of one or more male germ line haploid genomes and one or more second sources of one or more probes; one or more hybridization units 422 operable to co-localize one or more of the one or more probes with one or more nucleic acids of the one or more male germ line haploid genomes; one or more monitoring units 424 operable to detect one or more of the one or more probes hybridized to the one or more nucleic acids of the one or more male germ line haploid genomes; and one or more controller units 426 operable to select, sort, and/or separate one or more of the one or more male germ line haploid genomes at least partially based on the detection of one or more of the one or more probes hybridized to the one or more nucleic acids.

In some embodiments, one or more apparatus 410 includes one or more sourcing units 420 including one or more first sources of one or more male germ line haploid genomes and one or more second sources of one or more probes; one or more hybridization units 422 operable to co-localize one or more of the one or more probes with one or more nucleic acids of the one or more male germ line haploid genomes; one or more monitoring units 424 operable to detect one or more of the one or more probes hybridized to the one or more nucleic acids of the one or more male germ line haploid genomes; and one or more computing units 428 operable to determine the one or more male germ line haploid genomes to select, sort, and/or separate at least partially based on the detection of one or more of the one or more probes hybridized to the one or more nucleic acids.

In some embodiments, one or more apparatus 410 includes one or more first sources of one or more male germ line haploid genomes; one or more second sources of one or more probes; one or more monitors for detecting one or more of the one or more probes; one or more units for hybridizing one or more of the one or more probes with one or more nucleic acids of the one or more male germ line haploid genomes; and one or more controllers for selecting one or more of the one or more male germ line haploid genomes at least partially based on the detection of one or more of the one or more probes hybridized to the one or more nucleic acids.

In some embodiments, one or more apparatus 410 includes one or more detecting units operable to identify one or more genetic characteristics of one or more male germ line haploid genomes using one or more nucleic acid detecting molecules other than a polyamide or Hoechst; one or more first sourcing units containing one or more sources of one or more male germ line haploid genomes; one or more second sourcing units containing one or more sources of the one or more nucleic acid detecting molecules; and one or more first controller units operable to select one or more of the one or more male germ line haploid genomes at least partially based on the one or more genetic characteristics of the one or more male germ line haploid genomes.

In some embodiments, one or more apparatus includes one or more characterization units operable to detect and/or identify one or more probes hybridized to one or more nucleic acid sequences of one or more male germ line haploid genomes; and one or more controller units operable to select, sort, and/or separate one or more of the one or more male germ line haploid genomes at least partially based on the detection and/or identification of one or more probes hybridized to one or more nucleic acid sequences. In some embodiments, one or more apparatus includes one or more characterization units operable to detect and/or identify one or more probes hybridized to one or more nucleic acid sequences of one or more male germ line haploid genomes; and one or more computing units operable to determine the one or more male germ line haploid genomes to select, sort, and/or separate at least partially based on the detection and/or identification of one or more probes hybridized to one or more nucleic acid sequences.

In some embodiments, one or more apparatus 410 includes one or more sourcing units 420 including one or more first sources of one or more male germ line haploid genomes; one or more monitoring units 424 operable to detect one or more genetic characteristics of the one or more male germ line haploid genomes; one or more computing units 428 operable to receive one or more inputs, the one or more inputs including data representative of one or more genetic characteristics of one or more female germ line genomes; one or more controller units 426 operable to select, sort, and/or separate one or more of the one or more male germ line haploid genomes at least partially based on the one or more genetic characteristics of the one or more female germ line genomes.

In some embodiments, one or more apparatus 410 includes one or more sourcing units 420 including one or more first sources of one or more male germ line haploid genomes; one or more monitoring units 424 operable to detect one or more genetic characteristics of the one or more male germ line haploid genomes; one or more computing units 428 operable to receive one or more inputs, the one or more inputs including data representative of one or more genetic characteristics of one or more female germ line genomes; and operable to determine the one or more male germ line haploid genomes to select, sort, and/or separate at least partially based on the one or more genetic characteristics of the one or more female germ line genomes.

In some embodiments, one or more apparatus 410 includes one or more first sources of one or more male germ line haploid genomes; one or more monitors for detecting one or more genetic characteristics of the one or more male germ line haploid genomes; one or more units for receiving one or more inputs, the one or more inputs including data representative of one or more genetic characteristics of one or more female germ line genomes; one or more controllers for selecting one or more of the one or more male germ line haploid genomes at least partially based on the one or more genetic characteristics of the one or more female germ line genomes.

In some embodiments, one or more apparatus 410 includes one or more characterization units 419 operable to detect and/or identify one or more genetic characteristics of one or more male germ line haploid genomes; one or more computing units 428 operable to receive one or more inputs, the one or more inputs including data representative of one or more genetic characteristics of one or more female germ line genomes; and one or more controller units 426 operable to select, sort, and/or separate one or more of the one or more male germ line haploid genomes at least partially based on the one or more genetic characteristics of the one or more female germ line genomes. In some embodiments, one or more apparatus 410 includes one or more characterization units 419 operable to detect and/or identify one or more genetic characteristics of one or more male germ line haploid genomes; one or more computing units 428 operable to receive one or more inputs, the one or more inputs including data representative of one or more genetic characteristics of one or more female germ line genomes; and operable to determine the one or more male germ line haploid genomes to select, sort, and/or separate at least partially based on the one or more genetic characteristics of the one or more female germ line genomes.

In some embodiments, one or more apparatus 410 includes one or more computing units 428 operable to receive one or more inputs, the one or more inputs including data representative of one or more genetic characteristics of one or more female germ line genomes; and one or more controller units 426 operable to select, sort, and/or separate one or more of the one or more male germ line haploid genomes at least partially based on the one or more genetic characteristics of the one or more female germ line genomes. In some embodiments, one or more apparatus 410 includes one or more computing units 428 operable to receive one or more inputs, the one or more inputs including data representative of one or more genetic characteristics of one or more female germ line genomes; and operable to determine the one or more male germ line haploid genomes to select, sort, and/or separate at least partially based on the one or more genetic characteristics of the one or more female germ line genomes.

In some embodiments, one or more apparatus 410 includes one or more sourcing units 420 including one or more first sources of one or more male germ line haploid genomes, the one or more male germ line haploid genomes at least partially condensed; one or more decondensing units 434 operable to at least partially or completely decondense the one or more male germ line haploid genomes; one or more monitoring units 424 operable to detect one or more genetic characteristics of the one or more male germ line haploid genomes; and one or more controller units 426 operable to select one or more of the one or more male germ line haploid genomes at least partially based on the one or more genetic characteristics of the one or more male germ line haploid genomes. In some embodiments, one or more apparatus 411 includes one or more first sources of one or more male germ line haploid genomes, the one or more male germ line haploid genomes at least partially condensed; one or more units for decondensing the one or more male germ line haploid genomes; one or more monitors for detecting one or more genetic characteristics of the one or more male germ line haploid genomes; and one or more controllers for selecting one or more of the one or more male germ line haploid genomes at least partially based on the one or more genetic characteristics of the one or more male germ line haploid genomes.

In some embodiments, one or more apparatus 410 includes one or more sourcing units 420 including one or more first sources of one or more related spermatid genomes; one or more monitoring units 424 operable to detect one or more genetic characteristics of one or more of the one or more related spermatid genomes; and one or more controller units 426 operable to select, sort, and/or separate one or more of the one or more related spermatid genomes at least partially based on one or more of the genetic characteristics of one or more of the one or more related spermatid genomes. In some embodiments, one or more apparatus 410 includes one or more sourcing units 420 including one or more first sources of one or more related spermatid genomes; one or more computing units 428 operable to receive one or more inputs, the one or more inputs including data representative of one or more characteristics of one or more of the one or more related spermatid genomes; and one or more controller units 426 operable to select, sort, and/or separate one or more of the one or more related spermatid genomes at least partially based on the one or more genetic characteristics of one or more of the one or more related spermatid genomes.

In some embodiments, one or more apparatus 410 includes one or more sourcing units 420 including one or more first sources of one or more related spermatid genomes; one or more computing units 428 operable to receive one or more inputs, the one or more inputs including data representative of one or more characteristics of one or more of the one or more related spermatid genomes; and operable to determine the one or more related spermatid genomes to select, sort, and/or separate at least partially based on the one or more genetic characteristics of one or more of the one or more related spermatid genomes.

In some embodiments, one or more apparatus 410 includes one or more characterization units 419 operable to determine, detect, and/or identify one or more genetic characteristics of one or more related spermatid genomes; and one or more controller units 426 operable to select, sort, and/or separate one or more of the one or more related spermatid genomes at least partially based on the one or more genetic characteristics of one or more of the one or more related spermatid genomes. In some embodiments, one or more apparatus 410 includes one or more characterization units 419 operable to determine, detect, and/or identify one or more genetic characteristics of one or more related spermatid genomes; and one or more computing units 428 operable to determine the one or more related spermatid genomes to select, sort, and/or separate at least partially based on the one or more genetic characteristics of one or more of the one or more related spermatid genomes.

In some embodiments, one or more apparatus 410 includes one or more sourcing units 420 including one or more first sources of one or more related polar body genomes; one or more monitoring units 424 operable to detect one or more genetic characteristics of one or more of the one or more related polar body genomes; and one or more controller units 426 operable to select, sort, and/or separate one or more of the one or more related polar body genomes at least partially based on one or more of the genetic characteristics of one or more of the one or more related polar body genomes. In some embodiments, one or more apparatus 410 includes one or more sourcing units 420 including one or more first sources of one or more related polar body genomes; one or more computing units 428 operable to receive one or more inputs, the one or more inputs including data representative of one or more characteristics of one or more of the one or more related polar body genomes; and one or more controller units 426 operable to select, sort, and/or separate one or more of the one or more related polar body genomes at least partially based on the one or more genetic characteristics of one or more of the one or more related polar body genomes. In some embodiments, one or more apparatus 410 includes one or more sourcing units 420 including one or more first sources of one or more related polar body genomes; one or more computing units 428 operable to receive one or more inputs, the one or more inputs including data representative of one or more characteristics of one or more of the one or more related polar body genomes; and operable to determine the one or more related polar body genomes to select, sort, and/or separate at least partially based on the one or more genetic characteristics of one or more of the one or more related polar body genomes.

Figure 16:
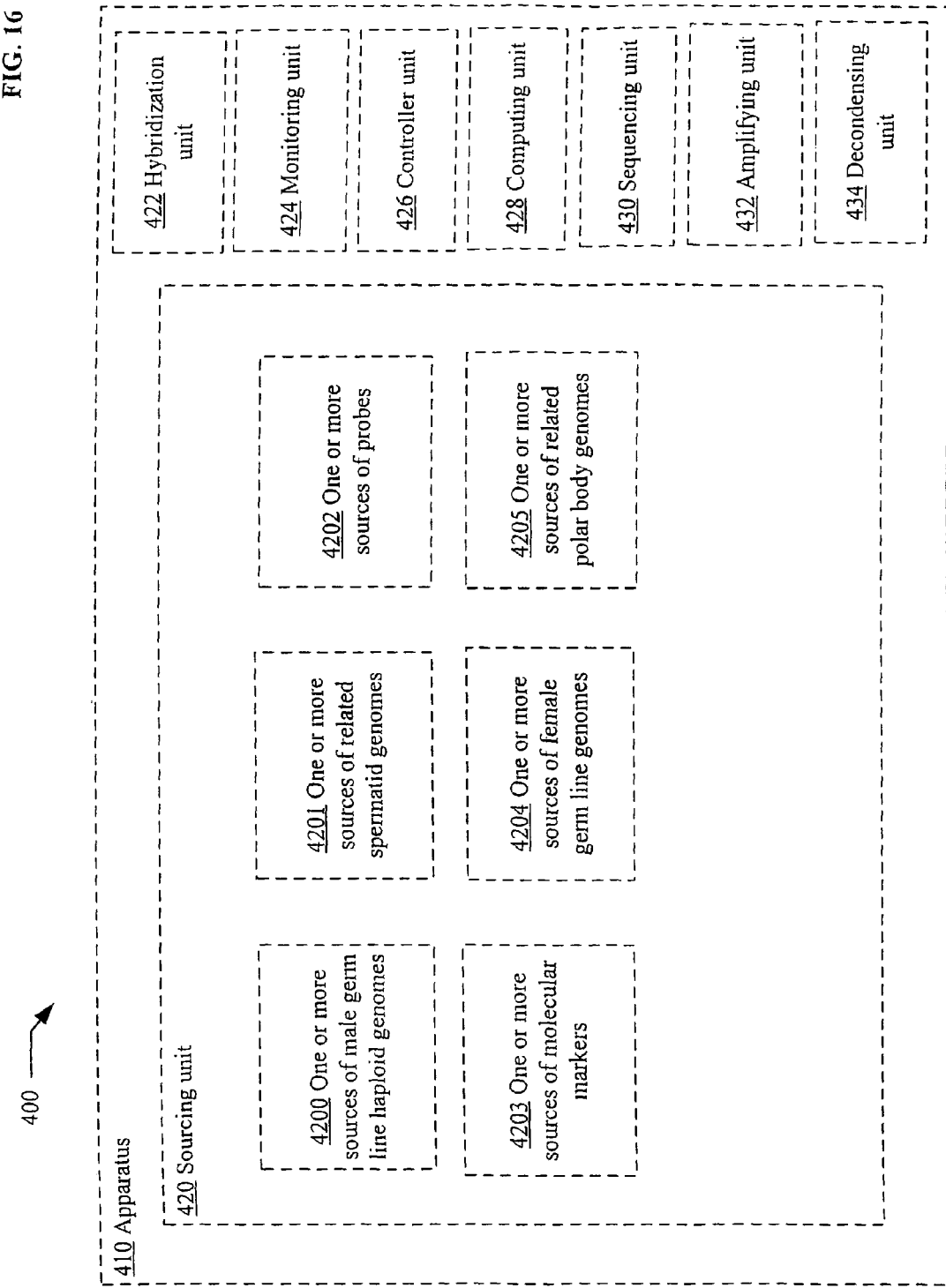
FIG. 16 shows schematics of illustrative embodiments of the apparatus of FIG. 15, with illustrative examples of a sourcing unit.

FIG. 16 shows a schematic 400 of illustrative embodiments of the optional apparatus 410 of FIG. 15, with specific illustrative embodiments of one or more sourcing units 420, including, but not limited to, unit 4200, unit 4201, unit 4202, unit 4203, unit 4204, and unit 4205. In some embodiments, one or more sourcing units 420 are internal to the apparatus 410; in some embodiments, one or more sourcing units are external to the apparatus 410. In some embodiments, one or more sourcing units are part of, the same as, and/or included in one or more characterization units 419, one or more of one or more hybridization units 422, one or more monitoring units 424, one or more controller units 426, one or more computing units 428, one or more sequencing units 430, one or more amplifying units 432, and/or one or more decondensing units 434.

In some embodiments, one or more sourcing units include one or more first sources of one or more male germ line haploid genomes 4200 and/or one or more related spermatid genomes 4201, the one or more first sources optionally positioned to provide the one or more male germ line haploid genomes and/or related spermatid genomes, to one or more first locations, one or more first units, one or more monitoring units, one or more controller units, one or more computing units, one or more sequencing units, and/or one or more hybridization units.

In some embodiments, one or more sourcing units 420 include one or more second sources of one or more probes 4202 and/or one or more molecular markers 4203, the one or more second sources optionally positioned to provide the one or more probes to one or more second locations, one or more first units, one or more monitoring units, one or more controller units, one or more computing units, one or more sequencing units, and/or one or more hybridization units.

In some embodiments, one or more sourcing units 420 include one or more third sources of one or more female germ line genomes 4204 and/or one or more related polar body genomes 4205, the one or more third sources optionally positioned to provide the one or more female germ line genomes and/or related polar body genomes to one or more third locations, one or more first units, one or more monitoring units, one or more controller units, one or more computing units, one or more sequencing units, and/or one or more hybridization units.

In some embodiments, one or more sourcing units 420 are operable to receive one or more inputs, the one or more inputs optionally including one or more of one or more female germ line genomes, one or more male germ line genomes, one or more probes and/or one or more molecule markers. In some embodiments, one or more sourcing units 420 are operable to provide one or more outputs, the one or more outputs optionally including one or more of one or more female germ line genomes, and/or one or more male germ line genomes. In some embodiments, the one or more male germ line genomes and/or the female germ line genomes are one or more haploid germ line genomes. In some embodiments, one or more male germ line genomes are one or more spermatid genomes, optionally one or more related spermatid genomes. In some embodiments, one or more female germ line genomes are one or more polar body genomes, optionally one or more related polar body genomes, and/or optionally one or more of one or more first polar body genomes or one or more second polar body genomes.

In some embodiments, one or more first locations are the same as one or more second locations, and/or one or more third locations, and optionally are included in one or more hybridization units 422, one or more monitoring units 424, one or more controller units 426, one or more computing units 428, one or more sequencing units, 430, one or more amplifying units 432, and/or one or more decondensing units 434. In some embodiments, one or more third locations, one or more second locations and/or one or more first locations are the same location.

In some embodiments, the one or more male germ line haploid genomes are at least partially isolated from one or more spermatozoa, and/or are part of one or more spermatozoa. In some embodiments, the one or more male germ line haploid genomes are at least partially isolated from one or more spermatids and/or are part of one or more spermatids. In some embodiments, the one or more male germ line haploid genomes are at least partially isolated from one or more spermatocytes and/or are part of one or more spermatocytes. In some embodiments, the one or more male germ line haploid genomes are at least partially condensed and/or are condensed. In some embodiments, the one or more male germ line haploid genomes are from one or more of animals, mammals, reptiles, birds or plants.

In some embodiments, one or more related spermatid genomes are part of one or more related spermatids and/or are at least partially isolated from one or more related spermatids. In some embodiments, one or more related spermatid genomes are from one or more of animals, mammals, reptiles, birds or plants.

In some embodiments, the one or more female germ line genomes are at least partially isolated from one or more of one or more ova, one or more oogonia, or one or more oocytes and/or are part of one or more of one or more ova, one or more oogonia, or one or more oocytes. In some embodiments, one or more female germ line genomes are from one or more of animals, mammals, reptiles, birds or plants.

In some embodiments, one or more related polar body genomes are part of one or more related polar bodies and/or are at least partially isolated from one or more related polar bodies. In some embodiments, one or more related polar body genomes are from one or more of animals, mammals, reptiles, birds or plants.

Figure 17:
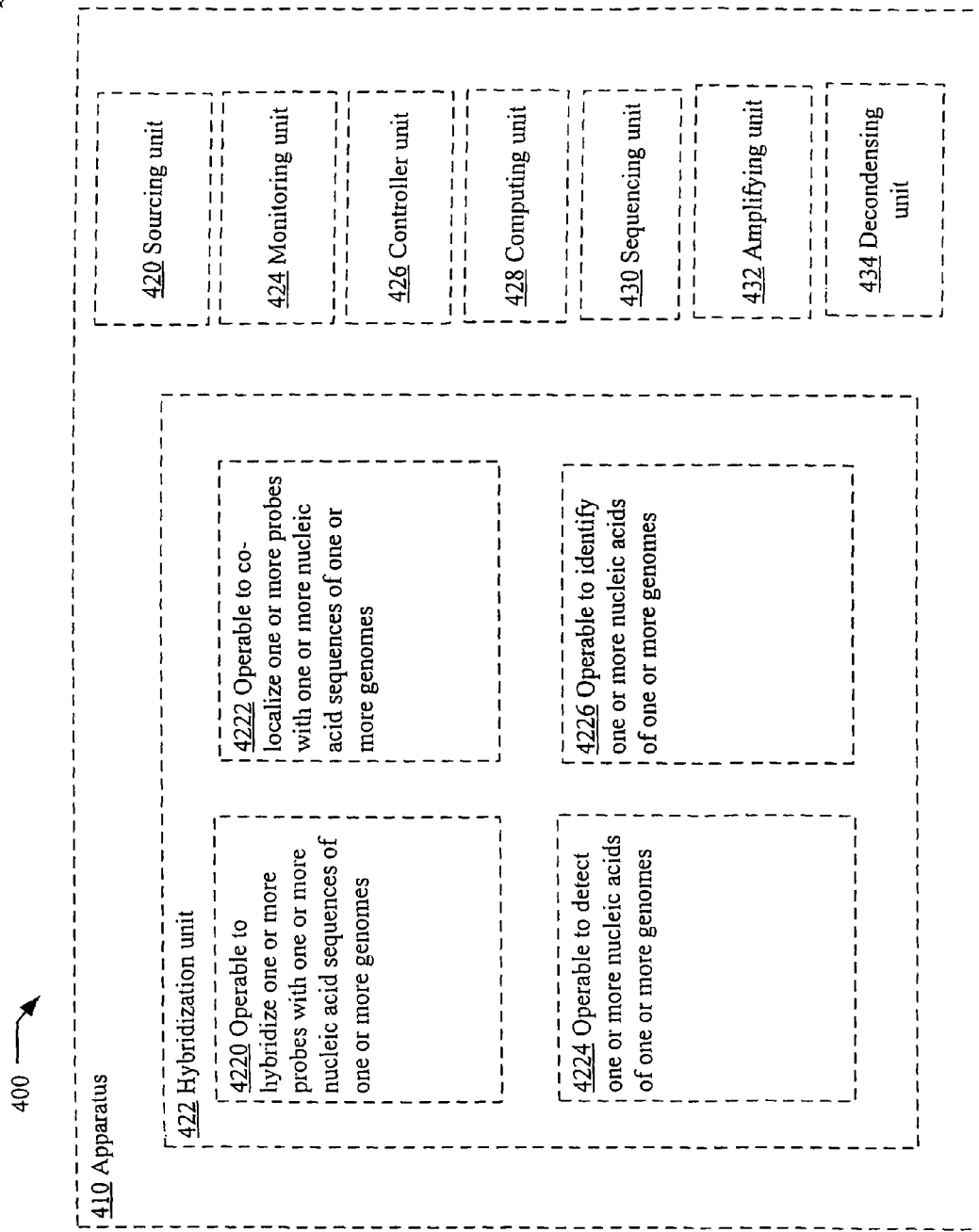
FIG. 17 shows schematics of illustrative embodiments of the apparatus of FIG. 15, with specific examples of a hybridization unit.

FIG. 17 shows a schematic 400 of illustrative embodiments of the optional apparatus 410 of FIG. 15, with specific illustrative embodiments of one or more hybridization units 422, including but not limited to, unit 4220, unit 4222, unit 4224, and/or unit 4226. In some embodiments, one or more hybridization units 422 are internal to the apparatus 410; in some embodiments, one or more hybridization units 422 are external to the apparatus 410. In some embodiments, one or more hybridization units 422 are part of the apparatus 410; in some embodiments, one or more hybridization units 422 are separate from the apparatus 410. In some embodiments, one or more hybridization units 422 are part of, the same as, and/or included in one or more of one or more characterization units 419, one or more sourcing units 420, one or more monitoring units 424, one or more controller units 426, one or more computing units 428, one or more sequencing units 430, one or more amplifying units 432, and/or one or more decondensing units 434.

In some embodiments, one or more hybridization units 422 are operable to detect one or more probes hybridized to one or more nucleic acids optionally of one or more male germ line haploid genomes and/or of one or more female germ line genomes. In some embodiments, one or more of the one or more hybridization units are operable to identify one or more of the one or more probes hybridized to one or more nucleic acids optionally of one or more male germ line haploid genomes and/or one or more female germ line genomes.

In some embodiments, one or more hybridization 422 units are operable to hybridize one or more probes with one or more nucleic acid sequences 4220 optionally of the one or more male germ line haploid genomes and/or one or more female germ line genomes. In some embodiments, one or more hybridization units are operable to co-localize one or more probes with one or more nucleic acid sequences 4222 of one or more male germ line haploid genomes and/or one or more female germ line genomes.

In some embodiments, one or more hybridization units 422 are operable to detect 4224, optionally destructively, one or more nucleic acid sequences of one or more genomes. In some embodiments, one or more hybridization units are operable to identify 4226, optionally destructively, one or more nucleic acid sequences of one or more genomes. In some embodiments, one or more hybridization units 422 are operable to detect 4224, optionally destructively, one or more probes hybridized to one or more nucleic acids optionally of one or more related spermatid genomes and/or of one or more related polar body genomes. In some embodiments, one or more hybridization units are operable to identify 4226, optionally destructively, one or more probes hybridized to one or more nucleic acids optionally of one or more related spermatid genomes and/or one or more related polar body genomes.

In some embodiments, one or more hybridization units 422 are operable to hybridize 4220, optionally destructively, one or more probes with one or more nucleic acid sequences optionally of the one or more related spermatid genomes and/or one or more related polar body genomes. In some embodiments, one or more hybridization units are operable to co-localize 4222, optionally destructively, one or more probes with one or more nucleic acids of one or more related spermatid genomes and/or one or more polar body genomes.

Figure 18:
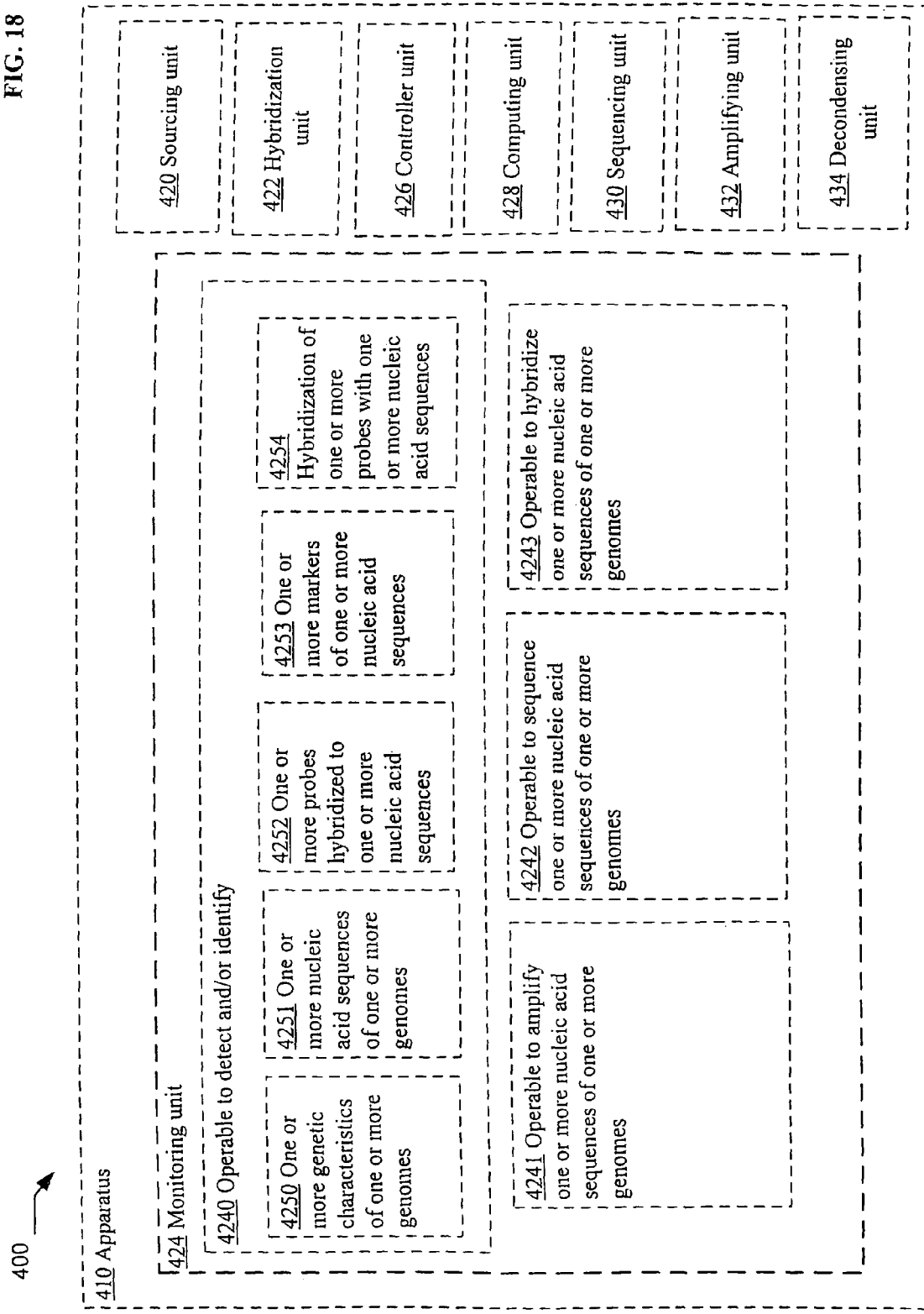
FIG. 18 shows schematics of illustrative embodiments of the apparatus of FIG. 15, with illustrative examples of a monitoring unit.

FIG. 18 shows a schematic 400 of illustrative embodiments of the optional apparatus 410 of FIG. 15, with specific illustrative embodiments of one or more monitoring units 424, including but not limited to, unit 4240, unit 4241, unit 4242, and/or unit 4243. In some embodiments, one or more monitoring units 424 are internal to the apparatus 410; in some embodiments, one or more monitoring units 424 are external to the apparatus 410. In some embodiments, one or more monitoring units 424 are part of the apparatus 410; in some embodiments, one or more monitoring units 424 are separate from the apparatus 410. In some embodiments, one or more monitoring units 424 are part of, the same as, and/or included in one or more of one or more characterization units 419, one or more sourcing units 420, one or more hybridization units 422, one or more controller units 426, one or more computing units 428, one or more sequencing units 430, one or more amplifying units 432, and/or one or more decondensing units 434.

In some embodiments, one or more monitoring units 424 are operable to detect and/or identify one or more genetic characteristics 4250 of one or more female germ line genomes and/or one or more male germ line haploid genomes. In some embodiments, one or more monitoring units are operable to detect and/or identify one or more nucleic acid sequences 4251 of one or more male germ line haploid genomes and/or one or more female germ line genomes.

In some embodiments, one or more monitoring units 424 are operable to detect association with, binding, and/or hybridization of one or more probes 4254 and/or one or more molecular markers with one or more nucleic acids of one or more male germ line haploid genomes and/or one or more female germ line genomes. In some embodiments, one or more monitoring units 424 are operable to detect and/or identify one or more probes or one or more molecular markers associated with, bound, and/or hybridized to one or more nucleic acids 4252 of one or more male germ line haploid genomes and/or one or more female germ line genomes.

In some embodiments, one or more monitoring units are operable to detect and/or identify, optionally destructively, optionally in situ, one or more genetic characteristics 4250 and/or one or more nucleic acid sequences 4251 of one or more related spermatid genomes and/or one or more related polar body genomes. In some embodiments, one or more monitoring units are operable to detect and/or identify, optionally destructively, optionally in situ, one or more markers of one or more nucleic acid sequences 4253 of one or more related spermatid genomes and/or one or more related polar body genomes. In some embodiments, one or more monitoring units are operable to detect and/or identify, optionally destructively, optionally in situ, one or more probes hybridized to one or more nucleic acid sequences 4252 of one or more related spermatid genomes and/or one or more related polar body genomes.

In some embodiments, one or more monitoring units are operable to amplify 4241, optionally destructively, optionally in situ, one or more nucleic acid sequences of one or more genomes. In some embodiments, one or more monitoring units are operable to sequence 4242, optionally destructively, optionally in situ, one or more nucleic acid sequences of one or more genomes. In some embodiments, one or more monitoring units are operable to hybridize 4243, optionally destructively, optionally in situ, one or more probes to one or more nucleic acid sequences of one or more genomes.

In some embodiments, one or more monitoring units are operable to amplify 4241, optionally destructively, optionally in situ, one or more nucleic acid sequences of one or more related spermatid genomes and/or one or more related polar body genomes. In some embodiments, one or more monitoring units are operable to sequence 4242, optionally destructively, optionally in situ, one or more nucleic acid sequences of one or more of the one or more related spermatid genomes and/or one or more related polar body genomes. In some embodiments, one or more monitoring units are operable to hybridize 4243, optionally destructively, optionally in situ, one or more probes to one or more nucleic acid sequences of the one or more related spermatid genomes and/or one or more related polar body genomes.

Figure 19:
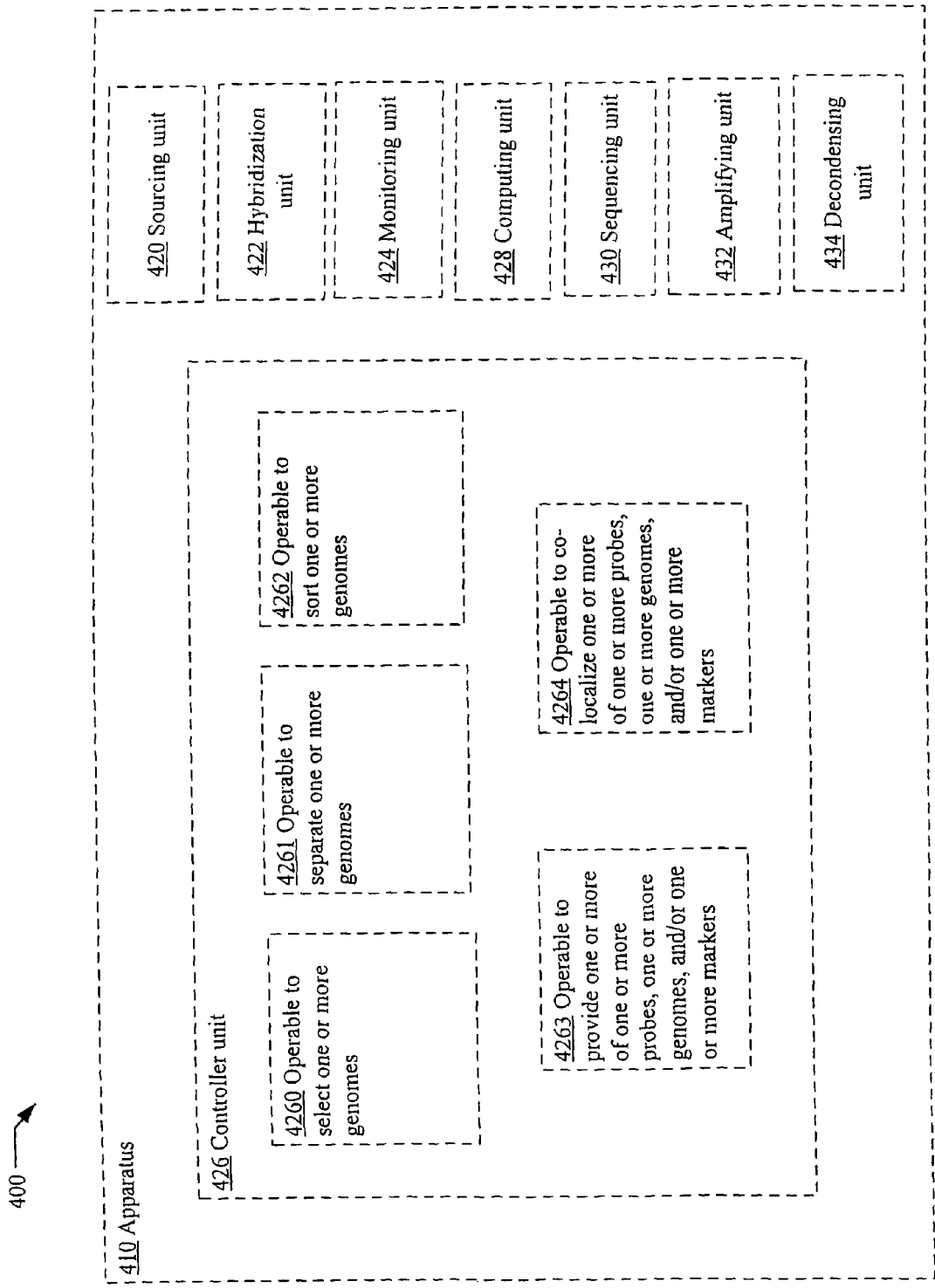
FIG. 19 shows schematics of illustrative embodiments of the apparatus of FIG. 15, with illustrative examples of a controller unit.

FIG. 19 shows a schematic 400 of illustrative embodiments of the optional apparatus 410 of FIG. 15, with specific illustrative embodiments of one or more controller units 426, including but not limited to, unit 4260, unit 4261, unit 4262, unit 4263 and/or unit 4264. In some embodiments, one or more controller units 426 are internal to the apparatus 410; in some embodiments, one or more controller units 426 are external to the apparatus 410. In some embodiments, one or more controller units 426 are part of, the same as, and/or included in one or more of one or more characterization units 419, one or more sourcing units 420, one or more hybridization units 422, one or more monitoring units 424, one or more computing units 428, one or more sequencing units 430, one or more amplifying units 432, and/or one or more decondensing units 434.

In some embodiments, one or more controller units 426 are operable to select 4260, separate 4261, and/or sort 4262 one or more of the one or more male germ line haploid genomes at least partially based on the one or more genetic characteristics of the one or more male germ line haploid genomes and/or a weighted combination of one or more genetic characteristics of one or more male germ line haploid genomes. In some embodiments, one or more controller units are operable to select 4260, separate 4261, and/or sort 4262 one or more of the one or more male germ line haploid genomes at least partially based on one or more genetic characteristics of one or more female germ line genomes and/or a weighted combination of one or more genetic characteristics of one or more female germ line genomes. In some embodiments, one or more controller units are operable to select 4260, separate 4261, and/or sort 4262 one or more of the one or more male germ line haploid genomes at least partially based on one or more of one or more target genetic characteristics or one or more reference genetic characteristics and/or a weighted combination of one or more of one or more target genetic characteristics or one or more reference genetic characteristics.

In some embodiments, one or more of the one or more controller units 426 are operable to select 4260, separate 4261, and/or sort 4262 one or more of the one or more male germ line haploid genomes optionally at least partially based on the detection and/or identification of one or more probes and/or molecular markers associated with, bound, and/or hybridized to one or more nucleic acids optionally of one or more male germ line haploid genomes and/or one or more female germ line genomes.

In some embodiments, one or more controller units 426 are operable to provide 4263 one or more probes to the one or more male germ line haploid genomes, and/or to provide 4263 one or more male germ line haploid genomes to one or more of the one or more probes. In some embodiments, one or more controller units are operable to provide 4263 one or more male germ line haploid genomes and/or one or more of the one or more probes to one or more first locations and/or to one or more hybridization units.

In some embodiments, one or more controller units 426 are operable to co-localize 4264 one or more probes with the one or more male germ line haploid genomes, and/or to co-localize 4264 one or more male germ line haploid genomes with one or more of the one or more probes. In some embodiments, one or more controller units are operable to co-localize 4264 one or more male germ line haploid genomes and/or one or more of the one or more probes at one or more first locations and/or at one or more hybridization units.

In some embodiments, the one or more male germ line haploid genomes are one or more related spermatid genomes. In some embodiments, the one or more female germ line genomes are one or more related polar body genomes, optionally one or more first polar body genomes and/or one or more second polar body genomes.

Figure 20:
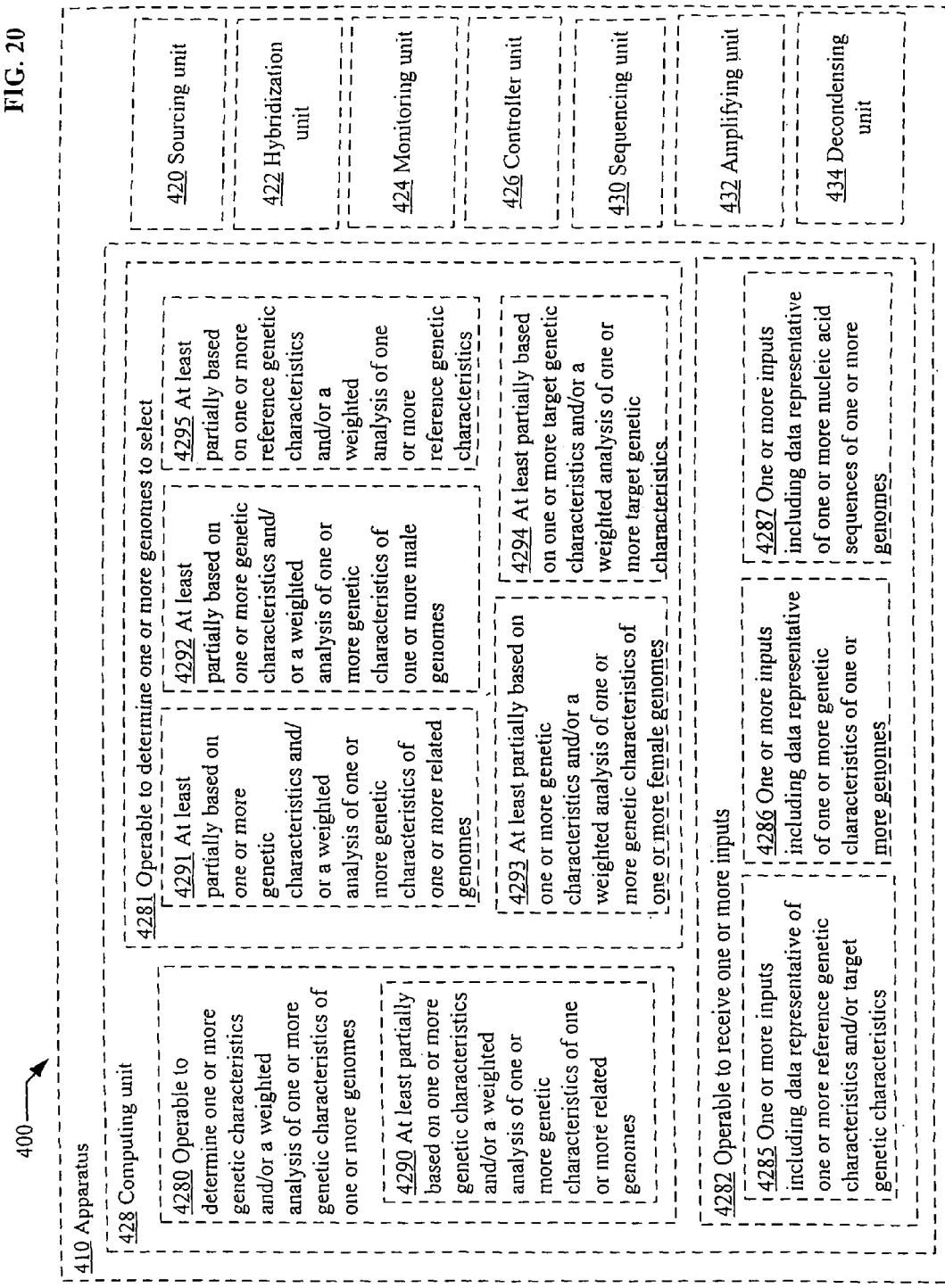
FIG. 20 shows schematics of illustrative embodiments of the apparatus of FIG. 15, with illustrative examples of a computing unit.

FIG. 20 shows a schematic 400 of illustrative embodiments of the optional apparatus 410 of FIG. 15, with specific illustrative embodiments of one or more computing units 428, including but not limited to, unit 4280, unit 4281, and/or unit 4282. In some embodiments, one or more computing units 428 are internal to the apparatus 410; in some embodiments, one or more computing units 428 are external to the apparatus 410. In some embodiments, one or more computing units 428 are part of, the same as, and/or included in one or more of one or more characterization units 419, one or more sourcing units 420, one or more hybridization units 422, one or more monitoring units 424, one or more controller units 426, one or more sequencing units 430, one or more amplifying units 432, and/or one or more decondensing units 434.

In some embodiments, one or more apparatus 410 further includes one or more computing units 428 operable to determine one or more genetic characteristics 4280 of one or more genomes and/or a weighted analysis of one or more genetic characteristics of one or more genomes.

In some embodiments, one or more computing units 428 are operable to determine one or more genetic characteristics and/or a weighted analysis of one or more genetic characteristics 4280 of one or more genomes, optionally one or more male germ line haploid genomes and/or one or more female germ line genomes, optionally at least partially based on detection and/or identification of one or more of the one or more probes hybridized to the one or more nucleic acids of one or more of the one or more male germ line haploid genomes. In some embodiments, one or more computing units are operable to determine one or more genetic characteristics and/or a weighted analysis of one or more genetic characteristics 4280 of one or more genomes, optionally one or more male germ line haploid genomes and/or one or more female germ line genomes, optionally at least partially based on the detected one or more genetic characteristics of the one or more male germ line haploid genomes.

In some embodiments, one or more computing units 428 are operable to determine one or more genetic characteristics and/or a weighted analysis of one or more genetic characteristics 4280 of one or more genomes, optionally one or more related spermatid genomes and/or one or more related polar body genomes, optionally at least partially based on detection and/or identification of one or more of the one or more probes and/or one or more molecular markers associated with, bound, and/or hybridized to the one or more nucleic acids of one or more related genomes. In some embodiments, one or more computing units are operable to determine one or more genetic characteristics and/or a weighted analysis of one or more genetic characteristics 4280 of one or more genomes, optionally one or more related spermatid genomes and/or one or more related polar body genomes, optionally at least partially based on the detected one or more genetic characteristics of the one or more related genomes.

In some embodiments, the one or more computing units 428 are operable to determine one or more genomes to select, sort, and/or separate 4281 at least partially based on one or more genetic characteristics of one or more related genomes, and/or based on a weighted analysis of one or more genetic characteristics of one or more related genomes 4291. In some embodiments, one or more related genomes are one or more related spermatid genomes and/or one or more related polar body genomes.

In some embodiments, the one or more computing units 428 are operable to determine one or more genomes, optionally one or more male germ line haploid genomes and/or one or more female germ line genomes, to select, sort, and/or separate 4281 at least partially based on one or more genetic characteristics of one or more male genomes, optionally one or more male germ line haploid genomes, and/or on a weighted analysis of one or more genetic characteristics of one or more male genomes, optionally one or more male germ line haploid genomes 4292.

In some embodiments, one or more computing units are operable to determine one or more genomes, optionally one or more male germ line haploid genomes and/or one or more female germ line genomes, to select, sort, and/or separate 4281 at least partially based on one or more genetic characteristics of one or more female genomes, optionally one or more female germ line genomes, and/or a weighted analysis of one or more genetic characteristics of one or more female genomes, optionally one or more female germ line genomes 4293.

In some embodiments, one or more computing units 428 are operable to determine one or more male genomes, optionally one or more male germ line haploid genomes and/or one or more female germ line genomes, to select, sort, and/or separate 4281 at least partially based on one or more of one or more target genetic characteristics or one or more reference genetic characteristics and/or a weighted combination of one or more of one or more target genetic characteristics 4294 or one or more reference genetic characteristics 4295.

In some embodiments, one or more computing units 428 are operable to receive one or more inputs 4282, the one or more inputs optionally including data representative of one or more genetic characteristics 4286 and/or one or more nucleic acid sequences 4287 of one or more genomes, optionally one or more female germ line genomes and/or one or more male germ line genomes. In some embodiments, the one or more female germ line genomes and/or the one or more male germ line genomes are one or more haploid genomes. In some embodiments, one or more computing units 428 are operable to receive one or more inputs 4282, the one or more inputs optionally including data representative of one or more of one or more target genetic characteristics and/or one or more reference genetic characteristics 4285.

In some embodiments, the one or more male germ line haploid genomes are one or more related spermatid genomes 4291. In some embodiments, the one or more female germ line genomes are one or more related genomes 4291, optionally one or more polar body genomes, optionally one or more first polar body genomes and/or one or more second polar body genomes.

Materials and reagents described in the Examples are commercially available, unless otherwise specified.

Example 1

Mammalian Spermatozoa Selection Based on Nucleic Acid Hybridization with Peptide Nucleic Acid Sperm cells from, for example, boar, bull, stallion or ram, are collected using known animal husbandry methods including using a gloved-hand, an artificial vagina, and/or electro-ejaculation methods as appropriate.

After collection, the semen is diluted with a species-specific buffer to extend the lifespan of the sperm outside the body (e.g. artificial insemination buffer). Appropriate diluents provide energy and nutrients, buffering action for pH changes (e.g. due to lactic acid formation), protection from temperature shock (e.g. rapid cooling), maintain osmotic pressure, balance electrolytes, inhibit microorganism growth, as well as facilitating dilution to an appropriate volume for hybridization and selection. For example, a 2.9% sodium citrate—egg yolk buffer may be used for cattle (see, e.g., J. Dairy Sci. (1941) 24:905), and a Beltsville Thaw Solution (BTS) may be used for boar sperm.

The DNA sequence of interest is identified. Such DNA sequence can be, for example, a trait locus, a particular allele, or other DNA sequence targeted for hybridization.

Based on the sequence of the DNA to be targeted, peptide nucleic acids that bind the target DNA sequence are designed and constructed following the procedures described, for example, by Eur. J. Hum. Genetics (2003) 11:337-341; Mammalian Genome (2000) 11:384-391; Adv. in Genetics (2006) 56:1-51; EMBO J (2003) 22:6631-6641; Mammalian Genome (1999) 10:13-18; or Mol. Hum. Repro. (2004) 10:467-472). Alternatively, the peptide nucleic acids may be synthesized using an Applied Biosystems 3400 DNA Synthesizer or an ABI 3900 Synthesizer, or using custom commercial services.

Peptide nucleic acids (from, for example, Applied Biosystems) may be conjugated with various fluorescent dyes such as FITC, TRITC, and/or BODIPY® derivatives, for example, and/or quantum dots (see, e.g., Histochem. Cell Biol. (2006) 125:451-456). BODIPY® dyes are membrane soluble, aiding penetration of probes (from, for example, Molecular Probes Inc.; described in, for example, U.S. Pat. No. 5,338,854 or U.S. Pat. No. 4,774,339). PNA probes are used at a final concentration of about 0.1 to about 100 µM depending on the cell concentration, among other things.

Labeled or unlabeled peptide nucleic acids are added to diluted sperm samples under conditions to effect hybridization while minimizing the impact on motility and/or viability. In some instances, peptide nucleic acid probes with fluorescent tags may readily penetrate the cells, travel to the nucleus, and bind nuclear DNA. Optionally, cell penetration is facilitated by methods known in the art including electroporating, chemically shocking (e.g. using glycerol and/or DMSO), liposome-encapsulating, micro-injecting, DEAE-dextran-mediated transferring, co-precipitating with calcium phosphate, and/or adding cell-permeation enhancing solutions such as mild surfactants and/or DMSO.

Hybridization incubations may range from about 30 minutes to about 24 hours or about 144 hours or longer, depending on the ease of uptake into the cell nucleus and target binding. Hybridization temperatures may range from the thermotropic phase transition temperature of the membranes of the sperm, to room temperature (approximately 23° C.), to less than about 30° C., or to less than about 39° C.

Cells with fluorescently labeled peptide nucleic acids that hybridized to target nucleic acids are identified by detection of their emitted fluorescence using conventional methods. Following hybridization, cells are sorted, using for example flow cytometry or microfluorometry, based on differences in quantitative and/or qualitative fluorescence to produce subpopulations enriched or depleted in cells with one or more target sequences. Cells may also be sorted using fluorescent microscopy. Methods for effecting flow cytometry separations while minimizing the impact on cell motility and/or viability are known in the art (e.g. U.S. Pat. No. 5,135,759, or U.S. Pat. No. 5,985,216), and appropriate systems have been described herein, and in WO 03/020877, for example.

Example 2

Mammalian Spermatozoa Nuclei Selection Based on Nucleic Acid Hybridization with Peptide Nucleic Acid Methods of isolating sperm nuclei are known in the art (see, e.g., Hum. Reprod. (2005) 20:2784-2789). Semen is washed three times by centrifugation at 1620 g for 10 minutes in, for example, 50 mmol/L Tris-HCl, pH 7.2 and 0.15 mol/L NaCl (10× sample volume). Sperm pellets are resuspended in, for example, 2.6 ml of the same buffer containing 1% SDS, incubated for 15 minutes at room temperature, and sonicated six times for 15 seconds each at 200 W using, for example, a Branson sonifier cell disruptor, model W 140 (Branson Sonic Power Co., Plainview, N.Y.). Sonicated cell solutions are centrifuged at 3500 g for 1 hour through a 1.1 mol/L sucrose in 50 mmol/L Tris-HCl, pH 7.2 gradient. Pellets are washed twice by centrifugation at 1620 g for 10 minutes in, for example, 50 mmol/L Tris-HCl, pH 7.2. Lack of contamination of the nuclear fraction may be assessed by microscopic examination, for example.

PNAs are designed and constructed using methods and materials described herein or known in the art. Hybridization of the PNA is induced using the methods and materials described herein or known in the art.

Following hybridization, nuclei are sorted, using for example flow cytometry or microfluorometry, based on differences in quantitative and/or qualitative fluorescence to produce subpopulations enriched or depleted in nuclei with one or more target sequences. Alternatively, nulcei may be sorted using fluorescent microscopy. Methods for effecting flow cytometry separations while minimizing the impact on nuclei viability are known in the art (e.g. U.S. Pat. No. 5,135,759 or U.S. Pat. No. 5,985,216), and appropriate systems have been described herein, and, for example, in WO 03/020877.

Example 3

Decondensation and Nucleic Acid-Based Selection of Mammalian Spermatozoa

Semen samples are obtained using methods known in the art and/or described herein. Semen may be allowed to liquefy at room temperature for approximately 30 min to 3 hours.

Semen solutions are demembranated, for example by diluting 1:10 in a demembranating solution pre-warmed to approximately 37° C., or other appropriate temperature based, for example, on the body temperature of the species from which the sperm is recovered. Demembranating solutions are known in the art (see, e.g., J. Exp. Zoology (1999) 284:789-797), and can be modified to achieve the desired extent of demembranation by altering, for example, the concentration of Triton X-100 (specially purified for membrane research, available from, for example, Boehringer-Mannhein, Germany) in the solution from approximately 0.01%, 0.015%, 0.017%, 0.02%, to 0.022%, for example. During demembranation, samples may be stirred for 20 seconds, and allowed to sit unstirred for 25 seconds.

Demembranated semen samples are decondensed, for example by diluting 1:10 with decondensing solution pre-warmed to approximately 37° C. (or other appropriate temperature as discussed above), stirred briefly, and then allowed to incubate at 37° C. for approximately 30 seconds, 5 minutes, 10 minutes or 15 minutes depending on the species and extent of decondensation desired. Decondensation solutions are known in the art (see, e.g., J. Exp. Zoology (1999) 284:789-797), and may include 24 mM potassium glutamate, 192 mM sucrose, 1.2 mM $MgSO_4$, 19.2 mM Hepes (N-2-hydroxyethylpiperazine-N-2-ethanesulfonic acid), 5.8 mM EDTA (ethylene diamine tetraacetic acid), 2.9 mM DTT (dithiothreitol, Sigma D-0632), 48 µM cAMP (adenosine 3':5'-cyclic monophosphate; Sigma A-6885), and 4.03 USP units/ml heparin (sodium salt grade 1: from porcine intestinal mucosa, Sigma), pH 7.8.

Demembranated and/or decondensed sperm samples may be diluted 1:10 in reactivating solution pre-warmed to approximately 37° C. (or other appropriate temperature as discussed above), stirred briefly, and then allowed to incubate at 37° C. for a few minutes. Reactivating solutions are known in the art (e.g. J. Exp. Zoology (1999) 284:789-797), and may include 5 mM adenosine 5'-triphosphate (ATP, Sigma A-5394) and 2.5 mM $MgSO_4$.

Sperm demembranation, decondensation, and/or reactivation can be monitored using microscopic examination, for example.

Decondensed, and optionally reactivated, sperm may be exposed to one or more nucleic acid binding solutions including polyamide, peptide nucleic acid, and/or oligonucleic acid probes under conditions to facilitate binding and/or hybridization.

Example 4

Decondensation and Nucleic Acid-Based Selection of Mammalian Spermatozoa and Isolated Nuclei Semen may be obtained by methods described herein and/or in the art. Semen samples are allowed to liquefy up to one hour prior to capacitation or nuclei isolation.

Methods for capacitating semen samples are known in the art (see, e.g., Hum. Reprod. (2005) 20:2784-2789). Semen samples are washed twice by centrifugation at 300 g for 10 minutes in a 1:5 dilution of tubal fluid medium (e.g. HTF; from, for example, Irvine Sceintific, Santa Ana, Calif.) supplemented with 0.3% bovine serum albumin (BSA). The sperm pellet is overlaid with 1 ml fresh HTF with 2.6% BSA (HTF-26B) for 90 minutes at about 37° C. (or other appropriate temperature for the species) in an atmosphere of 5% $CO_2$ in air.

Sperm nuclei then are isolated using methods known in the art, or as described herein, for example in Example 2 above.

Methods of decondensing capacitated sperm and isolated nuclei are known in the art (see, e.g., Hum. Reprod. (2005) 20:2784-2789). Sperm and isolated nuclei are incubated in HTF with 46 µmol/L Heparin and 10 mmol/L glutathione (GSH) for approximately 15, 30 or 60 minutes at 37° C. (or other appropriate temperature for the species) in an atmosphere of 5% $CO_2$ in air. The extent of decondensation can be assessed by phase-contrast in an Olympus CH2 microscope at 400× magnification, for example.

Decondensed sperm and/or isolated nuclei can be exposed to one or more nucleic acid binding solutions including, for example, polyamide, peptide nucleic acid, and/or oligonucleic acid probes under conditions to facilitate binding and/or hybridization, as appropriate.

Example 5

Decondensation of Mammalian Spermatozoa

Methods for decondensing mammalian sperm are known in the art (see, e.g., Theriogenology (2005) 63:783-794). Frozen or fresh sperm (from e.g. boar, bovine) may be incubated in Dulbecco's phosphate buffered saline (DPBS; Life Technologies) supplemented with 0.1% polyvinyl alcohol (PVA) and 5 mM DTT for approximately 50 minutes. Other appropriate buffers may be used, and the final DTT concentration varied depending on the species of the sperm. Sperm are washed three times before fertilization by centrifugation at 400 g for 5 minutes in 2 ml DPBS-PVA without 5 mM DTT.

Example 6

Recondensation of Selected Mammalian Spermatozoa and Isolated Nuclei

Methods for recondensing DNA are known in the art and include incubation with protamine in a low ionic strength buffer (see, e.g., J. Biol. Chem. (2004) 279:20088-20095). Partially and/or completely decondensed sperm and/or isolated nuclei can be partially and/or completely recondensed by incubation with protamine in a low ionic strength buffer.

Protamine can be isolated from sperm cells (e.g. bull protamine from bull sperm cells, or species specific to the sperm and/or isolated nuclei) by methods known in the art (see, e.g., J. Biol. Chem. (2004) 279:20088-20095). Isolated sperm cell chromatin is solubilized in 2.6 M urea, 1.1 M NaCl, 0.9 M guanidine hydrochloride (GuCl), and 150 mM 2-mercaptoethanol, and DNA is precipitated from the solution with concentrated HCl. The protamine solution is dialyzed against 10 mM HCl, and the protamine is precipitated with trichloroacetic acid, washed in acetone, and dissolved in $dH_2O$.

Solubilized protamine is filter-sterilized using, for example, Amicon Ultrafree-MC centrifugal filters with 0.22 µm pore diameter (Millipore). Partially or completely decondensed sperm and/or isolated nuclei are incubated in a solution including approximately 2.25 µM protamine, 10 mM sodium cacodylate, and 100 µM EDTA (pH 7.5) for approximately 10 minutes, 30 minutes, one hour, two hours, to at least three hours at 37° C. (or other appropriate temperature for the species) in an atmosphere of 5% $CO_2$ in air.

Example 7

Mammalian Female Reproductive Cell and/or Isolated Nuclei Selection Based on Nucleic Acid Hybridization and/or Binding Female reproductive cells, including oocytes, ova, and/or polar bodies, from, for example, cows, sows, ewes, and mares are collected using known animal husbandry methods including, for example, super-ovulation, in vitro production, and collection at slaughter. Mice, for example, may be superovulated by consecutive injections of eCG (5 IU) and hCG (5 IU) 48 hours apart. About 14 hours following hCG injections, oocyte-cumulus complexes are released from oviducts into Hepes-CZB. Cumulus cells can be dispersed by 5 minutes treatment with 0.1% bovine testicular hyaluronidase (300 USP units/mg; from, for example, ICN Pharmaceuticals, Costa Mesa, Calif.) in Hepes-CZB (see, e.g., Biol. Reprod. (1998) 59:100-104).

After collection, female reproductive cells are cultured and/or maintained in a variety of balanced salt solutions (e.g. TC199, M16, NCSU23) known in the art at appropriate temperatures, for example ones resembling the body temperature the species from which the cell was isolated (e.g. mice at 37° C., pig at 39° C.). Cumulus-free mice oocytes can be kept in CZB at 37.5° C. under 5% CO2 in air. Appropriate solutions and temperatures extend the length of cell viability and function and may be modified as appropriate (see, e.g., J. Cell. Biol. (1986) 102:568).

Methods of designing and constructing probes to bind and/or hybridize to target DNA sequences such as those indicative of a particular allele, trait locus, or other feature of interest are known in the art and described herein. Probes may include peptide nucleic acids, polyamides, and/or oligonucleotides, among others, and may be tagged with one or more tags known in the art and/or described herein.

Methods of imaging molecules in living cells and isolated cell nuclei are known in the art and described herein (see, e.g., Histochem. Cell Biol. (2006) 125:451-456; Biochem. Biophys. Res. Commun. (2006) 344:772-779; or Nature (2004) 5:856-862). One approach is to use quenched probes that fluoresce only when hybridized/bound to the target nucleic acid sequence (see, e.g., Trends in Biotech. (2005) 23:225-230; or Curr. Organic Chem. (2006) 10:491-518).

Probes are provided to the nucleus, using for example, mild membrane permeabilization, microinjection, and/or probes amenable to uptake, such as polyamides and peptide nucleic acids.

Following hybridization, cells and/or nuclei are sorted, using for example flow cytometry or microfluorometry, based on differences in quantitative and/or qualitative fluorescence to produce subpopulations enriched or depleted in cells and/or nuclei with one or more target sequences. Alternatively, cells and/or nuclei can be sorted using fluorescent microscopy. Methods for effecting flow cytometry separations while minimizing the impact on cells and/or nuclei viability are known in the art (see, e.g., U.S. Pat. No. 5,135,759, or U.S. Pat. No. 5,985,216), and appropriate systems have been described herein, and in WO 03/020877, for example.

Example 8

Fertilization Using Polar Body Genomes

Female reproductive cells, including oocytes, ova, and/or polar bodies, from, for example, cows, sows, ewes, and mares are collected, cultured and maintained using methods described above in Example 7 or known in the art.

Methods for enucleating recipient oocytes are known in the art (see, e.g., Biol. Reprod. (1998) 59:100-104). Enucleation of mice mature oocytes is performed using, for example, Hepes-CZB containing 5 µg/mlcytocholasin B (25° C. for 10 minutes). Oocytes held by a pipette are rotated until detection of a small, translucent ooplasmic spot—the location of metaphase II chromosomes. The zona pellucida is drilled with an enucleation pipette (approx. 10 µm inner diameter) by applying a few piezo pulses, and its tip is advanced until it reaches the translucent spot identified above. The translucent spot (and metaphase chromosomes) are drawn into the pipette gently, without breaking the plasma membrane, and pulled away from the oocyte until a stretched cytoplasmic bridge breaks off. Success of enucleation may be assessed using Hoechst 33342 staining.

Methods for transferring first polar bodies into enucleated oocytes are known in the art (see, e.g., Biol. Reprod. (1998) 59:100-104). The zona pellucida of oocytes with live polar bodies (assessed according to, for example, Live/Dead FertiLight; Molecular Probes, Inc. Eugene Oreg.) are drilled into with a piezo-driven injection pipette. The plasma membrane of the polar body may be broken when sucking into the pipette. The entire contents are injected into an enucleated oocyte, and are incubated in CZB for 2 hours at 37.5° C. under $CO_2$ in air prior to fertilization.

Methods for transferring second polar bodies into enucleated oocytes and/or nucleated zygotes are known in the art (see, e.g., J. Reprod. Fertility (1997) 110:263-266). Second polar bodies and female pronuclei may be removed from zygotes through the zonae pellucidae using micromanipulators under an inverted microscope with Nomarski optics, for example. The second polar body is inserted into the perivitelline space of a recipient zygote with one pronucleus, and placed in a drop (10 µl) of fusion medium (300 mmol/L mannitol, 0.05 mmol/L $CaCl_2$, 0.1 mmol/L $MgSO_4$, 5 mg/ml polyvinylpyrrolidone) between the electrodes of a circular electrofusion chamber (from, for example, Shimadzu, Kyoto). The width and depth of the electrode gap are 0.5 and 2.0 mm, respectively, and electrofusion is induced by applying 20 V/cm AC for 30 seconds, 3000 V/cm DC for 10 and 20 C/cm AC for 90 seconds, consecutively.

Example 9

Selection of Ova Using First Polar Body and/or Second Polar Body Genetic Information First and/or second polar bodies from oocytes are obtained using methods known in the art (e.g. Biol. Reprod. (1998) 59:100-104; J. Reprod. Fertility (1997) 110:263-266; Reproductive BioMedicine Online (2003) 6:403-409; Mol. Hum. Reprod. (1999) 5:89-95). Oviductal oocytes may be collected from mice, for example, between 13 and 17 hours after hCG injection, and the viability of the first polar body assessed (as above, for example). The second polar body may be extruded following parthenogenic activation or fertilization.

Genetic analysis of the polar bodies is performed using methods known in the art (see, e.g., Mol. Hum. Reprod. (1999) 5:89-95; Fertility and Sterility (2002) 78:543-549; J. Assisted Reprod & Genetics (1998) 15: 253-257; Prenat. Diagn. (2000) 20:1067-1071; Reprod. BioMed. OnLine (2002) 4:183-196; Prenat. Giagn. (2002) 21:767-780; or Mol. Cell. Endocrinol. (2001) 183:S47-S49). Based on the information gathered from genetic analysis of one or more of the polar bodies, and compared with the genetic information of diploid cells, the genetic information of the haploid ova can be determined. The desired ovum can be selected and electrofused, for example, with a selected male pronuclei.

Example 10

Selection of Spermatids and/or at Least Partially Isolated Spermatid Nuclei

Spermatids from mature male mammals are isolated using methods known in the art (see, e.g., Development (1995) 121:2397-2405). Seminiferous tubules isolated from a mature male mouse testis are placed in 1 ml of cold (4-10° C.) 0.9% NaCl containing 1% (W/v) polyvinyl pyrrolidone (PVP, Mr 360×10$^3$, ICN), and are cut into minute pieces. The seminiferous tubule suspension is mixed thoroughly with repeated pipettings with 2 ml cold PVP-saline (0.9% NaCl, 12% (w/v) PVP) to release spermatozoa, spermatids, and other reproductive cells. Cells can be identified in droplets on a Petrie dish, for example, covered with mineral oil. Cells can be maintained at approximately 16-17° C. for several hours (e.g. three hours) during this process. Round spermatids can be recognized by their small size and centrally located chromatin mass.

Spermatid clones that are connected by stable cytoplamic bridges (or ring canals) are identified and isolated using methods known in the art (see, e.g., Mol. Biol. Cell (2003) 14:2768-2780; or Histochem. Cell Biol. (1997) 108:77-81). Seminiferous vesicles are dissected free from the interstitial tissue in a Petrie dish containing phosphate-buffered saline solution, pH 7.4. The transillumination pattern may be identified under stereomicroscope, for example, and tubules at stages I-IV of the cycle are selected and cut into approximately 0.5 mm to 1 mm segments. The cells within the tubules can be extruded by lowering a cover slip (20×20 mm), for example, over the tubule allowing wicking of excess fluid to create a slightly flattened monolayer (under 40× phase-contrast optics). The spermatid clones are separated, and binding and/or hybridization procedures are performed on one, two, three, and/or four of the spermatids of a given clone using methods described herein and/or known in the art.

The hybridization/binding patterns of the probes to the nucleic acid sequences of the individual spermatid clones are compared with the known sequence or binding/hybridization pattern for diploid cells of the donor organism. Through a process of comparison and elimination, the predicted identity of the nucleic acid sequences in a spermatid clone can be determined, and the desired spermatid selected.

Example 11

Fertilization Using Spermatids and/or at Least Partially Isolated Spermatid Nuclei Oocytes are fertilized with spermatids and/or isolated nuclei using methods that are known in the art (see, e.g., Development (1995) 121:2397-2405). Whole spermatids are sucked into an injection pipette (4-10 μm internal diameter) that is attached to a Piezo electric pipette driving unit (e.g. Model PMM-10, Prima Meat Packers, Tsuchiura, Japan); partially isolated nuclei can be obtained by drawing spermatids in and out of 4 μm internal diameter injection pipettes. The zona pellucida of a mature unfertilized oocyte is drilled and the oolemma is broken by applying Piezo pulses. The entire spermatid, with or without an intact plasma membrane, or the at least partially isolated nucleus, is expelled into the ooplasm, and the pipette tip is gently withdrawn.

In one aspect, the disclosure is drawn to one or more methods comprising receiving a first input associated with a first possible dataset, the first possible dataset including data representative of one or more target genetic characteristics, wherein at least one of the one or more target genetic characteristics is a genetic characteristic other than sex chromosome identity; and determining parameters for selecting one or more reproductive components based on the first possible dataset. In some embodiments, the one or more methods comprise receiving a first input associated with a first possible dataset, the first possible dataset including data representative of one or more target genetic characteristics, wherein at least one of the one or more target genetic characteristics is a non-gender-specific genetic characteristic, or is a genetic characteristic other than gender. One or more of these methods may be used as part of one or more methods for selecting one or more germ line genomes at least partially based on one or more genetic characteristics of one or more of the one or more germ line genomes and/or implemented on one or more apparatus 410 for selecting one or more germ line genomes at least partially based on one or more genetic characteristics of one or more of the one or more germ line genomes.

Figure 2:
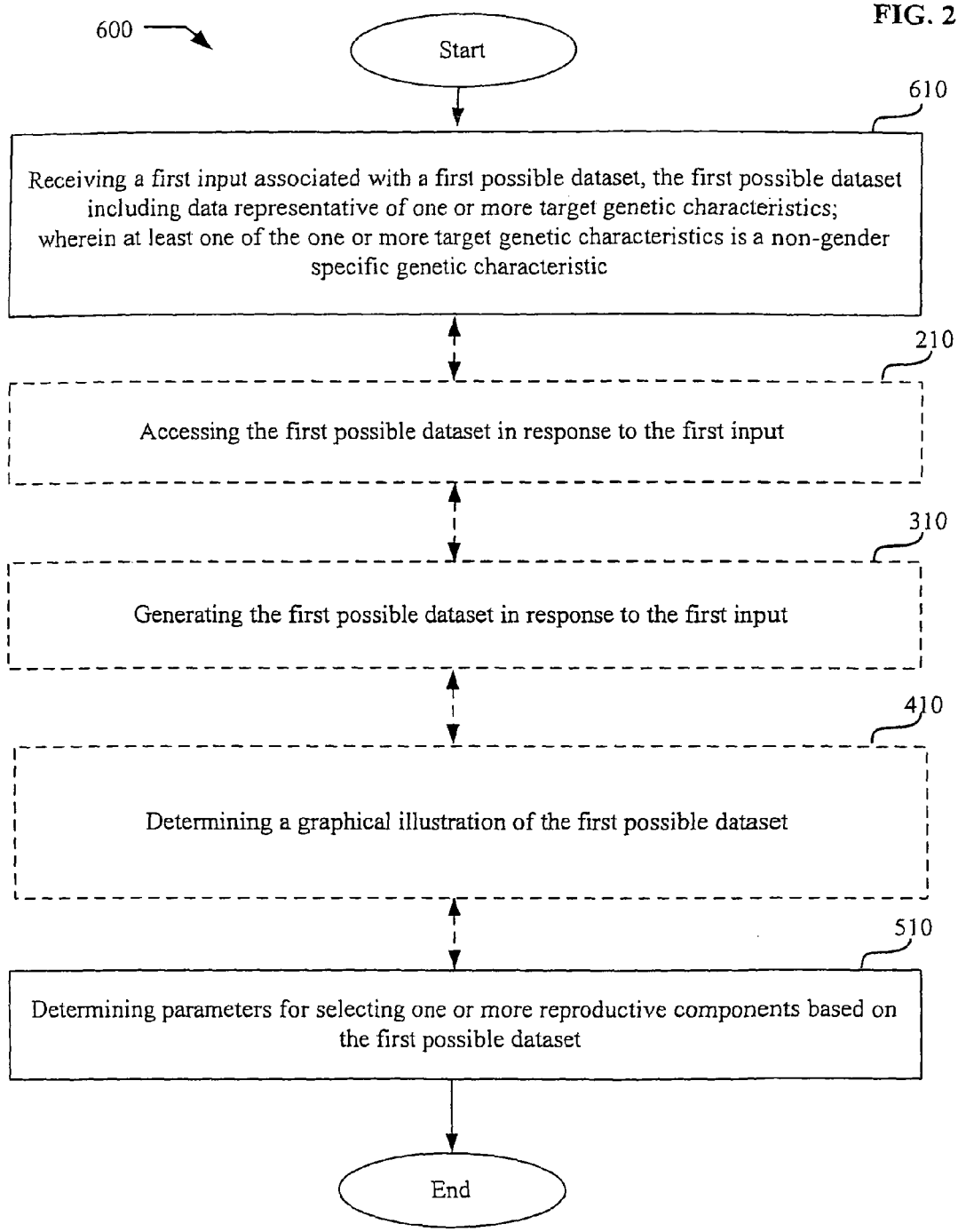
Figure 3:
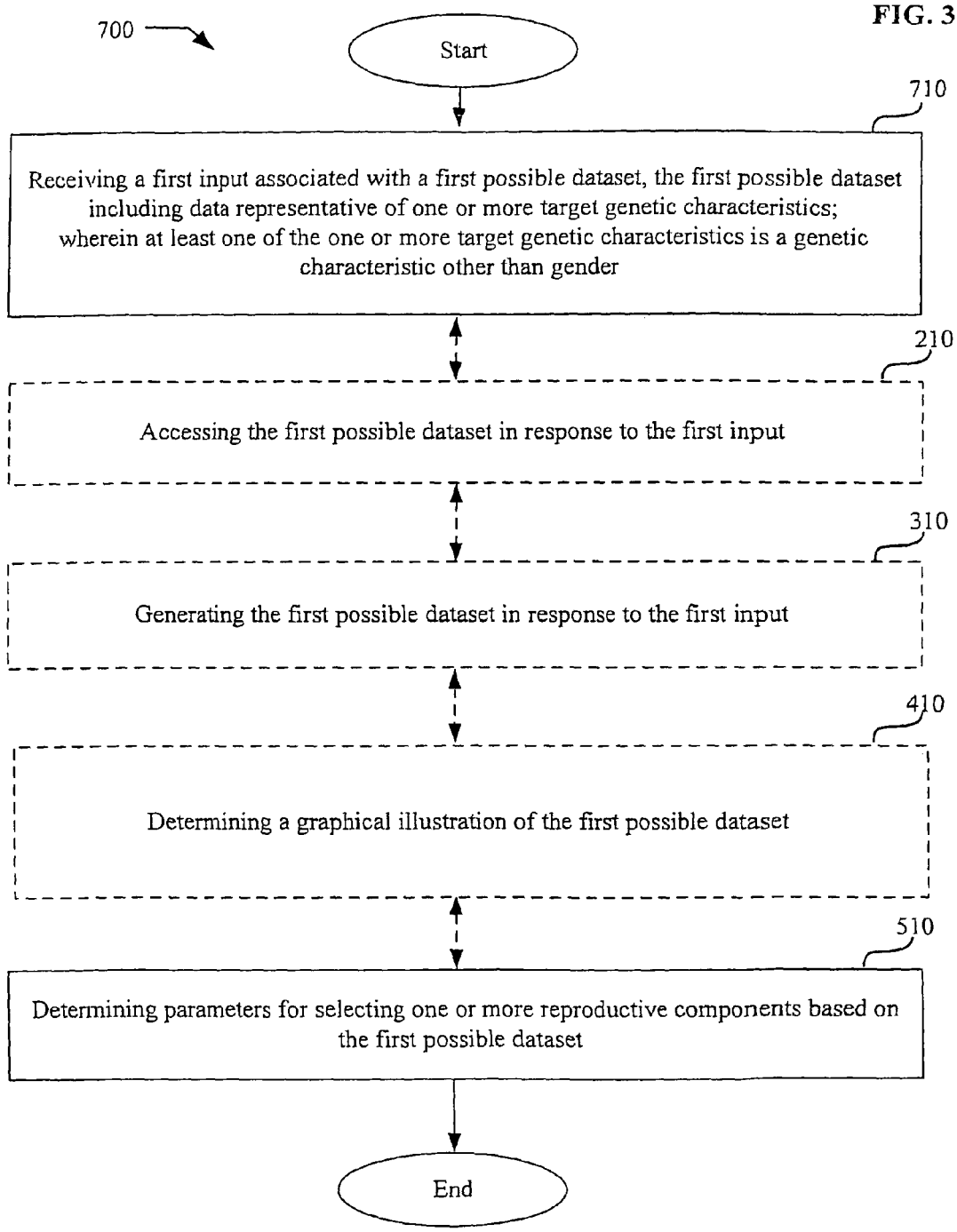

FIG. 1, FIG. 2, and FIG. 3 show operational flow 100, operational flow 600, and operational flow 700, respectively, representing illustrative embodiments of operations related to determining parameters for selecting one or more reproductive components based on the first possible dataset. In FIG. 1, FIG. 2, and FIG. 3, and in the following figures that include various illustrative embodiments of operational flows, discussion and explanation may be provided with respect to apparatus and methods described herein, and/or with respect to other examples and contexts. The operational flows may also be executed in a variety of other contexts and environments, and or in modified versions of those described herein. In addition, although some of the operational flows are presented in sequence, the various operations may be performed in various repetitions, concurrently, and/or in other orders than those that are illustrated.

After a start operation, the operational flow 100 moves to a receiving operation 110, receiving a first input associated with a first possible dataset, the first possible dataset including data representative of one or more target genetic characteristics, wherein at least one of the one or more target genetic characteristics is a genetic characteristic other than sex chromosome identity. After a start operation, the operational flow 600 moves to a receiving operation 610, receiving a first input associated with a first possible dataset, the first possible dataset including data representative of one or more target genetic characteristics, wherein at least one of the one or more target genetic characteristics is a non-gender-specific genetic characteristic. After a start operation, the operational flow 700 moves to a receiving operation 710, receiving a first input associated with a first possible dataset, the first possible dataset including data representative of one or more target genetic characteristics, wherein at least one of the one or more target genetic characteristics is a genetic characteristic other than gender.

The operational flow 100 optionally moves to an accessing operation 210, accessing the first possible dataset in response to the first input. For example, data representative of one or more target genetic characteristics may be accessed.

The operational flow 100 optionally moves to a generating operation 310, generating the first possible dataset in response to the first input. For example, data representative of one or more target genetic characteristics may be generated.

The operational flow 100 optionally moves to a determining operation 410, determining a graphical illustration of the first possible dataset. For example, data representative of one or more target genetic characteristics may be graphically represented.

Then, the operational flow 100 moves to a determining operation 510, determining parameters for selecting one or more reproductive components based on a first possible dataset. For example, one or more parameters may include, but are not limited to one or more target genetic characteristics and/or one or more genetic characteristics of one or more reproductive components.

One or more of operations 110 (and/or 610 and/or 710) through 510 may be performed or repeated, as appropriate under the circumstances, prior to an end operation.

Operations 110 to 510 may be performed with respect to a digital representation (e.g. digital data) of, for example, data representative of one or more target genetic characteristics. The logic may accept a digital or analog (for conversion into digital) representation of an input and/or provide a digitally-encoded representation of a graphical illustration, where the input may be implemented and/or accessed locally or remotely.

Operations 110 to 510 may be performed related to either a local or a remote storage of the digital data, or to another type of transmission of the digital data. In addition to inputting, accessing querying, recalling, calculating, determining or otherwise obtaining the digital data, operations may be performed related to storing, assigning, associating, displaying or otherwise archiving the digital data to a memory, including for example, sending and/or receiving a transmission of the digital data from a remote memory. Accordingly, any such operations may involve elements including at least an operator (e.g. human or computer) directing the operation, a transmitting computer, and/or receiving computer, and should be understood to occur in the United States as long as at least one of these elements resides in the United States.

Figure 4:
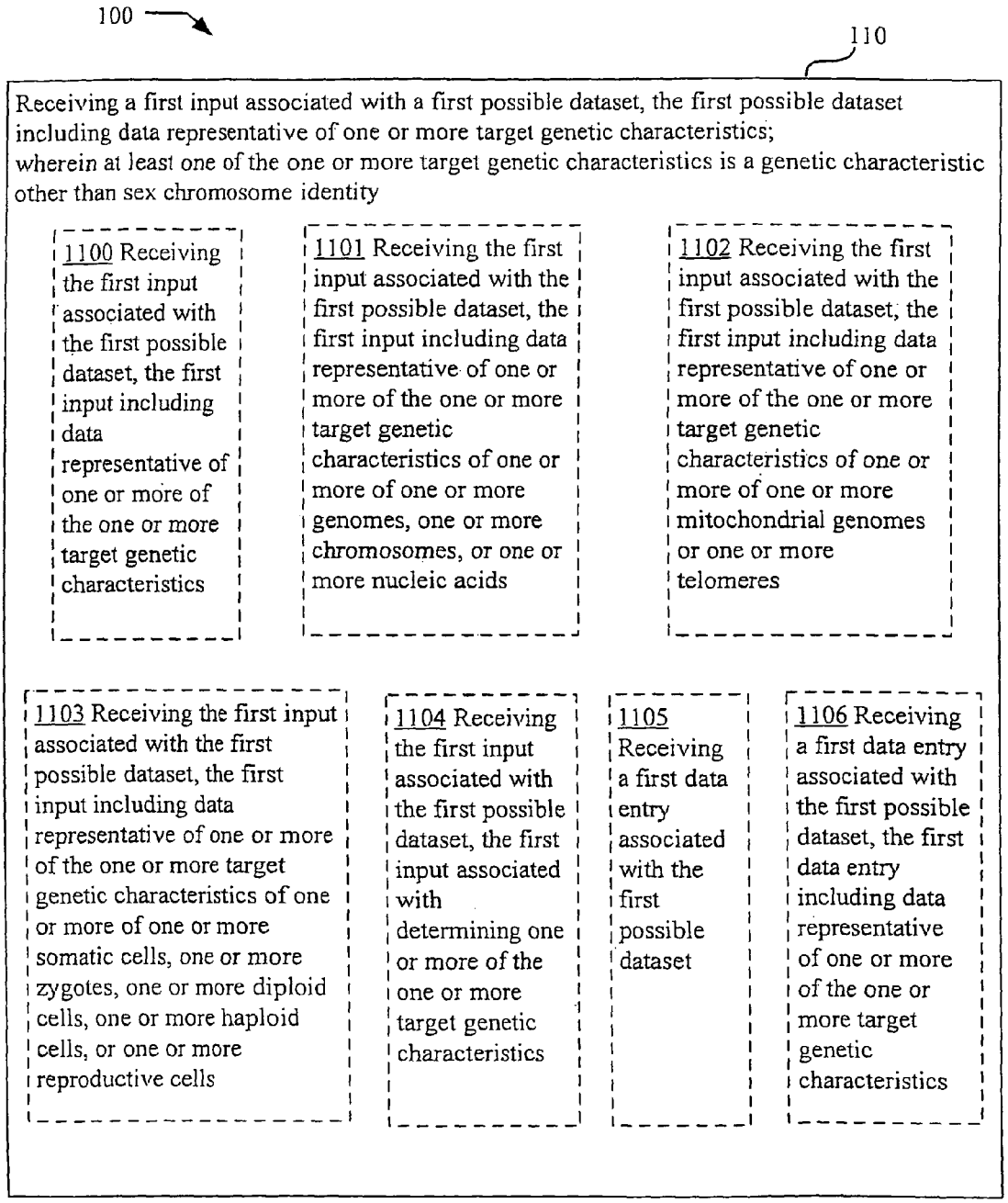
FIG. 4 shows optional embodiments of the operational flow of FIG. 1, FIG. 2, and/or FIG. 3.
Figure 5:
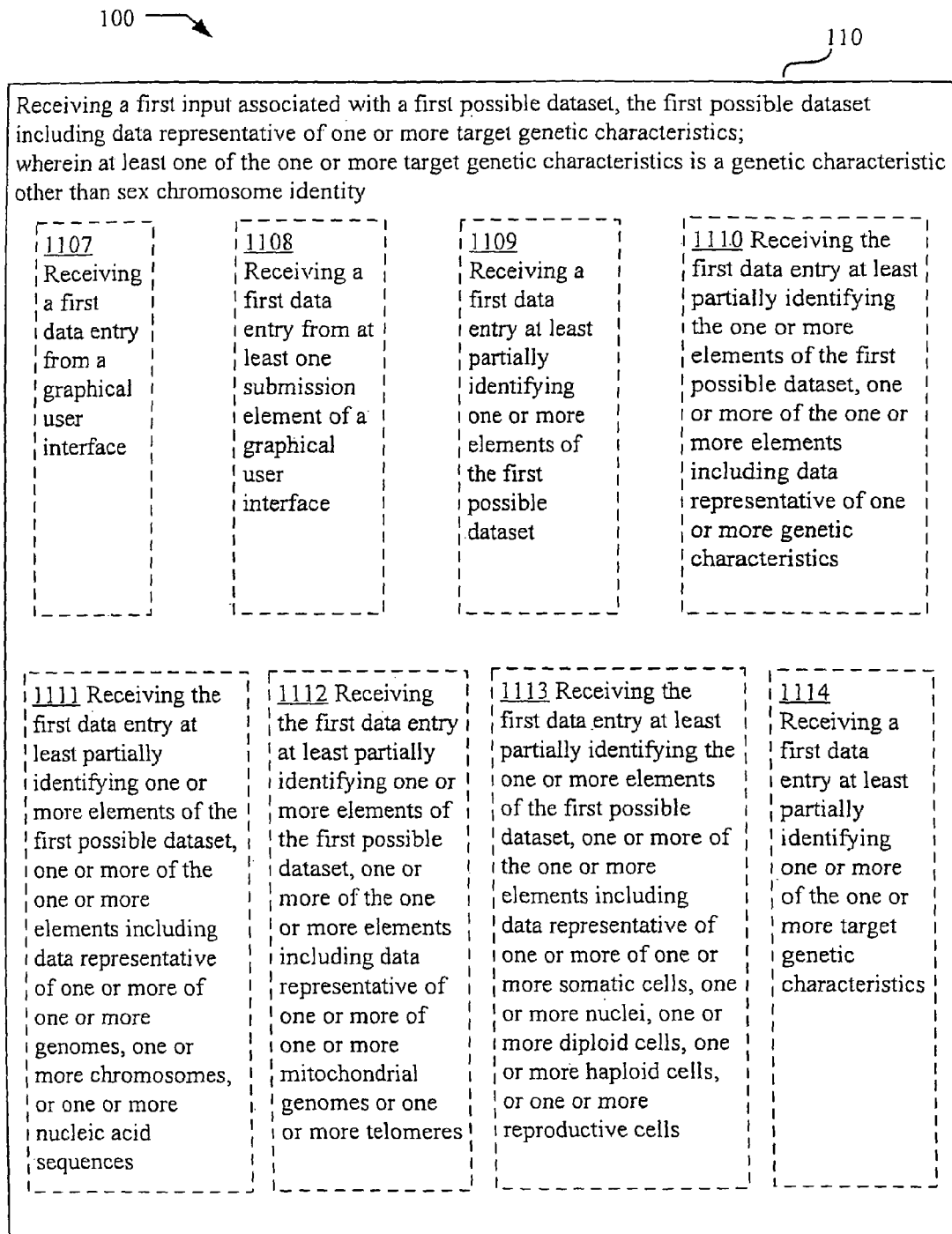
FIG. 5 shows optional embodiments of the operational flow of FIG. 1, FIG. 2, and/or FIG. 3.

FIG. 4 illustrates optional embodiments of the operational flow 100 of FIG. 1, and analogous embodiments of the operational flow 100 of FIG. 2 and/or FIG. 3 are expressly envisioned. FIG. 4 shows illustrative embodiments of the receiving operation 110, receiving a first input associated with a first possible dataset, the first possible dataset including data representative of one or more target genetic characteristics, wherein at least one or more one or more target genetic characteristics is a genetic characteristic other than sex chromosome identity, including operations receiving types of inputs and data entry and may include at least one additional operation. Receiving operations may optionally include, but are not limited to, operation 1100, operation 1101, operation 1102, operation 1103, operation 1104, operation 1105, operation 1106, operation 1107, operation 1108, operation 1109, operation 1110, operation 1111, operation 1112, operation 1113, and/or operation 1114.

At the optional operation 1100, receiving a first input associated with a first possible dataset comprises receiving the first input associated with the first possible dataset, the first input including data representative of one or more of the one or more target genetic characteristics.

In some embodiments, one or more of the one or more target genetic characteristics are selected from the group consisting of genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements. In some embodiments, one or more of the genetic attributes include one or more of one or more physical attributes, one or more psychological attributes, or one or more mental attributes.

In some embodiments, one or more of the one or more physical attributes are selected from the group consisting of characteristics associated with vision, strength, flexibility, speed, coordination, gait, lactation, fertility, weight, pelt, skin, body type, skeleto-muscular, longevity, and intelligence. In some embodiments, one or more of the one or more physical attributes are selected from the group consisting of characteristics associated with hair, eyes, height, weight, skin, fur, fleece, and wool. In some embodiments, one or more of the one or more physical attributes are selected from the group consisting of characteristics associated with hair pattern, hair color, eye color, eye sight, bone length, bone density, skin color, fur thickness, fur color, fur texture, fleece color, fleece thickness, wool thickness, and wool color. In some embodiments, one or more of the one or more physical attributes include disposition.

At the optional operation 1101, receiving a first input associated with a first possible dataset comprises receiving a first input associated with the first possible dataset, the first input including data representative of one or more of the one or more target genetic characteristics of one or more of one or more genomes, one or more chromosomes, and/or one or more nucleic acids.

At the optional operation 1102, receiving a first input associated with a first possible dataset comprises receiving a first input associated with the first possible dataset, the first input including data representative of one or more of the one or more target genetic characteristics of one or more of one or more mitochondrial genomes, and/or one or more telomeres.

At the optional operation 1103, receiving a first input associated with a first possible dataset comprises receiving a first input associated with the first possible dataset, the first input including data representative of one or more of the one or more target genetic characteristics of one or more of one or more somatic cells, one or more germ line cells, one or more zygotes, one or more diploid cells, one or more haploid cells, and/or one or more reproductive cells. In some embodiments, the first input includes data representative of one or more of the one or more target genetic characteristics of one or more of one or more sperm, one or more spermatids, one or more spermatogonia, one or more primary spermatocytes, or one or more secondary spermatocytes. In some embodiments, the first input includes data representative of one or more genetic characteristics of one or more of one or more ova, one or more first polar bodies, or one or more second polar bodies.

At the optional operation 1104, receiving a first input associated with a first possible dataset comprises receiving a first input associated with the first possible dataset, the first input associated with determining one or more of the one or more target genetic characteristics. In some embodiments, the one or more target genetic characteristics are selected from the group consisting of genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 1105 and/or 1106, receiving a first input associated with a first possible dataset comprises receiving a first data entry associated with the first possible dataset, the first data entry optionally including data representative of one or more of the one or more target genetic characteristics. In some embodiments, the one or more target genetic characteristics selected from the group consisting of genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 1107 and/or 1108, receiving a first input associated with a first possible dataset comprises receiving a first data entry from a graphical user interface, optionally from at least one submission element of a graphical user interface, and optionally at least partially identifying one or more elements of the first possible dataset.

At the optional operation 1109 and/or 1110 and/or 1111 and/or 1112 and/or 1113, receiving a first input associated with a first possible dataset comprises receiving a first data entry at least partially identifying one or more elements of the first possible dataset, one or more of the one or more elements optionally including data representative of one or more genetic characteristics. In some embodiments, one or more of the one or more elements including data representative of one or more genetic characteristics selected from the group consisting of single nucleotide polymorphisms, haplotypes, allelic markers, alleles, disease markers, genetic abnormalities, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

In some embodiments, one or more of the one or more elements optionally including data representative of one or more of one or more genomes, one or more chromosomes, and/or one or more nucleic acid sequences. In some embodiments, one or more of the one or more elements optionally including data representative of one or more of one or more mitochondrial genomes and/or one or more telomeres. In some embodiments, one or more of the one or more elements optionally including data representative of one or more of one or more somatic cells, one or more germ line cells, one or more nuclei, one or more diploid cells, one or more haploid cells, or one or more reproductive cells. In some embodiments, one or more of the one or more elements optionally including data representative of one or more of one or more sperm, one or more spermatids, one or more spermatogonia, one or more primary spermatocytes, or one or more secondary spermatocytes. In some embodiments, one or more of the one or more elements optionally including data representative of one or more of one or more ova, one or more first polar bodies, or one or more second polar bodies.

At the optional operation 1114, receiving a first input associated with a first possible dataset comprises receiving a first data entry at least partially identifying one or more of the one or more target genetic characteristics. In some embodiments, one or more of the one or more target genetic characteristics selected from the group consisting of genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

Figure 6:
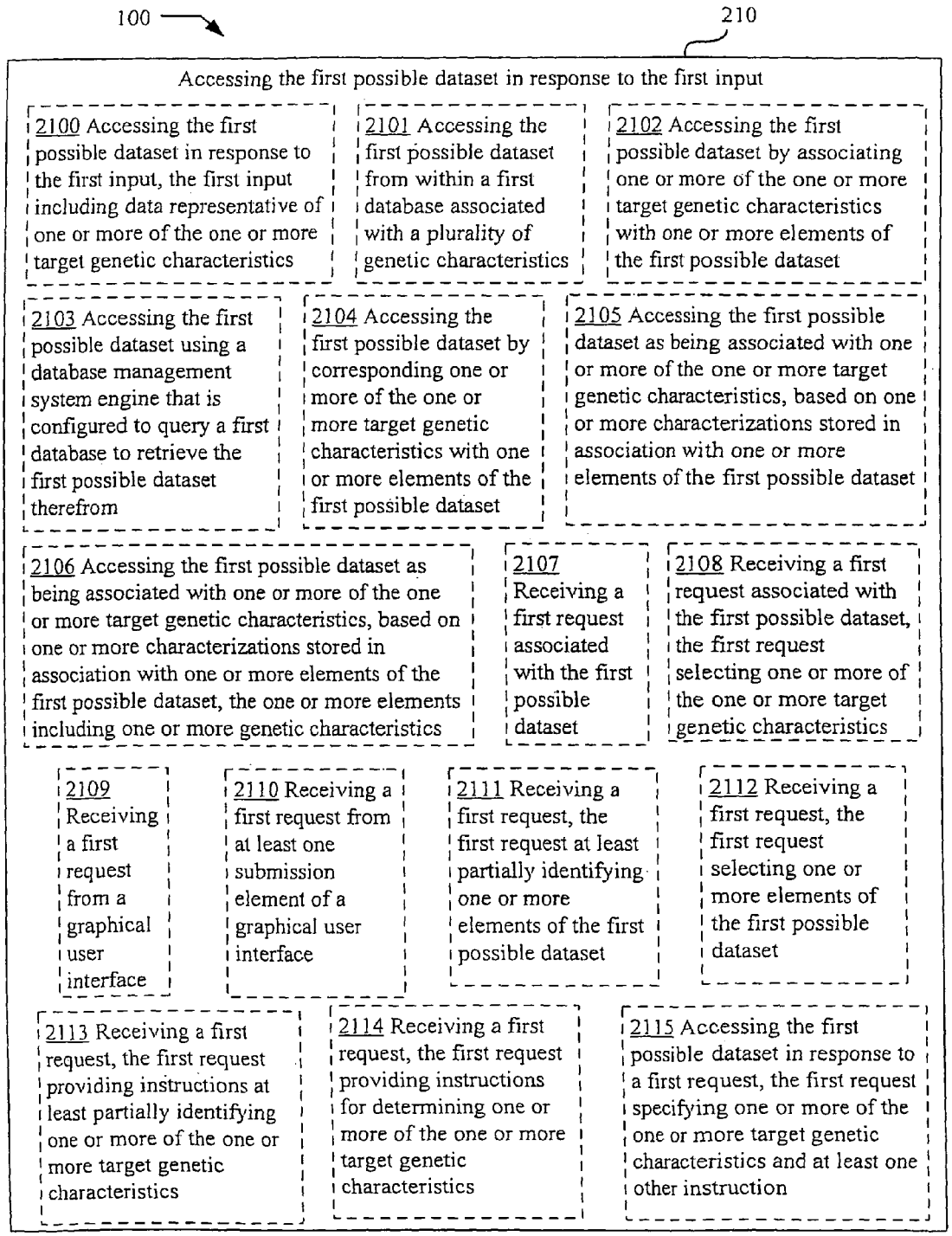
FIG. 6 shows optional embodiments of the operational flow of FIG. 1, FIG. 2, and/or FIG. 3.

FIG. 6 illustrates optional embodiments of the operational flow 100 of FIG. 1. FIG. 6 shows illustrative embodiments of the optional accessing operation 210, including operations accessing the first possible dataset in response to the first input, and may include at least one additional operation. Accessing operations may optionally include, but are not limited to, operation 2100, operation 2101, operation 2102, operation 2103, operation 2104, operation 2105, operation 2106, operation 2107, operation 2108, operation 2109, operation 2110, operation 2111, operation 2112, operation 2113, operation 2114, and/or operation 2115.

At the optional operation 2100, accessing the first possible dataset in response to the first input comprises accessing the first possible dataset in response to the first input, the first input including data representative of one or more of the one or more target genetic characteristics. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 2101, accessing the first possible dataset in response to the first input comprises accessing the first possible dataset from within a first database associated with a plurality of genetic characteristics. In some embodiments, one or more of the one or more genetic characteristics selected from the group consisting of single nucleotide polymorphisms, haplotypes, allelic markers, alleles, disease markers, genetic abnormalities, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 2102 and/or operation 2104, accessing the first possible dataset in response to the first input comprises accessing the first possible dataset by associating and/or correlating and/or corresponding data representative of one or more of the one or more target genetic characteristics with one or more elements of the first possible dataset. In some embodiments, one or snore of the one or more target genetic characteristics are selected from the group consisting of genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements with the one or more elements of the first possible dataset.

At the optional operation 2103, accessing the first possible dataset in response to the first input comprises accessing the first possible dataset using a database management system engine that is configured to query a first database to retrieve the first possible dataset therefrom.

At the optional operation 2105 and/or 2106, accessing the first possible dataset in response to the first input comprises accessing the first possible dataset as being associated and/or correlated and/or corresponded with data representative of one or more of the one or more target genetic characteristics, based on one or more characterizations stored in association with one or more elements of the first possible dataset, the one or more elements optionally including one or more genetic characteristics.

At the optional operation 2107 and/or 2108, receiving a first input associated with a first possible dataset comprises receiving a first request associated with the first possible dataset, the first request optionally selecting data representative of the one or more target genetic characteristics. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 2109 and/or 2110 and/or 2111 and/or 2112 and/or 2113, and/or 2114, and/or 2115, receiving a first input associated with a first possible dataset comprises receiving a first request from a graphical user interface, optionally from at least one submission element of a graphical user interface, optionally at least partially identifying one or more elements of the first possible dataset and/or optionally selecting one or more elements of the first possible dataset and/or optionally providing instructions identifying and/or determining and/or specifying one or more of the one or more target genetic characteristics, and optionally providing at least one other instruction.

In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

Figure 7:
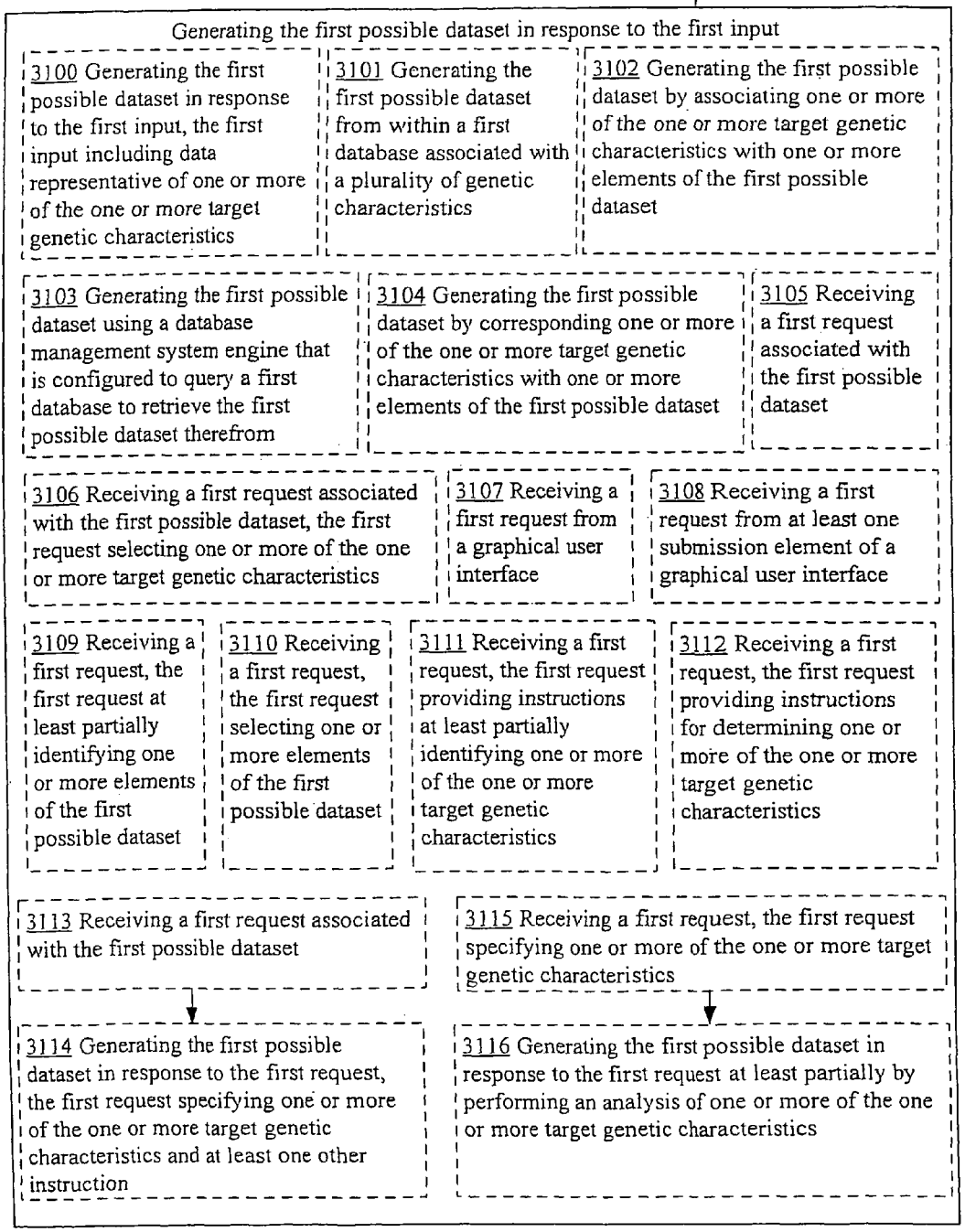
FIG. 7 shows optional embodiments of the operational flow of FIG. 1, FIG. 2, and/or FIG. 3.

FIG. 7 illustrates optional embodiments of the operational flow 100 of FIG. 1. FIG. 7 shows illustrative embodiments of the optional generating operation 310, including operations generating the first possible dataset in response to the first input, and may include at least one additional operation. Generating operations may optionally include, but are not limited to, operation 3100, operation 3101, operation 3102, operation 3103, operation 3104, operation 3105, operation 3106, operation 3107, operation 3108, operation 3109, operation 3110, operation 3111, operation 3112, operation 3113, operation 3114, operation 3115, and/or operation 3116.

At the optional operation 3100, generating the first possible dataset in response to the first input comprises generating the first possible dataset in response to the first input, the first input including data representative of one or more of one or more target genetic characteristics. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 3101, generating the first possible dataset in response to the first input comprises generating the first possible dataset from within a first database associated with a plurality of genetic characteristics. In some embodiments, one or more of the one or more genetic characteristics are selected from the group consisting of one or more single nucleotide polymorphisms, haplotypes, allelic markers, alleles, disease markers, genetic abnormalities, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 3102, generating the first possible dataset in response to the first input comprises generating the first possible dataset by associating data representative of one or more of the one or more target genetic characteristics with one or more elements of the first possible dataset. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 3103, generating the first possible dataset in response to the first input comprises generating the first possible dataset using a database management system engine that is configured to query a first database to retrieve the first possible dataset therefrom.

At the optional operation 3104, generating the first possible dataset in response to the first input comprises generating the first possible dataset by corresponding data representative of one or more of the one or more target genetic characteristics with one or more elements of the first possible dataset. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 3105 and/or 3106, receiving a first input associated with a first possible dataset comprises receiving a first request associated with the first possible dataset, the first request optionally selecting one or more of the one or more target genetic characteristics. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 3107 and/or 3108, receiving a first input associated with a first possible dataset comprises receiving a first request from a graphical user interface, and optionally from at least one submission element of a graphical user interface.

At the optional operation 3109 and/or 3110, receiving a first input associated with a first possible dataset comprises receiving a first request, the first request at least partially identifying one or more elements of the first possible dataset and/or optionally selecting one or more elements of the first possible dataset and/or optionally providing instructions at least partially identifying one or more elements of the first possible dataset.

At the optional operation 3111 and/or 3112, receiving a first input associated with a first possible dataset comprises receiving a first request, the first request providing instructions at least partially identifying one or more of the one or more target genetic characteristics and/or providing instructions for determining one or more of the one or more target genetic characteristics. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 3113 and 3114, receiving a first input associated with a first possible dataset comprises receiving a first request associated with the first possible dataset 3113, and generating the first possible dataset in response to the first request, the first request optionally specifying one or more of the one or more target genetic characteristics and optionally at least one other instruction 3114. In some embodiments, receiving a first input associated with a first possible dataset comprises receiving a first request associated with the first possible dataset, the first request selecting and/or determining data representative of one or more of the one or more target genetic characteristics, and generating the first possible dataset in response to the first input.

In some embodiments, receiving a first input associated with a first possible dataset comprises receiving a first request from a graphical user interface, optionally from at least one submission element of a graphical user interface, optionally at least partially identifying one or more elements of the first possible dataset, and optionally selecting one or more elements of the first possible dataset, and generating the first possible dataset in response to the first input. In some embodiments, receiving a first input associated with a first possible dataset comprises receiving a first request from at least one submission element of a graphical user interface, the first request providing instructions identifying and/or determining data representative of one or more of the one or more target genetic characteristics, and generating the first possible dataset in response to the first input.

At the optional operations 3115 and 3116, receiving a first input associated with a first possible dataset comprises receiving a first request, the first request specifying data representative of one or more of the one or more target genetic characteristics 3115; and generating the first possible dataset in response to the first request at least partially by performing an analysis of data representative of the one or more target genetic characteristics 3116. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

In some embodiments, receiving a first input associated with a first possible dataset comprises receiving a first request, the first request specifying data representative of one or more of the one or more target genetic characteristics, and generating the first possible dataset in response to the first request at least partially by performing an analysis of data representative of one or more of one or more target nucleic acid sequences and/or target haplotypes.

Figure 8:
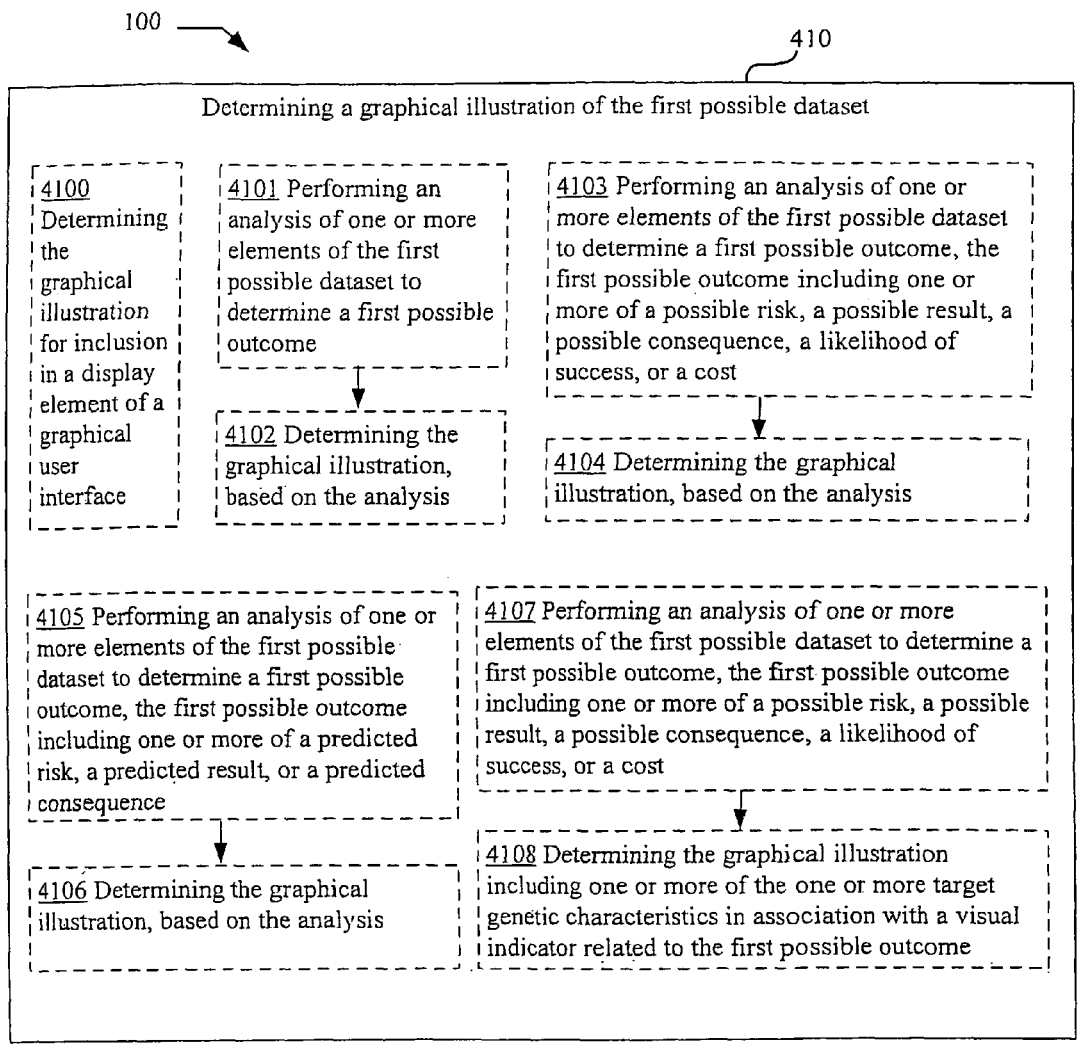
FIG. 8 shows optional embodiments of the operational flow of FIG. 1, FIG. 2, and/or FIG. 3.
Figure 9:
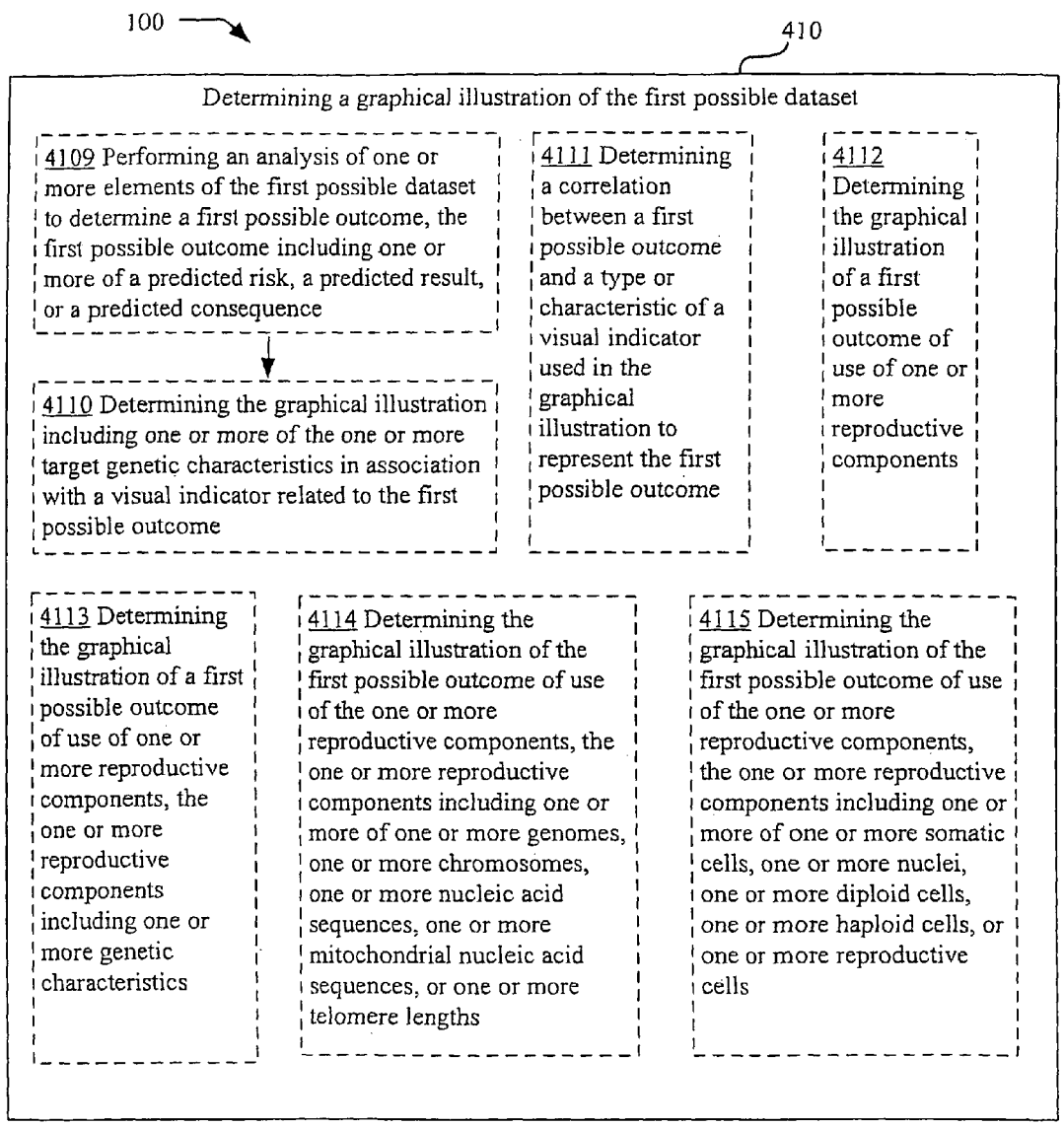
FIG. 9 shows optional embodiments of the operational flow of FIG. 1, FIG. 2, and/or FIG. 3.

FIG. 8 and FIG. 9 illustrate optional embodiments of the operational flow 100 of FIG. 1. FIG. 8 and FIG. 9 show illustrative embodiments of the optional determining operation 410, including operations determining a graphical illustration of the first possible dataset, and may include at least one additional operation. Determining operations may optionally include, but are not limited to, operation 4100, operation 4101, operation 4102, operation 4103, operation 4104, operation 4105, operation 4106, operation 4107, operation 4108, operation 4109, operation 4110, operation 4111, operation 4112, operation 4113, operation 4114, and/or operation 4115.

At the optional operation 4100, determining a graphical illustration of the first possible dataset comprises determining the graphical illustration of the first possible dataset for inclusion in a display element of a graphical user interface.

At the operations 4101 and 4102, determining a graphical illustration of the first possible dataset comprises performing an analysis of one or more elements of the first possible dataset to determine a first possible outcome 4101; and determining the graphical illustration based on the analysis 4102.

At the optional operations 4103 and 4104, determining a graphical illustration of the first possible dataset comprises performing an analysis of one or more elements of the first possible dataset to determine a first possible outcome, the first possible outcome including one or more of a possible risk, a possible result, a possible consequence, a likelihood of success, or a cost 4103; and determining the graphical illustration based on the analysis 4104.

At the optional operations 4105 and 4106, determining a graphical illustration of the first possible dataset comprises performing an analysis of one or more elements of the first possible dataset to determine a first possible outcome, the first possible outcome including one or more of a predicted risk, a predicted result, a predicted consequence, a predicted likelihood of success, or a predicted cost 4105; and determining the graphical illustration based on the analysis 4106.

At the optional operations 4107 and 4108, determining a graphical illustration of the first possible dataset comprises performing an analysis of one or more elements of the first possible dataset to determine a first possible outcome, the first possible outcome including one or more of a possible risk, a possible result, a possible consequence, a likelihood of success, or a cost 4107; and determining the graphical illustration including data representative of one or more of the one or more target genetic characteristics in association with a visual indicator related to the first possible outcome 4108. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operations 4109 and 4110, determining a graphical illustration of the first possible dataset comprises performing an analysis of one or more elements of the first possible dataset to determine a first possible outcome, the first possible outcome including one or more of a predicted risk, a predicted result, a predicted consequence, a predicted likelihood of success, or a predicted cost 4109; and determining the graphical illustration including data representative of one or more of the one or more target genetic characteristics in association with a visual indicator related to the first possible outcome 4110. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 4111, determining a graphical illustration of the first possible dataset comprises determining a correlation between a first possible outcome and a type or characteristic of a visual indicator used in the graphical illustration to represent the first possible outcome.

At the optional operations 4112, 4113, 4114, and/or 4115, determining a graphical illustration of the first possible dataset comprises determining the graphical illustration of a first possible outcome based on use of one or more of the one or more reproductive components 4112, the one or more reproductive components optionally including one or more genetic characteristics 4113, optionally including one or more of one or more genomes, one or more chromosomes, one or more nucleic acid sequences, one or more mitochondrial nucleic acid sequences, and/or one or more telomeres and/or telomere lengths 4114, and/or optionally including one or more of one or more somatic cells, one or more germ line cells, one or more nuclei, one or more diploid cells, one or more haploid cells, and/or one or more reproductive cells 4115.

In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

In some embodiments, one or more of the one or more reproductive components include, but are not limited to, one or more of one or more spermatozoa, one or more spermatids, one or more spermatogonia, one or more primary spermatocytes, and/or one or more secondary spermatocytes. In some embodiments, one or more of the one or more reproductive components include, but are not limited to, one or more of one or more ova, one or more first polar bodies, and/or one or more second polar bodies.

Figure 10:
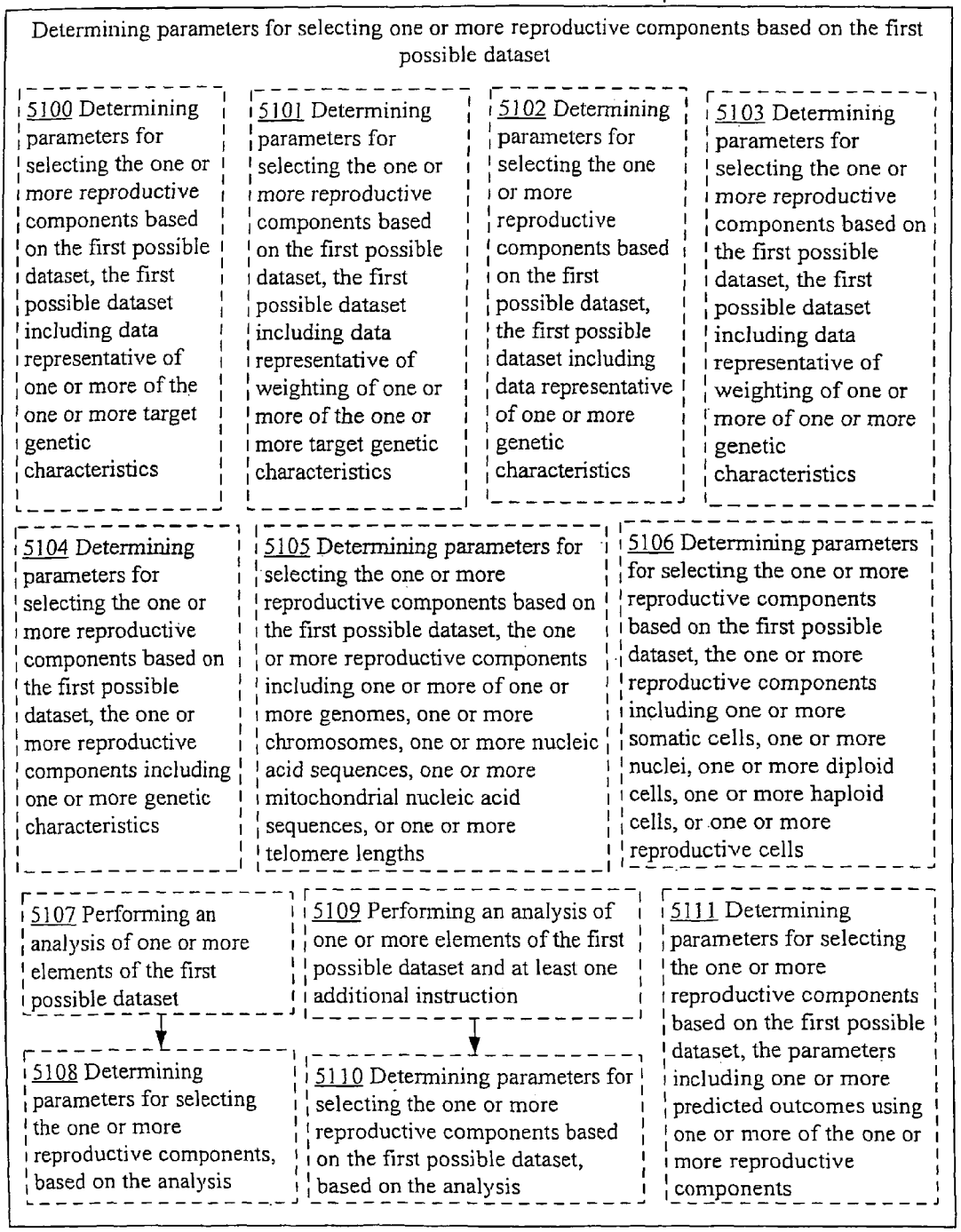
FIG. 10 shows optional embodiments of the operational flow of FIG. 1, FIG. 2, and/or FIG. 3.
Figure 11:
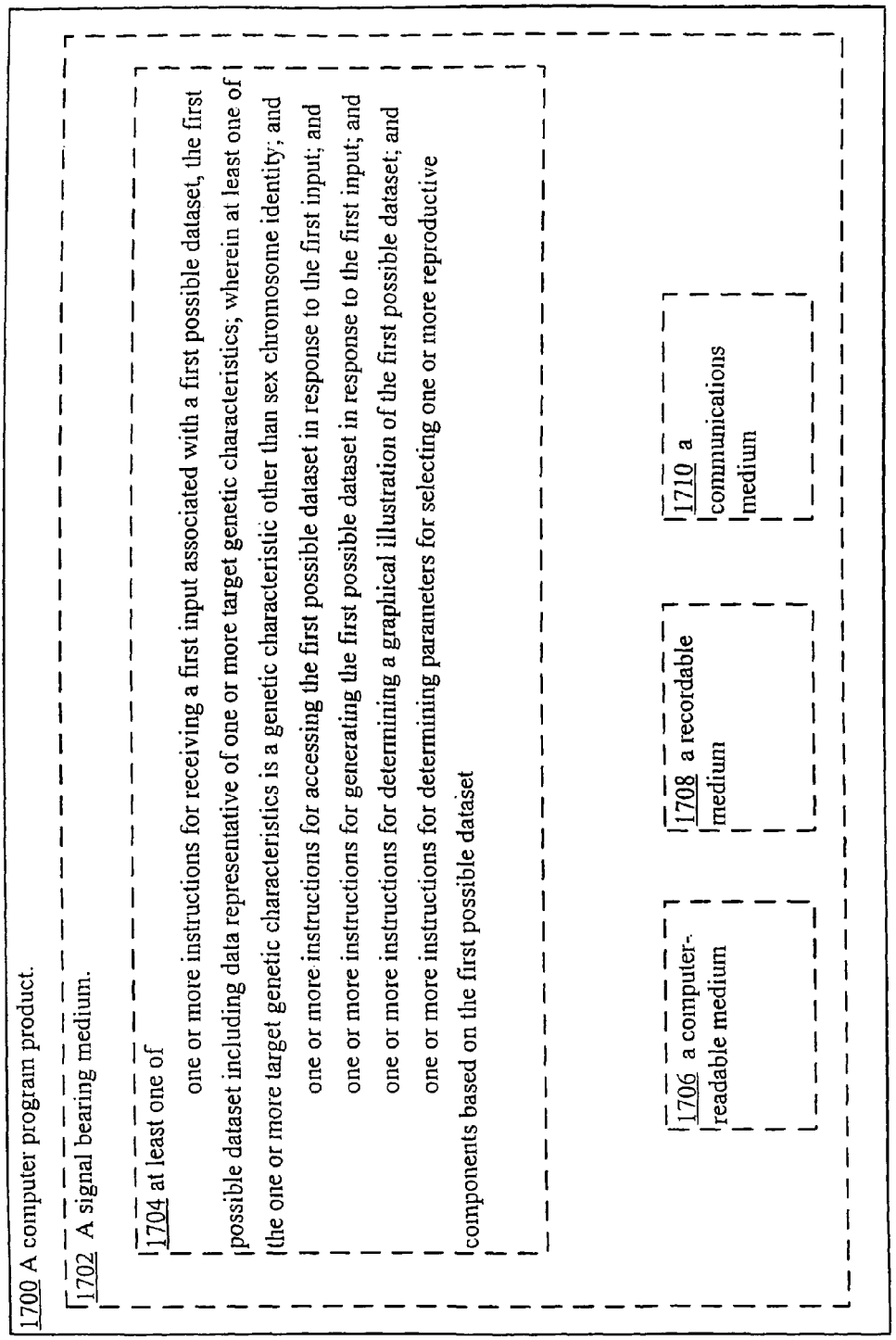
FIG. 11, FIG. 12, and FIG. 13 show partial views of an illustrative embodiment of a computer program product that includes a computer program for executing a computer process on a computing device.

FIG. 10 illustrates optional embodiments of the operational flow 100 of FIG. 11. FIG. 18 shows illustrative embodiments of the determining operation 510, including operations determining parameters for selecting one or more reproductive components based on the first possible dataset, and may include at least one additional operation: Determining operations may optionally include, but are not limited to, operation 5100, operation 5101, operation 5102, operation 5103, operation 5104, operation 5105, operation 5106, operation 5107, operation 5108, operation 5109, operation 5110, and/or operation 5111.

At the optional operation 5100 and/or 5101, determining parameters for selecting one or more reproductive components based on the first possible dataset comprises determining parameters for selecting one or more reproductive components based on the first possible dataset, the first possible dataset including data representative of one or more of the one or more target genetic characteristics and/or weighting of one or more target genetic characteristics. In some embodiments, one or more of the one or more target genetic characteristics are selected from the group consisting of one or more genetic attributes, single nucleotide polymorphisms, haplotypes, allelic markers, alleles, disease markers, genetic abnormalities, genetic diseases, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 5102 and/or 5103, determining parameters for selecting one or more reproductive components based on the first possible dataset comprises determining parameters for selecting one or more reproductive components based on the first possible dataset, the first possible dataset including data representative of one or more of the one or more genetic characteristics and/or weighting of one or more of the one or more genetic characteristics. In some embodiments, one or more of the one or more genetic characteristics are selected from the group consisting of one or more single nucleotide polymorphisms, haplotypes, allelic markers, alleles, disease markers, genetic abnormalities, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements.

At the optional operation 5104 and/or 5105 and/or 5106, determining parameters for selecting one or more reproductive components based on the first possible dataset comprises determining parameters for selecting one or more reproductive components based on the first possible dataset, the one or more reproductive components including one or more genetic characteristics 5104, optionally including one or more of one or more genomes, one or more chromosomes, one or more nucleic acid sequences, one or more mitochondrial nucleic acid sequences, and/or one or more telomeres and/or telomere lengths 5105, and/or optionally including one or more of one or more somatic cells, one or more germ line cells, one or more nuclei, one or more diploid cells, one or more haploid cells, and/or one or more reproductive cells 5106.

In some embodiments, one or more of the one or more genetic characteristics are selected from the group consisting of single nucleotide polymorphisms, haplotypes, allelic markers, alleles, disease markers, genetic abnormalities, chromosomal abnormalities, genetic mutations, inversions, deletions, duplications, recombinations, chromosomes, nucleic acid sequences, genes, protein coding sequences, introns, exons, regulatory sequences, intergenic sequences, mitochondrial nucleic acid sequences, mitochondria, telomeres, telomere repeats, telomere lengths, centromere repeats, centromeres, methylation pattern, and epigenetic elements. In some embodiments, one or more reproductive components include, but are not limited to, one or more of one or more sperm, one or more spermatids, one or more spermatogonia, one or more primary spermatocytes, one or more secondary spermatocytes, one or more ova, one or more first polar bodies, and/or one or more second polar bodies.

At the optional operations 5107 and 5108, determining parameters for selecting one or more reproductive components based on the first possible dataset comprises performing an analysis of one or more elements of the first possible dataset 5107; and determining parameters for selecting one or more reproductive components, based on the analysis 5108.

At the optional operations 5109 and 5110, determining parameters for selecting one or more reproductive components based on the first possible dataset comprises performing an analysis of one or more elements of the first possible dataset and at least one additional instruction 5109; and determining parameters for selecting the one or more reproductive components, based on the analysis 5110.

At the optional operation 5111, determining parameters for selecting one or more reproductive components based on the first possible dataset comprises determining parameters for selecting one or more reproductive components based on the first possible dataset, the parameters including one or more predicted outcomes using one or more of the one or more reproductive components.

In some embodiments, determining parameters for selecting one or more reproductive components based on the first possible dataset comprises determining parameters for selecting the one or more reproductive components based on the first possible dataset, the parameters including one or more predicted outcomes selected from the group consisting of data characteristic of one or more of predicted risk, predicted result, predicted consequence, predicted likelihood of success, and predicted cost and/or data characteristic of weighting of one or more of predicted risk, predicted result, predicted consequence, predicted likelihood of success, and predicted cost. In some embodiments, determining parameters for selecting the one or more reproductive components based on the first possible dataset comprises determining parameters for selecting the one or more reproductive components based on the first possible dataset, the parameters including one or more predicted outcomes selected from the group consisting of data characteristic of one or more of a possible risk, a possible result, or a possible consequence and/or data characteristic of weighting of one or more of a possible risk, a possible result, or a possible consequence.

Figure 12:
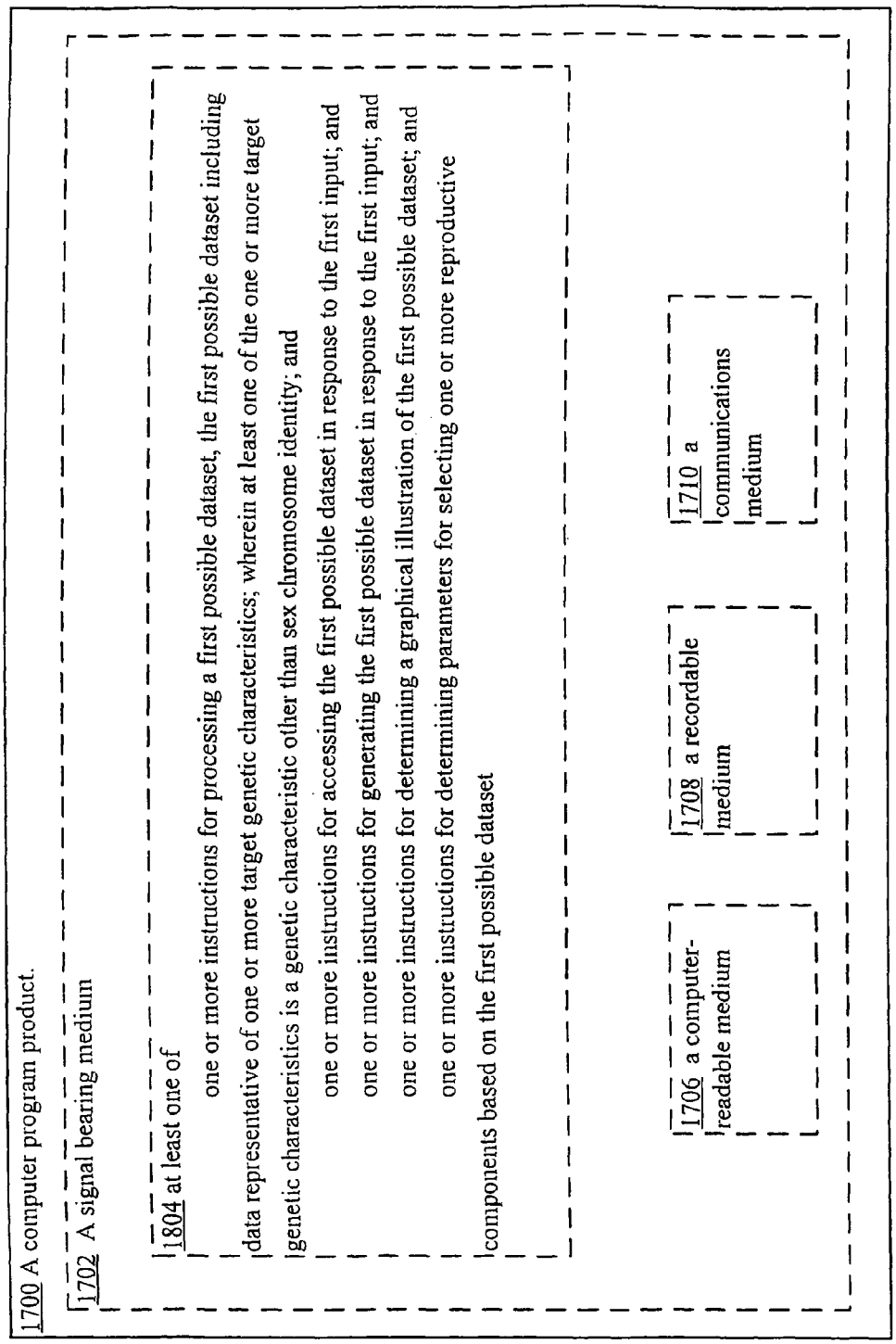
Figure 13:
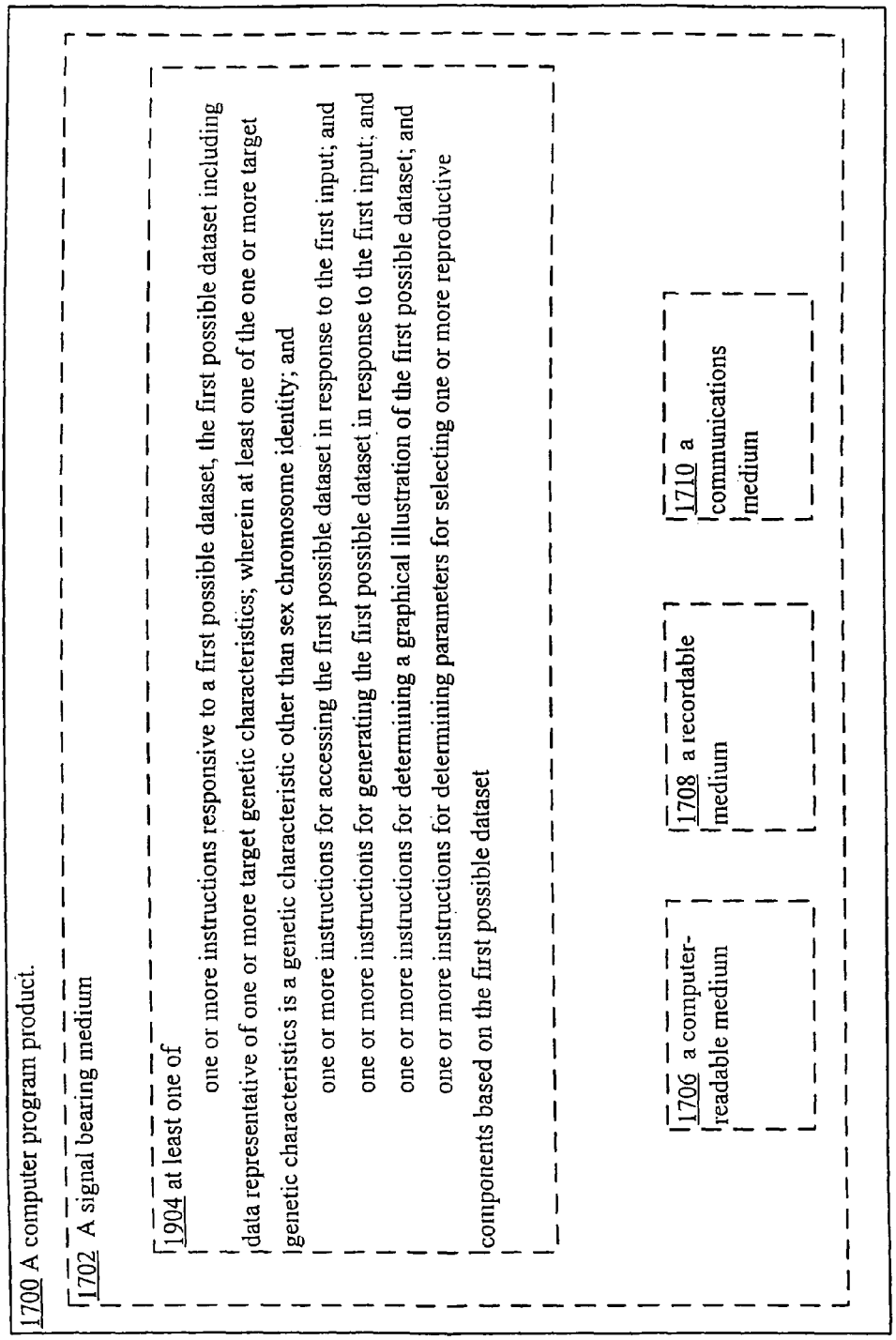

FIG. 11, FIG. 12, and/or FIG. 13 show a schematic of a partial view of an illustrative computer program product 1700 that includes a computer program for executing a computer process on a computing device. An illustrative embodiment of the example computer program product is provided using a signal bearing medium 1702, and may include at least one instruction of 1704, 1804, and/or 1904: one or more instructions for receiving a first input associated with a first possible dataset 1704, one or more instructions for processing a first possible dataset 1804, and/or one or more instructions responsive to a first possible dataset 1904, the first possible dataset including data representative of one or more target genetic characteristics, wherein at least one of the one or more target genetic characteristics is optionally a non-gender-specific genetic characteristic, a genetic characteristic other than sex chromosome identity, and/or a genetic characteristic other than gender; one or more instructions for accessing the first possible dataset in response to the first input; one or more instructions for generating the first possible dataset in response to the first input; one or more instructions for determining a graphical illustration of the first possible dataset; or one or more instructions for determining parameters for selecting one or more reproductive components based on the first possible dataset. The one or more instructions may be, for example, computer executable and/or logic implemented instructions. In some embodiments, the signal bearing medium 1702 of the one or more computer program 1700 products include a computer readable medium 1706, a recordable medium 1708, and/or a communications medium 1710.

Figure 14:
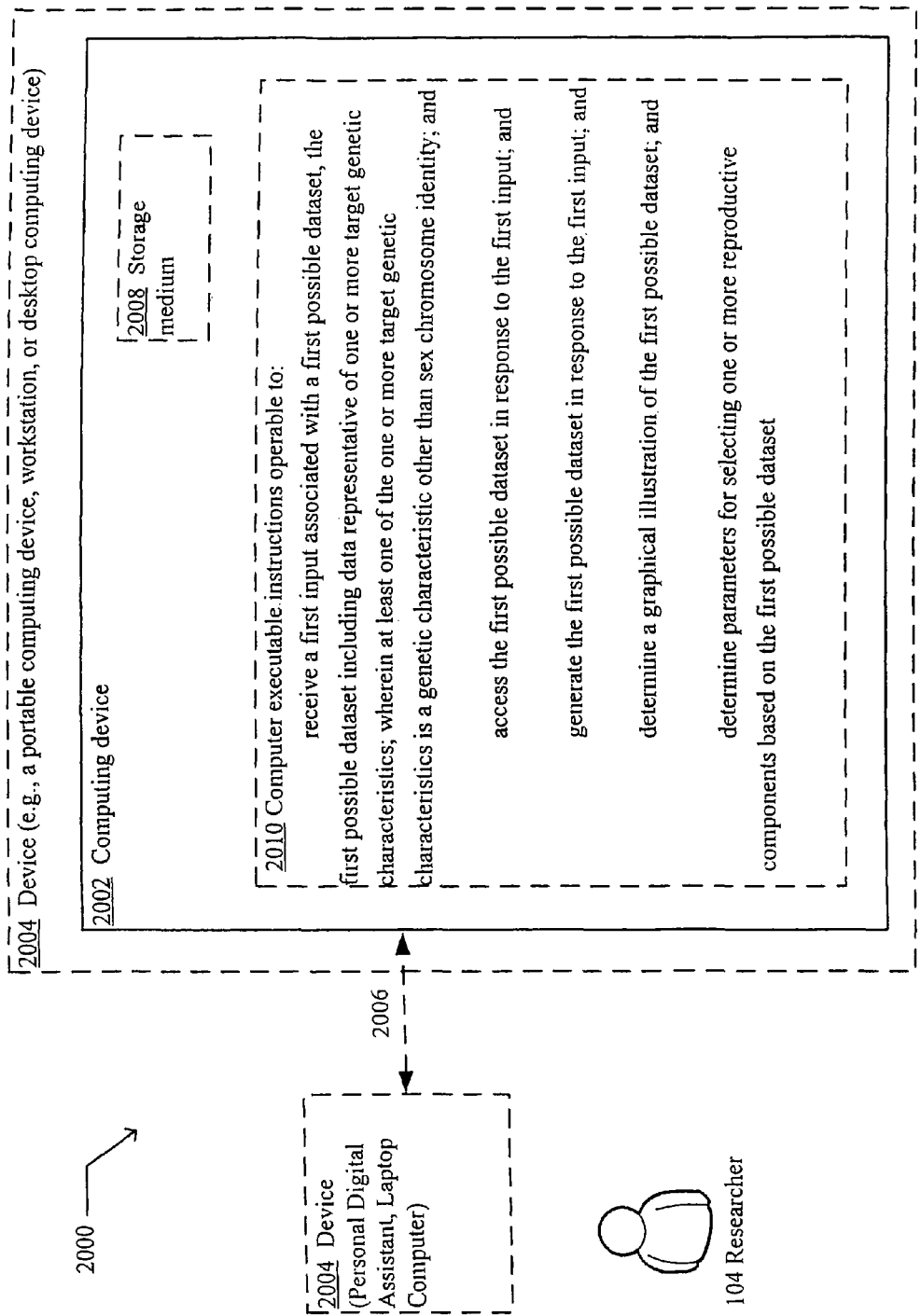
FIG. 14 shows an illustrative embodiment of a system in which embodiments may be implemented.

FIG. 14 shows a schematic of an illustrative system 2000 in which embodiments may be implemented. The system 2000 may include a computing system environment. The system 2000 also illustrates an operator and/or researcher 104 using a device 2004 that is optionally shown as being in communication with a computing device 2002 by way of an optional coupling 2006. The optional coupling may represent a local, wide area, or peer-to-peer network, or may represent a bus that is internal to a computing device (e.g. in illustrative embodiments the computing device 2002 is contained in whole or in part within the device 2004, one or more apparatus 410, one or more characterization units 419, one or more computing units 428, one or more controller units 426, one or more monitoring units 424, one or more hybridization units 422, one or more sequencing units 430, one or more amplifying units 432, and/or one or more decondensing units 434). An optional storage medium 2008 may be any computer storage medium.

The computing device 2002 includes one or more computer executable instructions 2010 that when executed on the computing device 2002 cause the computing device 2002 to receive the first input associated with the first possible dataset, the first possible dataset including data representative of one or more target genetic characteristics, optionally wherein at least one of the one or more target genetic characteristics is a genetic characteristic other than sex chromosome identity; optionally access the first possible dataset in response to the first input; optionally generate the first possible dataset in response the first input; optionally determine a graphical illustration of the first possible dataset; and determine parameters for selecting one or more reproductive components at least partially based on a first possible dataset. In some embodiments, at least one of the target genetic characteristics is a non-gender specific target characteristic, a genetic characteristic other than sex chromosome identity, and/or a genetic characteristic other than gender. In some illustrative embodiments, the computing device 2002 may optionally be contained in whole or in part within one or more units of an apparatus 410 of FIG. 15 (e.g. one or more characterization units 419, one or more computing units 428, one or more controller units 426, one or more monitoring units 424, one or more hybridization units 422, one or more sequencing units 430, one or more amplifying units 432, and/or one or more decondensing units 434), or may optionally be contained in whole or in part within the operator device 2004.

The system 2000 includes at least one computing device (e.g. 2004 and/or 2002 and/or one or more computing units 428 of FIG. 15) on which the computer-executable instructions 2010 may be executed. For example, one or more of the computing devices (e.g. 2002, 2004, 428) may execute the one or more computer executable instructions 2010 and output a result and/or receive information from the operator 104 (optionally from one or more apparatus 410, one or more characterization units 419, one or more controller units 426, one or more monitoring units 424, one or more hybridization units 422, one or more decondensing units 434, one or more sequencing units 430, and/or one or more amplifying units 432) on the same or a different computing device (e.g. 2002, 2004, 428) and/or output a result and/or receive information from an apparatus 410, one or more characterization units 419, one or more controller units 426, one or more monitoring units 424, one or more hybridization units 422, one or more decondensing units 434, one or more sequencing units 430, and/or one or more amplifying units 432 in order to perform and/or implement one or more of the techniques, processes, or methods described herein, or other techniques.

The computing device (e.g. 2002 and/or 2004 and/or 428) may include one or more of a desktop computer, a workstation computer, a computing system comprised a cluster of processors, a networked computer, a tablet personal computer, a laptop computer, or a personal digital assistant, or any other suitable computing unit. In some embodiments, any one of the one or more computing devices (e.g. 2002 and/or 2004 and/or 428) may be operable to communicate with a database to access the first possible dataset and/or subsequent datasets. In some embodiments, the computing device (e.g. 2002 and/or 2004 and/or 428) is operable to communicate with the apparatus 410.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein, including but not limited to patents, patent applications, and non-patent literature, are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
   determining one or more genetic characteristics of three related polar body genomes; and
   separating one or more of the one or more related female germ line genomes based at least partially on the one or more genetic characteristics of one or more of the three related polar body genomes.

2. A method comprising:
   determining one or more genetic characteristics of three related polar body genomes; and
   selecting one or more of one or more related female germ line genomes based at least partially on the one or more genetic characteristics of one or more of the three related polar body genomes, wherein one or more of the three related polar body genomes are at least partially isolated from the three related polar bodies.

3. The method of claim 2, wherein one or more of the three related polar body genomes are part of one or more of the three polar bodies.

4. The method of claim 2, wherein one or more of the three related polar body genomes are one or more first polar body genomes.

5. The method of claim 2, wherein one or more of the three related polar body genomes are one or more second polar body genomes.

6. The method of claim 2, wherein one or more of the one or more related female germ line genomes are at least partially isolated from one or more ova.

7. The method of claim 2, wherein one or more of the one or more related female germ line genomes are part of one or more ova.

8. The method of claim 2, wherein one or more of the one or more related female germ line genomes are at least partially isolated from one or more of the three related polar bodies.

9. The method of claim 2, wherein one or more of the one or more related female germ line genomes are part of one or more of the three related polar bodies.

10. The method of claim 2, wherein determining one or more genetic characteristics of one or more related female germ line genomes comprises:
    determining the one or more genetic characteristics of the one or more related female germ line genomes at least partially based on the genetic characteristics of one or more of the three related polar body genomes.

11. The method of claim 2, wherein determining one or more genetic characteristics of one or more related female germ line genomes comprises:
    subtractively determining the one or more genetic characteristics of the one or more related female germ line genomes.

12. The method of claim 11, wherein subtractively determining the one or more genetic characteristics of the one or more related female germ line genomes comprises:
    determining one or more of the one or more genetic characteristics of the three related polar bodies; and
    comparing the one or more genetic characteristics of the three related polar bodies with one or more known genetic characteristics of a related diploid genome.

13. The method of claim 2, wherein determining one or more genetic characteristics of three related polar body genomes comprises:
    destructively determining one or more of the one or more genetic characteristics of the three related polar body genomes.

14. The method of claim 2, wherein determining one or more genetic characteristics of three related polar body genomes comprises:
    amplifying one or more nucleic acid sequences of the three related polar body genomes.

15. The method of claim 14, wherein amplifying one or more nucleic acid sequences of the three related polar body genomes comprises:
    amplifying in vitro the one or more nucleic acid sequences of the three related polar body genomes.

16. The method of claim 14, wherein amplifying one or more nucleic acid sequences of the three related polar body genomes comprises:
    amplifying in situ the one or more nucleic acid sequences of the three related polar body genomes.

17. The method of claim 14, wherein amplifying one or more nucleic acid sequences of the three related polar body genomes comprises:
    destructively amplifying the one or more nucleic acid sequences of the three related polar body genomes.

18. The method of claim 2, wherein determining the one or more genetic characteristics of the three related polar body genomes comprises:
    sequencing in vitro one or more nucleic acids of the three related polar body genomes.

19. The method of claim 2, wherein determining the one or more genetic characteristics of the one or more related polar body genomes comprises:
    sequencing in situ one or more nucleic acids of the one or more related polar body genomes.

20. The method of claim 2, wherein determining the one or more genetic characteristics of the three related polar body genomes comprises:
    destructively sequencing one or more nucleic acids of the three related polar body genomes.

21. The method of claim 2, wherein determining one or more genetic characteristics of three related polar body genomes comprises:
    co-localizing one or more of one or more probes or one or more molecular markers with one or more nucleic acid sequences of the three related polar body genomes.

22. The method of claim 2, wherein determining the one or more genetic characteristics of the one or more related polar body genomes comprises:
    hybridizing one or more probes in vitro to one or more nucleic acid sequences of the one or more related polar body genomes.

23. The method of claim 2, wherein determining the one or more genetic characteristics of the one or more related polar body genomes comprises:
    hybridizing one or more probes in situ to one or more nucleic acid sequences of the one or more related polar body genomes.

24. The method of claim 2, wherein determining the one or more genetic characteristics of the one or more related polar body genomes comprises:
    destructively hybridizing one or more probes to one or more nucleic acid sequences of the one or more related polar body genomes.

25. The method of claim 2, wherein determining the one or more genetic characteristics of the three related polar body genomes comprises:
    detecting one or more nucleic acid sequences of the three related polar body genomes.

26. The method of claim 25, wherein detecting one or more nucleic acid sequences of the three related polar body genomes comprises:
    detecting one or more of one or more probes or one or more molecular markers associated with the one or more nucleic acid sequences of the three related polar body genomes.

27. The method of claim 2, wherein determining one or more genetic characteristics of the three related polar body genomes comprises:
    receiving data representative of the one or more genetic characteristics of the three related polar body genomes.

28. The method of claim 27, wherein receiving data representative of the one or more genetic characteristics of the three related polar body genomes comprises:
    receiving data representative of one or more nucleic acid sequences of the three related polar body genomes.

29. The method of claim 2, further comprising:
    co-localizing one or more of one or more probes or one or more molecular markers with one or more nucleic acid sequences of the three related polar body genomes.

30. The method of claim 2, further comprising:
hybridizing one or more molecular markers with one or more nucleic acid sequences of the three related polar body genomes.

31. The method of claim 2, comprising:
detecting one or more nucleic acid sequences of the three related polar body genomes.

32. The method of claim 2, comprising:
analyzing the one or more genetic characteristics of the three related polar body genomes.

33. The method of claim 32, wherein analyzing the one or more genetic characteristics of the one or more related polar body genomes comprises:
comparing the one or more genetic characteristics of the three related polar body genomes with one or more of one or more reference genetic characteristics or one or more target genetic characteristics.

34. The method of claim 32, wherein analyzing the one or more genetic characteristics of the one or more related polar body genomes comprises:
analyzing one or more of one or more single nucleotide polymorphisms, one or more chromosomes, one or more methylation patterns, or one or more nucleic acid sequences of the one or more related polar body genomes.

35. The method of claim 2, wherein determining one or more genetic characteristics of one or more related female germ line genomes at least partially based on the genetic characteristics of one or more of the three related polar body genomes comprises:
deducing the one or more genetic characteristics of the one or more related female germ line genomes at least partially based on the genetic characteristics of one or more of the three related polar body genomes.

36. The method of claim 2, wherein determining one or more genetic characteristics of one or more related female germ line genomes at least partially based on the genetic characteristics of one or more of the three related polar body genomes comprises:
identifying the one or more genetic characteristics of the one or more related female germ line genomes at least partially based on the genetic characteristics of one or more of the three related polar body genomes.

37. The method of claim 2, further comprising:
analyzing the one or more genetic characteristics of the one or more related female germ line genomes.

38. The method of claim 37, wherein analyzing the one or more genetic characteristics of the one or more related female germ line genomes comprises:
comparing the one or more genetic characteristics of the one or more related female germ line genomes with one or more of one or more reference genetic characteristics or one or more target genetic characteristics.

39. The method of claim 38, further comprising:
selecting one or more of the one or more reference genetic characteristics or the one or more target genetic characteristics at least partially based on one or more genetic characteristics of one or more male germ line haploid genomes.

40. The method of claim 38, wherein said step of comparing comprises:
selecting for one or more of the one or more related female germ line genomes at least partially based on the presence of one or more of the one or more reference genetic characteristics or the one or more target genetic characteristics.

41. The method of claim 38, wherein said step of comparing comprises:
selecting against one or more of the one or more related female germ line genomes at least partially based on the presence of one or more of the one or more reference genetic characteristics or the one or more target genetic characteristics.

42. The method of claim 2, further comprising:
separating the selected one or more related female germ line genomes.

43. The method of claim 2, further comprising:
co-localizing one or more of the one or more related female germ line genomes with one or more male germ line haploid genomes.

44. The method of claim 2, further comprising:
providing one or more of the one or more related female germ line genomes to one or more male germ line haploid genomes.

45. A method comprising:
determining one or more genetic characteristics of one or more related polar body genomes;
selecting one or more of one or more related female germ line genomes based at least partially on the one or more genetic characteristics of one or more of the one or more related polar body genomes, wherein one or more of the one or more related polar body genomes are at least partially isolated from one or more polar bodies;
analyzing the one or more genetic characteristics of the one or more related polar body genomes; and
comparing the one or more genetic characteristics of the one or more related polar body genomes with a weighted combination of one or more of one or more reference genetic characteristics or one or more target genetic characteristics.

46. The method of claim 45, further comprising:
determining one or more of the one or more reference genetic characteristics or the one or more target genetic characteristics at least partially based on one or more genetic characteristics of one or more male germ line haploid genomes.

47. The method of claim 45, further comprising:
selecting one or more of the one or more reference genetic characteristics or the one or more target genetic characteristics at least partially based on one or more genetic characteristics of one or more male germ line haploid genomes.

48. A method comprising:
determining one or more genetic characteristics of one or more related polar body genomes;
selecting one or more of one or more related female germ line genomes based at least partially on the one or more genetic characteristics of one or more of the one or more related polar body genomes, wherein one or more of the one or more related polar body genomes are at least partially isolated from one or more polar bodies;
analyzing the one or more genetic characteristics of the one or more related female germ line genomes and
comparing the one or more genetic characteristics of the one or more related female germ line genomes with a weighted combination of one or more of one or more reference genetic characteristics or one or more target genetic characteristics.

49. A method comprising:
analyzing the one or more genetic characteristics of one or more related female germ line genomes;
comparing the one or more genetic characteristics of the one or more related female germ line genomes with one or more of one or more reference genetic characteristics or one or more target genetic characteristics; and selecting for one or more of the one or more related female germ line genomes at least partially based on the presence of a weighted combination of one or more of the one or more reference genetic characteristics or the one or more target genetic characteristics, wherein one or more of the one or more related polar body genomes are at least partially isolated from the one or more polar bodies.

50. A method comprising:

analyzing the one or more genetic characteristics of one or more related female germ line genomes;

comparing the one or more genetic characteristics of the one or more related female germ line genomes with one or more of one or more reference genetic characteristics or one or more target genetic characteristics; and selecting against one or more of the one or more related female germ line genomes at least partially based on the presence of a weighted combination of one or more of the one or more reference genetic characteristics or the one or more target genetic characteristics, wherein one or more of the one or more related polar body genomes are at least partially isolated from the one or more polar bodies.

* * * * *